(12) United States Patent
Gallop et al.

(10) Patent No.: US 7,569,576 B2
(45) Date of Patent: *Aug. 4, 2009

(54) CYCLIC 1-(ACYLOXY)-ALKYL PRODRUGS OF GABA ANALOGS, COMPOSITIONS AND USES THEREOF

(75) Inventors: Mark A Gallop, Los Altos, CA (US); Jia-Ning Xiang, Palo Alto, CA (US); Fenmei Yao, Mountain View, CA (US); Laxminarayan Bhat, Santa Clara, CA (US)

(73) Assignee: XenoPort, Inc., Santa Clara, CA (US)

( * ) Notice: Subject to any disclaimer, the term of this patent is extended or adjusted under 35 U.S.C. 154(b) by 273 days.

This patent is subject to a terminal disclaimer.

(21) Appl. No.: 11/332,607

(22) Filed: Jan. 12, 2006

(65) Prior Publication Data

US 2006/0122125 A1 Jun. 8, 2006

Related U.S. Application Data

(63) Continuation of application No. 10/393,806, filed on Mar. 20, 2003, now Pat. No. 7,026,351.

(60) Provisional application No. 60/367,297, filed on Mar. 20, 2002.

(51) Int. Cl.
*A61K 31/515* (2006.01)
*A61K 31/44* (2006.01)
*C07D 317/00* (2006.01)
*C07D 407/00* (2006.01)
*C07D 313/16* (2006.01)

(52) U.S. Cl. .................. 514/266; 549/271; 549/296; 549/304; 549/305; 549/307; 514/450; 514/459; 514/460; 514/491

(58) Field of Classification Search .................. 549/304, 549/305, 266, 271, 296, 307; 514/450, 459, 514/460, 491

See application file for complete search history.

(56) References Cited

U.S. PATENT DOCUMENTS

| | | |
|---|---|---|
| 4,024,175 A | 5/1977 | Satzinger et al. |
| 5,563,175 A | 10/1996 | Silverman et al. |
| 6,020,370 A | 2/2000 | Horwell et al. |
| 6,028,214 A | 2/2000 | Silverman et al. |
| 6,054,482 A | 4/2000 | Augart et al. |
| 6,103,932 A | 8/2000 | Horwell et al. |
| 6,117,906 A | 9/2000 | Silverman et al. |
| 7,026,351 B2 * | 4/2006 | Gallop et al. ............ 514/450 |

FOREIGN PATENT DOCUMENTS

| | | |
|---|---|---|
| WO | WO 92/09560 | 6/1992 |
| WO | WO 93/23383 | 11/1993 |
| WO | WO 97/29101 | 8/1997 |
| WO | WO 97/33858 | 9/1997 |
| WO | WO 97/33859 | 9/1997 |
| WO | WO 98/17627 | 4/1998 |
| WO | WO 99/08671 | 2/1999 |
| WO | WO 99/21824 | 5/1999 |
| WO | WO 99/31057 | 6/1999 |
| WO | WO 99/31074 | 6/1999 |
| WO | WO 99/31075 | 6/1999 |
| WO | WO 99/61424 | 12/1999 |
| WO | WO 00/15611 | 3/2000 |
| WO | WO 00/31020 | 6/2000 |
| WO | WO 00/50027 | 8/2000 |
| WO | WO 01/80830 A2 | 11/2001 |
| WO | WO 02/00209 A2 | 1/2002 |

OTHER PUBLICATIONS

Bryans et al., 3-substituted GABA analogs with central nervous system activity: a review. Med. Res. Rev. Mar. 1999;19(2):149-77.
Jezyk et al., Transport of pregabalin in rat intestine and Caco-2 monolayers. Pharm. Res. Apr. 1999; 16(4):519-26.
Magnus, Nonepileptic uses of gabapentin. Epilepsia. 1999; 40 Suppl 6:S66-72.
Verma et al., Osmotically controlled oral drug delivery. Drug Dev. Ind. Pharm. Jul. 2000; 26(7):695-708.

* cited by examiner

*Primary Examiner*—Janet L. Andres
*Assistant Examiner*—Raymond Covington
(74) *Attorney, Agent, or Firm*—D. Byron Miller; William R. Lambert; Lucy S. Chang

(57) ABSTRACT

The present invention provides cyclic 1-(acyloxy)-alkyl prodrugs of GABA analogs, methods of making cyclic 1-(acyloxy)-alkyl prodrugs of GABA analogs and compositions of cyclic 1-(acyloxy)-alkyl prodrugs of GABA analogs. The present invention also provides methods of using cyclic 1-(acyloxy)-alkyl prodrugs of GABA analogs and compositions of cyclic 1-(acyloxy)-alkyl prodrugs of GABA analogs.

30 Claims, No Drawings

CYCLIC 1-(ACYLOXY)-ALKYL PRODRUGS OF GABA ANALOGS, COMPOSITIONS AND USES THEREOF

This application is a continuation of application Ser. No. 10/393,806, filed Mar. 20, 2003 now U.S. Pat. No. 7,026,351, which claims the benefit under 35 U.S.C. § 119(e) of U.S. Provisional Application No. 60/367,297, filed Mar. 20, 2002, the contents of each of which are incorporated by reference herein in their entirety.

1. FIELD OF THE INVENTION

The present invention relates generally to cyclic 1-(acyloxy)-alkyl prodrugs of GABA analogs, methods of making cyclic 1-(acyloxy)-alkyl prodrugs of GABA analogs and compositions of cyclic 1-(acyloxy)-alkyl prodrugs of GABA analogs. The present invention also relates generally to methods of using cyclic 1-(acyloxy)-alkyl prodrugs of GABA analogs and compositions of cyclic 1-(acyloxy)-alkyl prodrugs of GABA analogs. More particularly, the present invention relates to cyclic 1-(acyloxy)-alkyl prodrugs of gabapentin and pregabalin, methods of making cyclic 1-(acyloxy)-alkyl prodrugs of gabapentin and pregabalin, compositions of 1-(acyloxy)-alkyl prodrugs of gabapentin and pregabalin, methods of using cyclic 1-(acyloxy)-alkyl prodrugs of gabapentin and pregabalin and compositions of cyclic 1-(acyloxy)-alkyl prodrugs of gabapentin and pregabalin.

2. BACKGROUND OF THE INVENTION

Gamma ("γ")-aminobutyric acid ("GABA") is one of the major inhibitory transmitters in the central nervous system of mammals. GABA is not transported efficiently into the brain from the bloodstream (i.e., GABA does not effectively cross the blood-brain barrier). Consequently, brain cells provide virtually all of the GABA found in the brain (GABA is biosynthesized by decarboxylation of glutamic acid with pyridoxal phosphate).

GABA regulates neuronal excitability through binding to specific membrane proteins (i.e., GABAA receptors), which results in opening of an ion channel. The entry of chloride ion through the ion channel leads to hyperpolarization of the recipient cell, which consequently prevents transmission of nerve impulses to other cells. Low levels of GABA have been observed in individuals suffering from epileptic seizures, motion disorders (e.g., multiple sclerosis, action tremors, tardive dyskinesia), panic, anxiety, depression, alcoholism and manic behavior.

The implication of low GABA levels in a number of common disease states and/or common medical disorders has stimulated intensive interest in preparing GABA analogs, which have superior pharmaceutical properties in comparison to GABA (e.g., the ability to cross the blood brain barrier). Accordingly, a number of GABA analogs, with considerable pharmaceutical activity have been synthesized in the art (See, e.g., Satzinger et al., U.S. Pat. No. 4,024,175; Silverman et al., U.S. Pat. No. 5,563,175; Horwell et al., U.S. Pat. No. 6,020,370; Silverman et al., U.S. Pat. No. 6,028,214; Horwell et al., U.S. Pat. No. 6,103,932; Silverman et al., U.S. Pat. No. 6,117,906; Silverman, International Application No. WO 92/09560; Silverman et al., International Application No. WO 93/23383; Horwell et al., International Application No. WO 97/29101; Horwell et al., International Application No. WO 97/33858; Horwell et al., International Application No. WO 97/33859; Bryans et al., International Application No. WO 98/17627; Guglietta et al., International Application No. WO 99/08671; Bryans et al., International Application No. WO 99/21824; Bryans et al., International Application No. WO 99/31057; Belliotti et al., International Application No. WO 99/31074; Bryans et al., International Application No. WO 99/31075; Bryans et al., International Application No. WO 99/61424; Bryans et al., International Application No. WO 00/15611; Bryans, International Application No. WO 00/31020; Bryans et al., International Application No. WO 00/50027; and Bryans et al, International Application No. WO 02/00209).

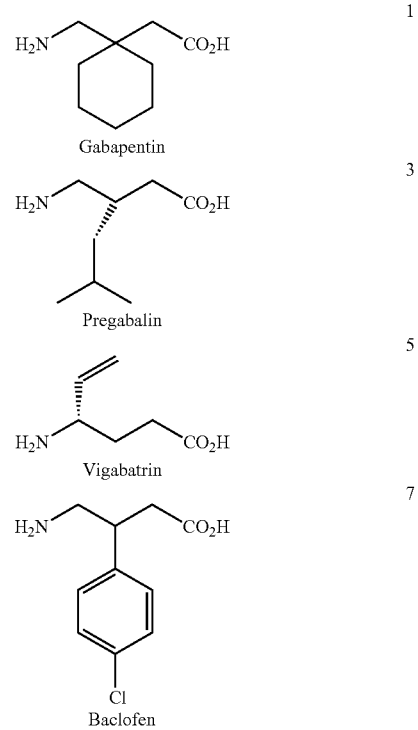

Pharmaceutically important GABA analogs include, for example, gabapentin 1, pregabalin 3, vigabatrin 5, and baclofen 7, shown above. Gabapentin is a lipophilic GABA analog that can pass through the blood-brain barrier, which has been used to clinically treat epilepsy since 1994. Gabapentin also has potentially useful therapeutic effects in chronic pain states (e.g., neuropathic pain, muscular and skeletal pain), psychiatric disorders (e.g., panic, anxiety, depression, alcoholism and manic behavior), movement disorders (e.g., multiple sclerosis, action tremors, tardive dyskinesia), etc. (Magnus, *Epilepsia*, 1999, 40:S66-S72). Currently, gabapentin is also used in the clinical management of neuropathic pain. Pregabalin, which possesses greater potency in preclinical models of pain and epilepsy than gabapentin is presently in Phase III clinical trials.

A significant problem with many GABA analogs is intramolecular reaction of the γ amino group with the carboxyl functionality to form the γ-lactam as exemplified for gabapentin below. Formation of γ-lactam 9 presents serious difficulties in formulating gabapentin because of its toxicity. For example, gabapentin has a toxicity ($LD_{50}$, mouse) of more than 8000 mg/kg, while the corresponding lactam 9 has a toxicity ($LD_{50}$, mouse) of 300 mg/kg. Consequently, formation of side products such as lactams during synthesis of GABA analogs and/or formulation and/or storage of either GABA analogs or compositions of GABA analogs must be minimized for safety reasons (particularly, in the case of gabapentin).

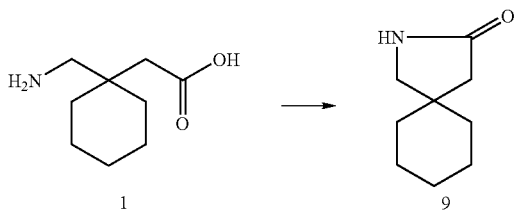

The problem of lactam contamination of GABA analogs, particularly in the case of gabapentin, has been partially overcome through use of special additional purification steps, precise choice of adjuvant materials in pharmaceutical compositions and careful control procedures (Augurt et al., U.S. Pat. No. 6,054,482). However, attempts to prevent lactam contamination have not been entirely successful, in either synthesis or storage of GABA analogs such as gabapentin or compositions thereof.

Rapid systemic clearance is another significant problem with many GABA analogs including gabapentin, which consequently require frequent dosing to maintain a therapeutic or prophylactic concentration in the systemic circulation (Bryans et al., *Med. Res. Rev.,* 1999, 19, 149-177). For example, typical dosing regimens of 300-600 mg t.i.d. of gabapentin are typically used for anticonvulsive therapy. Higher doses (1800-3600 mg/d in divided doses) are typically used for the treatment of neuropathic pain states.

Sustained released formulations are a conventional solution to the problem of rapid systemic clearance, as is well known to those of skill in the art (See, e.g., "Remington's Pharmaceutical Sciences," Philadelphia College of Pharmacy and Science, 17th Edition, 1985). Osmotic delivery systems are also recognized methods for sustained drug delivery (See, e.g., Verma et al., *Drug Dev. Ind. Pharm.,* 2000, 26:695-708).

Many GABA analogs, including gabapentin and pregabalin, are not absorbed via the large intestine. Rather, these compounds are typically absorbed in the small intestine by the large neutral amino acid transporter ("LNAA") (Jezyk et al., *Pharm. Res.,* 1999, 16, 519-526). The rapid passage of conventional dosage forms through the proximal absorptive region of the gastrointestinal tract has prevented the successful application of sustained release technologies to many GABA analogs.

Thus, there is a significant need for effective sustained release versions of GABA analogs to minimize increased dosing frequency due to rapid systemic clearance of these compounds. There is also a need for pure GABA analogs, (particularly gabapentin and pregabalin analogs) which are substantially pure and do not spontaneously lactamize during either formulation or storage.

3. SUMMARY OF THE INVENTION

The present invention addresses these and other needs by providing cyclic 1-(acyloxy)-alkyl prodrugs of GABA analogs, compositions of cyclic 1-(acyloxy)-alkyl prodrugs of GABA analogs and methods for making cyclic 1-(acyloxy)-alkyl prodrugs of GABA analogs. The present invention also provides methods for using cyclic 1-(acyloxy)-alkyl prodrugs of GABA analogs, methods for using compositions of cyclic 1-(acyloxy)-alkyl prodrugs of GABA analogs and compositions of cyclic 1-(acyloxy)-alkyl prodrugs of GABA analogs for treating or preventing common diseases and/or disorders.

Generally, the compounds of the invention have a cyclic acyloxyalkoxycarbonyl promoiety attached to the γ amino group of GABA analogs. The promoiety may be directly attached to the γ amino group of a GABA analog, or optionally, may be attached to the amino group of an α-amino acid promoiety, which may be acylated to the γ amino group of the GABA analog.

The compounds of the invention may also have a promoiety attached to the carboxyl group of GABA analogs. The carboxylpromoiety may be an ester or thioester group. A wide variety of ester or thioester groups may be used to form carboxyl promoieties.

The compounds of the invention may include as many as three promoieties, including one carboxylpromoiety and up to two promoieties attached in sequence to the γ amino group (i.e., such that each promoiety is sequentially cleaved from the N-terminal end of the GABA analog). The compounds of the invention will preferably, contain two amino promoieties and one carboxyl promoiety, two amino promoieties, one amino promoiety and one carboxylpromoiety or one amino promoiety. Preferably, in those compounds of the invention which contain both an amino promoiety and a carboxylpromoiety, the carboxylpromoiety is hydrolyzed prior to the complete cleavage of the promoiety (ies) attached to the amine group.

In a first aspect the present invention provides compounds of structural formula (I):

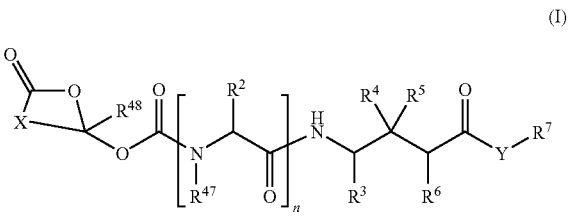

or a pharmaceutically acceptable salt, hydrate or solvate thereof, wherein:

n is 0 or 1;

Y is O or S;

X is alkyldiyl, substituted alkyldiyl, arylalkyldiyl, substituted arylalkyldiyl, aryldiyl, substituted aryldiyl, cycloheteroalkyldiyl, substituted cycloheteroalkyldiyl, heteroaryldiyl, substituted heteroaryldiyl, heteroarylalkyldiyl, substituted heteroarylalkyldiyl, heteroalkyldiyl or substituted heteroalkyldiyl;

$R^{47}$ is hydrogen, alkyl, substituted alkyl, arylalkyl or substituted arylalkyl;

$R^2$ is hydrogen, alkyl, substituted alkyl, alkoxy, substituted alkoxy, acyl, substituted acyl, acylamino, substituted acylamino, alkylamino, substituted alkylamino, alklysulfinyl, substituted alkylsulfinyl, alkylsulfonyl, substituted alkylsulfonyl, alkylthio, substituted alkylthio, alkoxycarbonyl, substituted alkylthio, aryl, substituted aryl, arylalkyl, substituted arylalkyl, aryloxy, substituted aryloxy, carbamoyl, substituted carbamoyl, cycloalkyl, substituted cycloalkyl, cycloheteroalkyl, substituted cycloheteroalkyl, dialkylamino, substituted dialkylamino, halo, heteroalkyl, substituted heteroalkyl, heteroaryl, substituted heteroaryl, heteroarylalkyl, substituted heteroarylalkyl, heteroalkyloxy, substituted heteroalkyloxy, heteroaryloxy, substituted heteroaryloxy, or optionally, $R^{47}$ and $R^2$ taken together are alkyldiyl or substituted alkyldiyl;

$R^3$ and $R^6$ are independently selected from the group consisting of hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroaryl, substituted heteroaryl, heteroarylalkyl and substituted heteroarylalkyl;

$R^4$ and $R^5$ are independently hydrogen, alkyl, substituted alkyl, acyl, substituted acyl, aryl, substituted aryl, arylalkyl, substituted arylalkyl, cycloalkyl, substituted cycloalkyl, cycloheteroalkyl, substituted cycloheteroalkyl, heteroaryl, substituted heteroaryl, heteroarylalkyl, substituted heteroarylalkyl or optionally, $R^4$ and $R^5$ taken together are alkyldiyl, substituted alkyldiyl, heteroalkyldiyl, substituted heteroalkyldiyl, or together with the carbon atom to which they are attached form a bridged cycloalkyl ring;

$R^7$ is hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl or substituted heteroarylalkyl; and $R^{48}$ is selected from the group consisting of hydrogen, alkyl, substituted alkyl, alkoxycarbonyl, substituted alkoxycarbonyl, aryl, substituted aryl, arylalkyl, substituted arylalkyl, carbamoyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl and substituted heteroarylalkyl.

In a second aspect, the present invention provides compositions of compounds of the invention. The compositions generally comprise one or more compounds of the invention, pharmaceutically acceptable salts, hydrates or solvates thereof and a pharmaceutically acceptable diluent, carrier, excipient and adjuvant. The choice of diluent, carrier, excipient and adjuvant will depend upon, among other factors, the desired mode of administration.

In a third aspect, the present invention provides methods for treating or preventing epilepsy, depression, anxiety, psychosis, faintness attacks, hypokinesia, cranial disorders, nuerodegenerative disorders, panic, pain (especially, neuropathic pain, post-herpetic pain, and muscular and skeletal pain), inflammatory disease i.e., arthritis), insomnia, gastrointestinal disorders or ethanol withdrawal syndrome. The methods generally involve administering to a patient in need of such treatment or prevention a therapeutically effective amount of a compound and/or composition of the invention.

In a fourth aspect, the current invention provides compositions for treating or preventing epilepsy, depression, anxiety, psychosis, faintness attacks, hypokinesia, cranial disorders, nuerodegenerative disorders, panic, pain (especially, neuropathic pain, post-herpetic pain, and muscular and skeletal pain), inflammatory disease (i.e., arthritis), insomnia, gastrointestinal disorders or ethanol withdrawal syndrome in a patient in need of such treatment or prevention.

4. DETAILED DESCRIPTION OF THE INVENTION

4.1 Definitions

"Compounds of the invention" refers to compounds encompassed by generic formulae disclosed herein and includes any specific compounds within that formula whose structure is disclosed herein. The compounds of the invention may be identified either by their chemical structure and/or chemical name. When the chemical structure and chemical name conflict, the chemical structure is determinative of the identity of the compound. The compounds of the invention may contain one or more chiral centers and/or double bonds and therefore, may exist as stereoisomers, such as double-bond isomers (i.e., geometric isomers), enantiomers or diastereomers. Accordingly, the chemical structures depicted herein encompass all possible enantiomers and stereoisomers of the illustrated compounds including the stereoisomerically pure form (e.g., geometrically pure, enantiomerically pure or diastereomerically pure) and enantiomeric and stereoisomeric mixtures. Enantiomeric and stereoisomeric mixtures can be resolved into their component enantiomers or stereoisomers using separation techniques or chiral synthesis techniques well known to the skilled artisan. The compounds of the invention may also exist in several tautomeric forms including the enol form, the keto form and mixtures thereof. Accordingly, the chemical structures depicted herein encompass all possible tautomeric forms of the illustrated compounds. The compounds of the invention also include isotopically labeled compounds where one or more atoms have an atomic mass different from the atomic mass conventionally found in nature. Examples of isotopes that may be incorporated into the compounds of the invention include, but are not limited to, $^2H$, $^3H$, $^3C$, $^{14}C$, $^{15}N$, $^{18}O$, $^{17}O$, $^{31}P$, $^{32}P$, $^{35}S$, $^{18}F$ and $^{36}Cl$. Further, it should be understood, when partial structures of the compounds of the invention are illustrated, that brackets indicate the point of attachment of the partial structure to the rest of the molecule.

"Composition of the invention" refers to at least one compound of the invention and a pharmaceutically acceptable vehicle, with which the compound is administered to a patient. When administered to a patient, the compounds of the invention are administered in isolated form, which means separated from a synthetic organic reaction mixture.

"Active transport or active transport process" refers to the movement of molecules across cellular membranes that:

a) is directly or indirectly dependent on an energy mediated process (i.e., driven by ATP hydrolysis, ion gradient, etc.); or b) occurs by facilitated diffusion mediated by interaction with specific transporter proteins.

"Transporter protein" refers to a protein that has a direct or indirect role in transporting a molecule into and/or through a cell. For example, transporter protein includes, but is not limited to, solute carrier transporters, co-transporters, counter transporters, uniporters, symporters, antiporters, pumps, equilibrative transporters, concentrative transporters and other proteins, which mediate active transport, energy-dependent transport, facilitated diffusion, exchange mechanisms and specific absorption mechanisms. Transporter protein, also includes but is not limited to, membrane-bound proteins that recognize a substrate and effect its entry into or exit from a cell by a carrier-mediated transporter or by receptor-mediated transport. Transporter protein, also includes but is not limited to, intracellularly expressed proteins that participate in trafficking of substrates through or out of a cell. Transporter protein, also includes but is not limited to, proteins or glycoproteins exposed on the surface of a cell that do not directly transport a substrate but bind to the substrate holding it in proximity to a receptor or transporter protein that effects entry of the substrate into or through the cell. Examples of carrier proteins include: the intestinal and liver bile acid transporters, dipeptide transporters, oligopeptide transporters, simple sugar transporters (e.g., SGLT1), phosphate transporters, monocarboxcylic acid transporters, P-glycoprotein transporters, organic anion transporters (OAT), and organic cation transporters. Examples of receptor-mediated transport proteins include: viral receptors, immunoglobulin receptors, bacterial toxin receptors, plant lectin receptors, bacterial adhesion receptors, vitamin transporters and cytokine growth factor receptors.

"Passive diffusion" refers to uptake of an agent that is not mediated by a specific transporter protein. An agent that is substantially incapable of passive diffusion has a permeabilty across a standard cell monolayer (e.g., Caco-2) in vitro of less than $5\times10^{-6}$ cm/sec, and usually less than $1\times10^{-6}$ cm/sec (in the absence of an efflux mechanism).

"Alkyl" refers to a saturated or unsaturated, branched, straight-chain or cyclic monovalent hydrocarbon radical derived by the removal of one hydrogen atom from a single carbon atom of a parent alkane, alkene or alkyne. Typical alkyl groups include, but are not limited to, methyl; ethyls such as ethanyl, ethenyl, ethynyl; propyls such as propan-1-yl, propan-2-yl, cyclopropan-1-yl, prop-1-en-1-yl, prop-1-en-2-yl, prop-2-en-1-yl (allyl), cycloprop-1-en-1-yl; cycloprop-2-en-1-yl, prop-1-yn-1-yl, prop-2-yn-1-yl, etc.; butyls such as butan-1-yl, butan-2-yl, 2-methyl-propan-1-yl, 2-methyl-propan-2-yl, cyclobutan-1-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, but-1-yn-1-yl, but-1-yn-3-yl, but-3-yn-1-yl, etc.; and the like.

The term "alkyl" is specifically intended to include groups having any degree or level of saturation, i.e., groups having exclusively single carbon-carbon bonds, groups having one or more double carbon-carbon bonds, groups having one or more triple carbon-carbon bonds and groups having mixtures of single, double and triple carbon-carbon bonds. Where a specific level of saturation is intended, the expressions "alkanyl," "alkenyl," and "alkynyl" are used. Preferably, an alkyl group comprises from 1 to 20 carbon atoms, more preferably, from 1 to 10 carbon atoms.

"Alkanyl" refers to a saturated branched, straight-chain or cyclic alkyl radical derived by the removal of one hydrogen atom from a single carbon atom of a parent alkane. Typical alkanyl groups include, but are not limited to, methanyl; ethanyl; propanyls such as propan-1-yl, propan-2-yl (isopropyl), cyclopropan-1-yl, etc.; butanyls such as butan-1-yl, butan-2-yl (sec-butyl), 2-methyl-propan-1-yl (isobutyl), 2-methyl-propan-2-yl (t-butyl), cyclobutan-1-yl, etc.; and the like.

"Alkenyl" refers to an unsaturated branched, straight-chain or cyclic alkyl radical having at least one carbon-carbon double bond derived by the removal of one hydrogen atom from a single carbon atom of a parent alkene. The group may be in either the cis or trans conformation about the double bond(s). Typical alkenyl groups include, but are not limited to, ethenyl; propenyls such as prop-1-en-1-yl, prop-1-en-2-yl, prop-2-en-1-yl (allyl), prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, etc.; and the like.

"Alkynyl" refers to an unsaturated branched, straight-chain or cyclic alkyl radical having at least one carbon-carbon triple bond derived by the removal of one hydrogen atom from a single carbon atom of a parent alkyne. Typical alkynyl groups include, but are not limited to, ethynyl; propynyls such as prop-1-yn-1-yl, prop-2-yn-1-yl, etc.; butynyls such as but-1-yn-1-yl, but-1-yn-3-yl, but-3-yn-1-yl, etc.; and the like.

"Alkyldiyl" refers to a saturated or unsaturated, branched, straight-chain or cyclic divalent hydrocarbon group derived by the removal of one hydrogen atom from each of two different carbon atoms of a parent alkane, alkene or alkyne, or by the removal of two hydrogen atoms from a single carbon atom of a parent alkane, alkene or alkyne. The two monovalent radical centers or each valency of the divalent radical center can form bonds with the same or different atoms. Typical alkyldiyl groups include, but are not limited to methandiyl; ethyldiyls such as ethan-1,1-diyl, ethan-1,2-diyl, ethen-1,1-diyl, ethen-1,2-diyl; propyldiyls such as propan-1,1-diyl, propan-1,2-diyl, propan-2,2-diyl, propan-1,3-diyl, cyclopropan-1,1-diyl, cyclopropan-1,2-diyl, prop-1-en-1,1-diyl, prop-1-en-1,2-diyl, prop-2-en-1,2-diyl, prop-1-en-1,3-diyl, cycloprop-1-en-1,2-diyl, cycloprop-2-en-1,2-diyl, cycloprop-2-en-1,1-diyl, prop-1-yn-1,3-diyl, etc.; butyldiyls such as, butan-1,1-diyl, butan-1,2-diyl, butan-1,3-diyl, butan-1,4-diyl, butan-2,2-diyl, 2-methyl-propan-1,1-diyl, 2-methyl-propan-1,2-diyl, cyclobutan-1,1-diyl; cyclobutan-1,2-diyl, cyclobutan-1,3-diyl, but-1-en-1,1-diyl, but-1-en-1,2-diyl, but-1-en-1,3-diyl, but-1-en-1,4-diyl, 2-methyl-prop-1-en-1,1-diyl, 2-methanylidene-propan-1,1-diyl, buta-1,3-dien-1,1-diyl, buta-1,3-dien-1,2-diyl, buta-1,3-dien-1,3-diyl, buta-1,3-dien-1,4-diyl, cyclobut-1-en-1,2-diyl, cyclobut-1-en-1,3-diyl, cyclobut-2-en-1,2-diyl, cyclobuta-1,3-dien-1,2-diyl, cyclobuta-1,3-dien-1,3-diyl, but-1-yn-1,3-diyl, but-1-yn-1,4-diyl, buta-1,3-diyn-1,4-diyl, etc.; and the like. Where specific levels of saturation are intended, the nomenclature alkanyldiyl, alkenyldiyl and/or alkynyldiyl is used. Preferably, an alkyldiyl group is $(C_1-C_{20})$ alkyldiyl, more preferably, $C_1-C_{20})$ alkyldiyl. Also preferred are saturated acyclic alkanyldiyl groups in which the radical centers are at the terminal carbons, e.g., methandiyl (methano); ethan-1,2-diyl (ethano); propan-1,3-diyl (propano); butan-1,4-diyl (butano); and the like (also referred to as alkylenos, defined infra).

"Alkyleno" refers to a straight-chain alkyldiyl group having two terminal monovalent radical centers derived by the removal of one hydrogen atom from each of the two terminal carbon atoms of straight-chain parent alkane, alkene or alkyne. Typical alkyleno groups include, but are not limited to, methano; ethylenos such as ethano, etheno, ethyno; propylenos such as propano, prop[1]eno, propa[1,2]dieno, prop[1]yno, etc.; butylenos such as butano, but[1]eno, but[2]eno, buta[1,3]dieno, but[1]yno, but[2]yno, but[1,3]diyno, etc.; and the like. Where specific levels of saturation are intended, the nomenclature alkano, alkeno and/or alkyno is used.

"Acyl" refers to a radical —C(O)R, where R is hydrogen, alkyl, cycloalkyl, cycloheteroalkyl, aryl, arylalkyl, heteroalkyl, heteroaryl, heteroarylalkyl as defined herein. Representative examples include, but are not limited to formyl, acetyl, cylcohexylcarbonyl, cyclohexylmethylcarbonyl, benzoyl, benzylcarbonyl and the like.

"Acylamino" (or alternatively "acylamido") refers to a radical —NR'C(O)R, where R' and R are each independently hydrogen, alkyl, cycloalkyl, cycloheteroalkyl, aryl, arylalkyl, heteroalkyl, heteroaryl, heteroarylalkyl, as defined herein. Representative examples include, but are not limited to, formylamino, acetylamino (i.e., acetamido), cyclohexylcarbonylamino, cyclohexylmethyl-carbonylamino, benzoylamino (i.e., benzamido), benzylcarbonylamino and the like.

"Acyloxy" refers to a radical —OC(O)R, where R is hydrogen, alkyl, cycloalkyl, cycloheteroalkyl, aryl, arylalkyl, heteroalkyl, heteroaryl or heteroarylalkyl, as defined herein. Representative examples include, but are not limited to, acetoxy, butoxy, benzoyloxy and the like.

"Alkylamino" means a radical —NHR where R represents an alkyl or cycloalkyl group as defined herein. Representative examples include, but are not limited to, methylamino, ethylamino, 1-methylethylamino, cyclohexyl amino and the like.

"Alkoxy" refers to a radical —OR where R represents an alkyl or cycloalkyl group as defined herein. Representative examples include, but are not limited to, methoxy, ethoxy, propoxy, butoxy, cyclohexyloxy and the like.

"Alkoxycarbonyl" refers to a radical —C(O)-alkoxy where alkoxy is as defined herein.

"Alkylsulfonyl" refers to a radical —S(O)$_2$R where R is an alkyl or cycloalkyl group as defined herein. Representative examples include, but are not limited to, methylsulfonyl, ethylsulfonyl, propylsulfonyl, butylsulfonyl and the like.

"Alkylsulfinyl" refers to a radical —S(O)R where R is an alkyl or cycloalkyl group as defined herein. Representative examples include, but are not limited to, methylsulfinyl, ethylsulfinyl, propylsulfinyl, butylsulfinyl and the like.

"Alkylthio" refers to a radical —SR where R is an alkyl or cycloalkyl group as defined herein that may be optionally substituted as defined herein. Representative examples include, but are not limited to methylthio, ethylthio, propylthio, butylthio and the like.

"Amino" refers to the radical —NH$_2$.

"Aryl" refers to a monovalent aromatic hydrocarbon group derived by the removal of one hydrogen atom from a single carbon atom of a parent aromatic ring system. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like. Preferably, an aryl group comprises from 5 to 20 carbon atoms, more preferably between 5 to 12 carbon atoms.

"Aryldiyl" refers to a divalent aromatic hydrocarbon group derived by the removal of one hydrogen atom from each of two different carbon atoms of a parent aromatic ring system or by the removal of two hydrogen atoms from a single carbon atom of a parent aromatic ring system. The two monovalent radical centers or each valency of the divalent center can form bonds with the same or different atom(s). Typical aryldiyl groups include, but are not limited to, divalent groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene, and the like. In preferred embodiments, the aryldiyl group is (C$_5$-C$_{20}$) aryldiyl, with (C$_5$-C$_{12}$) being even more preferred.

"Arylalkyl" refers to an acyclic alkyl group in which one of the hydrogen atoms bonded to a carbon atom, typically a terminal or sp$^3$ carbon atom, is replaced with an aryl group. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. Where specific alkyl moieties are intended, the nomenclature arylalkanyl, arylalkenyl and/or arylalkynyl is used. Preferably, an arylalkyl group is (C$_6$-C$_{30}$) arylalkyl, e.g., the alkanyl, alkenyl or alkynyl moiety of the arylalkyl group is (C$_1$-C$_{10}$) and the aryl moiety is (C$_5$-C$_{20}$), more preferably, an arylalkyl group is (C$_6$-C$_{20}$) arylalkyl, e.g., the alkanyl, alkenyl or alkynyl moiety of the arylalkyl group is (C$_1$-C$_8$) and the aryl moiety is (C$_5$-C$_{12}$).

"Arylalkyldiyl" refers to an arylalkyl group in which two of the arylalkyl group's hydrogen atoms have been replaced by covalent bonds. The two covalent bonds can be to the alkyl moiety of the arylalkyl group, as illustrated in the phenethylene group shown below:

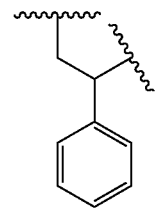

Alternatively, one of the covalent bonds can be to the alkyl moiety of the arylalkyl group and the other covalent bond can be to the aryl moiety of the arylalkyl group, as illustrated in the phenethylene group shown below:

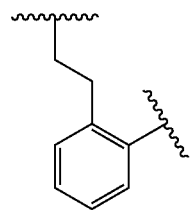

"Arylalkyloxy" refers to an —O-arylalkyl group where arylalkyl is as defined herein.

"Aryloxycarbonyl" refers to a radical —C(O)—O-aryl where aryl is as defined herein.

"Bridged cycloalkyl" refers to a radical selected from the group consisting of

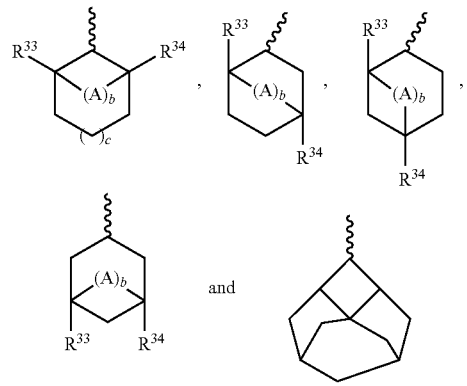

wherein:

A is (CR$^{35}$R$^{36}$)$_b$;

R$^{35}$ and R$^{36}$ are independently selected from the group consisting of hydrogen and methyl;

R$^{33}$ and R$^{34}$ are independently selected from the group consisting of hydrogen and methyl;

b is an integer from 1 to 4; and c is an integer from 0 to 2.

"Carbamoyl" refers to the radical —C(O)N(R)$_2$ where each R group is independently hydrogen, alkyl, cycloalkyl or aryl as defined herein, which may be optionally substituted, as defined herein.

"Carboxy" means the radical —C(O)OH.

"Cyano" means the radical —CN.

"Cycloalkyl" refers to a saturated or unsaturated cyclic alkyl radical. Where a specific level of saturation is intended, the nomenclature "cycloalkanyl" or "cycloalkenyl" is used. Typical cycloalkyl groups include, but are not limited to, groups derived from cyclopropane, cyclobutane, cyclopentane, cyclohexane, and the like. Preferably, the cycloalkyl group is (C$_3$-C$_{10}$) cycloalkyl, more preferably (C$_3$-C$_7$) cycloalkyl.

"Cycloheteroalkyl" refers to a saturated or unsaturated cyclic alkyl radical in which one or more carbon atoms (and any associated hydrogen atoms) are independently replaced with the same or different heteroatom. Typical heteroatoms to replace the carbon atom(s) include, but are not limited to, N, P, O, S, Si, etc. Where a specific level of saturation is intended, the nomenclature "cycloheteroalkanyl" or "cycloheteroalkenyl" is used. Typical cycloheteroalkyl groups include, but are not limited to, groups derived from epoxides, imidazolidine, morpholine, piperazine, piperidine, pyrazolidine, pyrrolidine, quinuclidine, and the like.

"Cycloheteroalkyldiyl" refers to a saturated or unsaturated cyclic alkyl diradical in which one or more carbon atoms (and any associated hydrogen atoms) are independently replaced with the same or different heteroatom. Typical heteroatoms to replace the carbon atom(s) include, but are not limited to, N, P, O, S, Si, etc. Where a specific level of saturation is intended, the nomenclature "cycloheteroalkanyldiyl" or "cycloheteroalkenyldiyl" is used.

"Cycloheteroalkyloxycarbonyl" refers to a radical —C(O)—OR where R is cycloheteroalkyl is as defined herein.

"Dialkylamino" means a radical —NRR' where R and R' independently represent an alkyl or cycloalkyl group as defined herein. Representative examples include, but are not limited to, dimethylamino, methylethylamino, di-(1-methylethyl)amino, (cyclohexyl)(methyl)amino, (cyclohexyl)(ethyl)amino, (cyclohexyl)(propyl)amino and the like.

"Halo" means fluoro, chloro, bromo, or iodo.

"Heteroalkyloxy" means an —O-heteroalkyl group where heteroalkyl is as defined herein.

"Heteroalkyl, Heteroalkanyl, Heteroalkenyl, Heteroalkynyl" refer to alkyl, alkanyl, alkenyl and alkynyl radical, respectively, in which one or more of the carbon atoms (and any associated hydrogen atoms) are each independently replaced with the same or different heteroatomic groups. Typical heteroatomic groups include, but are not limited to, —O—, —S—, —O—O—, —S—S—, —O—S—, —NR'—, =N—N=, —N=N—, —N=N—NR'—, —PH—, —P(O)$_2$—, —O—P(O)$_2$—, —S(O)—, —S(O)$_2$—, —SnH$_2$— and the like, where R' is hydrogen, alkyl, substituted alkyl, cycloalkyl, substituted cycloalkyl, aryl or substituted aryl.

"Heteroaryl" refers to a monovalent heteroaromatic radical derived by the removal of one hydrogen atom from a single atom of a parent heteroaromatic ring system. Typical heteroaryl groups include, but are not limited to, groups derived from acridine, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. Preferably, the heteroaryl group is between 5-20 membered heteroaryl, more preferably between 5-10 membered heteroaryl. Preferred heteroaryl groups include those derived from thiophene, pyrrole, benzothiophene, benzofuran, indole, pyridine, quinoline, imidazole, oxazole and pyrazine.

"Heteroaryldiyl" refers to a divalent heteroaromatic group derived by the removal of one hydrogen atom from each of two different atoms of a parent heteroaromatic ring system or by the removal of two hydrogen atoms from a single atom of a parent heteroaromatic ring system. The two monovalent radical centers or each valency of the single divalent center can form bonds with the same or different atom(s). Typical heteroaryldiyl groups include, but are not limited to, divalent groups derived from acridine, arsindole, carbazole, Ǝ-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. In preferred embodiments, the heteroaryldiyl group is 5-20 membered heteroaryldiyl, with 5-10 membered being particularly preferred. The most preferred heteroaryldiyl groups are divalent groups derived from the preferred heteroaryls thiophene, pyrrole, benzothiophene, benzofuran, indole, pyridine, quinoline, imidazole, oxazole and pyrazine.

"Heteroaryloxycarbonyl" refers to a radical —C(O)—OR where R is heteroaryl as defined herein.

"Heteroarylalkyl" refers to an acyclic alkyl group in which one of the hydrogen atoms bonded to a carbon atom, typically a terminal or sp$^3$ carbon atom, is replaced with a heteroaryl group. Where specific alkyl moieties are intended, the nomenclature heteroarylalkanyl, heteroarylalkenyl and/or heterorylalkynyl is used. In preferred embodiments, the heteroarylalkyl group is a 6-30 membered heteroarylalkyl, e.g., the alkanyl, alkenyl or alkynyl moiety of the heteroarylalkyl is 1-10 membered and the heteroaryl moiety is a 5-20-membered heteroaryl, more preferably, 6-20 membered heteroarylalkyl, e.g., the alkanyl, alkenyl or alkynyl moiety of the heteroarylalkyl is 1-8 membered and the heteroaryl moiety is a 5-12-membered heteroaryl.

"Heteroarylalkyldiyl" refers to an acyclic alkyl diradical in which one of the hydrogen atoms bonded to a carbon atom, typically a terminal or sp$^3$ carbon atom, is replaced with an heteroaryl group.

"Leaving group" has the meaning conventionally associated with it in synthetic organic chemistry, i.e., an atom or a group capable of being displaced by a nucleophile and includes halo (such as chloro, bromo and iodo), acyloxy (e.g., acetoxy), mesyloxy, tosyloxy, trifluoromethanesulfonyloxy, aryloxy (e.g., 2,4-dinitrophenoxy), methoxy, N,O-dimethylhydroxylamino and the like.

"Pharmaceutically acceptable" means approved by a regulatory agency of the Federal or a state government or listed in the U.S. Pharmacopeia or other generally recognized pharmacopeia for use in animals, and more particularly in humans.

"Pharmaceutically acceptable salt" refers to a salt of a compound of the invention that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, N-methylglucamine and the like.

"Pharmaceutically acceptable vehicle" refers to a diluent, adjuvant, excipient or carrier with which a compound of the invention is administered.

"Patient" is a mammal, e.g., a human, mouse, rat, guinea pig, dog, cat, horse, cow, pig, or non-human primate, such as a monkey, chimpanzee, baboon or rhesus.

"Preventing" or "prevention" refers to a reduction in risk of acquiring a disease or disorder (i.e., causing at least one of the clinical symptoms of the disease not to develop in a patient that may be exposed to or predisposed to the disease but does not yet experience or display symptoms of the disease).

"Prodrug" refers to a derivative of a drug molecule that requires a transformation within the body to release the active drug. Prodrugs are frequently (though not necessarily) pharmacologically inactive until converted to the parent drug. Typically, prodrugs are designed to overcome pharmaceutical and/or pharmacokinetically based problems associated with the parent drug molecule that would otherwise limit the clinical usefulness of the drug.

"Promoiety" refers to a form of protecting group that when used to mask a functional group within a drug molecule converts the drug into a prodrug. Typically, the promoiety will be attached to the drug via bond(s) that are cleaved by enzymatic or non-enzymatic means in vivo. Ideally, the promoiety is rapidly cleared from the body upon cleavage from the prodrug.

"Protecting group" refers to a grouping of atoms that when attached to a reactive group in a molecule masks, reduces or prevents that reactivity. Examples of protecting groups can be found in Green et al., "Protective Groups in Organic Chemistry", (Wiley, $2^{nd}$ ed. 1991) and Harrison et al., "Compendium of Synthetic Organic Methods", Vols. 1-8 (John Wiley and Sons, 1971-1996). Representative amino protecting groups include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethylsilylethanesulfonyl ("SES"), trityl and substituted trityl groups, allyloxycarbonyl, 9-fluorenylmethyloxycarbonyl ("FMOC"), nitro-veratryloxycarbonyl ("NVOC") and the like. Representative hydroxy protecting groups include, but are not limited to, those where the hydroxy group is either acylated or alkylated such as benzyl, and trityl ethers as well as alkyl ethers, tetrahydropyranyl ethers, trialkylsilyl ethers and allyl ethers.

"Substituted" refers to a group in which one or more hydrogen atoms are each independently replaced with the same or different substituent(s). Typical substituents include, but are not limited to, —X, —$R^{29}$, —$O^-$, =O, —$OR^{29}$, —$SR^{29}$, —$S^-$, =S, —$NR^{29}R^{30}$, =$NR^{29}$, —$CX_3$, —$CF_3$, —CN, —OCN, —SCN, —NO, —$NO_2$, =$N_2$, —$N_3$, —$S(O)_2O^-$, —$S(O)_2OH$, —$S(O)_2R^{29}$, —$OS(O_2)O^-$, —$OS(O)_2R^{29}$, —$P(O)(O^-)_2$, —$P(O)(OR^{29})(O^-)$, —$OP(O)(OR^{29})(OR^{30})$, —$C(O)R^{29}$, —$C(S)R^{29}$, —$C(O)OR^{29}$, —$C(O)NR^{29}R^{30}$, —$C(O)O^-$, —$C(S)OR^{29}$, —$NR^{31}C(O)NR^{29}R^{30}$, —$NR^{31}C(S)NR^{29}R^{30}$, —$NR^{31}C(NR^{29})NR^{29}R^{30}$ and —$C(NR^{29})NR^{29}R^{30}$, where each X is independently a halogen; each $R^{29}$ and $R^{30}$ are independently hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, cycloheteroalkyldiyl, substituted cycloheteroalkyldiyl, heteroalkyl, substituted heteroalkyl, heteroaryl, substituted heteroaryl, heteroarylalkyl, substituted heteroarylalkyl, —$NR^{31}R^{32}$, —$C(O)R^{31}$ or —$S(O)_2R^{31}$ or optionally $R^{29}$ and $R^{30}$ together with the atom to which they are both attached form a cycloheteroalkyl or substituted cycloheteroalkyl ring; and $R^{31}$ and $R^{32}$ are independently hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl or substituted heteroarylalkyl.

"Treating" or "treatment" of any disease or disorder refers, in one embodiment, to ameliorating the disease or disorder (i.e., arresting or reducing the development of the disease or at least one of the clinical symptoms thereof). In another embodiment "treating" or "treatment" refers to ameliorating at least one physical parameter, which may not be discernible by the patient. In yet another embodiment, "treating" or "treatment" refers to inhibiting the disease or disorder, either physically, (e.g., stabilization of a discernible symptom), physiologically, (e.g., stabilization of a physical parameter), or both. In yet another embodiment, "treating" or "treatment" refers to delaying the onset of the disease or disorder.

"Therapeutically effective amount" means the amount of a compound that, when administered to a patient for treating a disease, is sufficient to effect such treatment for the disease. The "therapeutically effective amount" will vary depending on the compound, the disease and its severity and the age, weight, etc., of the patient to be treated.

Reference will now be made in detail to preferred embodiments of the invention. While the invention will be described in conjunction with the preferred embodiments, it will be understood that it is not intended to limit the invention to those preferred embodiments. To the contrary, it is intended to cover alternatives, modifications, and equivalents as may be included within the spirit and scope of the invention as defined by the appended claims.

4.2 The Compounds of the Invention

Those of skill in the art will appreciate that compounds of Formulae (I)-(X), below, share certain structural features in common. These compounds are all GABA analogs (i.e., γ-aminobutyric acid derivatives) to which promoieties have been attached. In particular, $R^2$, $R^3$, $R^4$, $R^5$, $R^6$, $R^7$, $R^{47}$, $R^{48}$ and Y are common substituents found in compounds of Formulae (I)-(X).

The compounds of the invention include compounds of structural Formula (I):

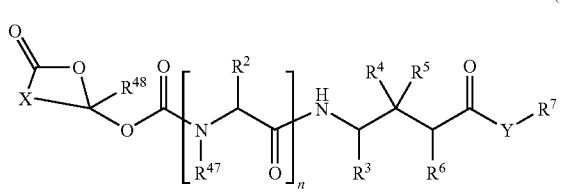

or a pharmaceutically acceptable salt, hydrate or solvate thereof, wherein:

n is 0 or 1;

Y is O or S;

X is alkyldiyl, substituted alkyldiyl, arylalkyldiyl, substituted arylalkyldiyl, aryldiyl, substituted aryldiyl, cycloheteroalkyldiyl, substituted cycloheteroalkyldiyl, heteroaryldiyl, substituted heteroaryldiyl, heteroarylalkyldiyl, substituted heteroarylalkyldiyl, heteroalkyldiyl or substituted heteroalkyldiyl;

$R^{47}$ is hydrogen, alkyl, substituted alkyl, arylalkyl or substituted arylalkyl;

$R^2$ is hydrogen, alkyl, substituted alkyl, alkoxy, substituted alkoxy, acyl, substituted acyl, acylamino, substituted acylamino, alkylamino, substituted alkylamino, alklysulfinyl, substituted alkylsulfinyl, alkylsulfonyl, substituted alkylsulfonyl, alkylthio, substituted alkylthio, alkoxycarbonyl, substituted alkylthio, aryl, substituted aryl, arylalkyl, substituted arylalkyl, aryloxy, substituted aryloxy, carbamoyl, substituted carbamoyl, cycloalkyl, substituted cycloalkyl, cycloheteroalkyl, substituted cycloheteroalkyl, dialkylamino, substituted dialkylamino. halo. heteroalkyl, substituted heteroalkyl, heteroaryl, substituted heteroaryl, heteroarylalkyl, substituted heteroarylalkyl, heteroalkyloxy, substituted heteroalkyloxy, heteroaryloxy, substituted heteroaryloxy, or optionally, $R^{47}$ and $R^2$ taken together are alkyldiyl or substituted alkyldiyl;

$R^3$ and $R^6$ are independently selected from the group consisting of hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroaryl, substituted heteroaryl, heteroarylalkyl and substituted heteroarylalkyl;

$R^4$ and $R^5$ are independently hydrogen, alkyl, substituted alkyl, acyl, substituted acyl, aryl, substituted aryl, arylalkyl, substituted arylalkyl, cycloalkyl, substituted cycloalkyl, cycloheteroalkyl, substituted cycloheteroalkyl, heteroaryl, substituted heteroaryl, heteroarylalkyl, substituted heteroarylalkyl or optionally, $R^4$ and $R^5$ taken together are alkyldiyl, substituted alkyldiyl, heteroalkyldiyl, substituted heteroalkyldiyl, or together with the carbon atom to which they are attached form a bridged cycloalkyl ring;

$R^7$ is hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl or substituted heteroarylalkyl; and $R^{48}$ is selected from the group consisting of hydrogen, alkyl, substituted alkyl, alkoxycarbonyl, substituted alkoxycarbonyl, aryl, substituted aryl, arylalkyl, substituted arylalkyl, carbamoyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl and substituted heteroarylalkyl.

Preferably, X is alkyldiyl, substituted alkyldiyl, aryldiyl, substituted aryldiyl, cycloheteroalkyldiyl, substituted cycloheteroalkyldiyl, heteroaryldiyl, substituted heteroaryldiyl, heteroalkyldiyl or substituted heteroalkyldiyl. More preferably, X is alkyldiyl, substituted alkyldiyl, cycloheteroalkyldiyl, substituted cycloheteroalkyldiyl, heteroaryldiyl, heteroalkyldiyl or substituted heteroalkyldiyl. Even more preferably, X is alkyldiyl or substituted alkyldiyl. Most preferably, X is alkyleno or substituted alkyleno.

Illustrative embodiments of Formula (I) include Compound 44, Compound 47, and Compound 53 as set forth below:

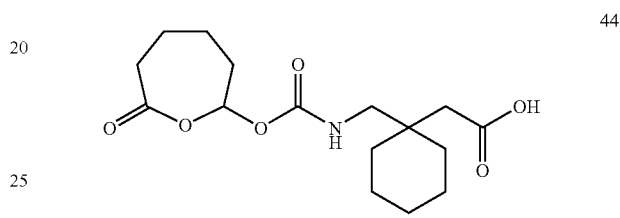

44

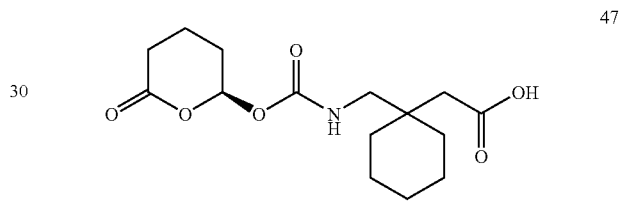

47

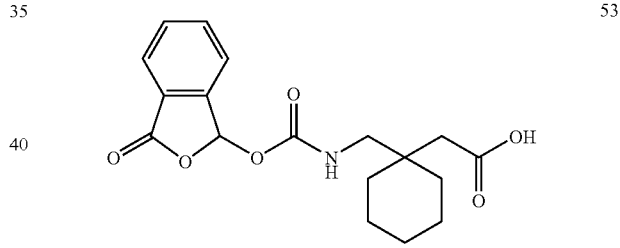

53

Preferred embodiments of compounds of Formula (I) include compounds of Formula (II-X):

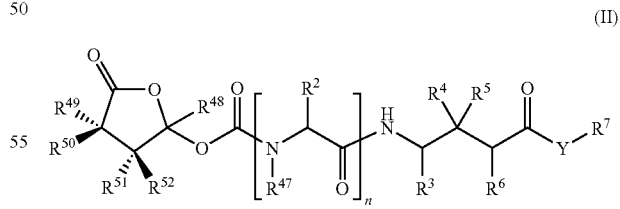

(II)

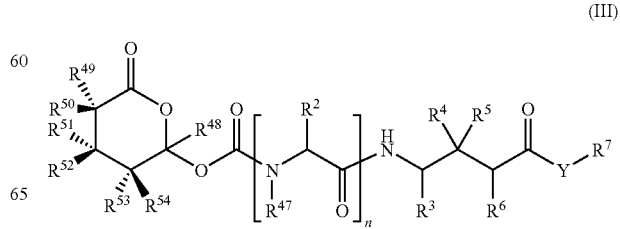

(III)

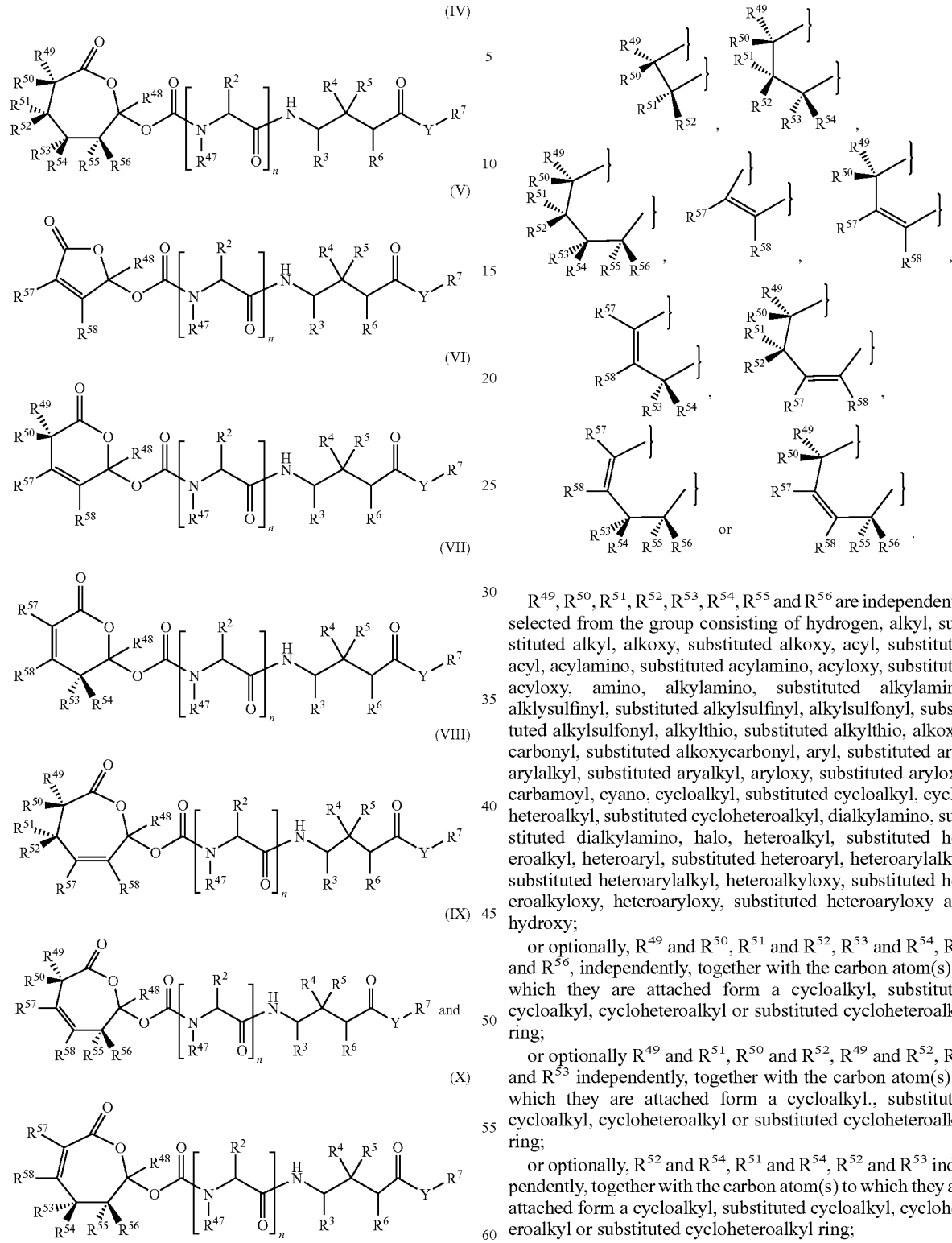

In Formula (II) to Formula (X) above, n, Y, $R^{47}$, $R^2$, $R^3$, $R^6$, $R^4$, $R^5$, $R^7$ and $R^{48}$ are as previously defined. Those of skill in the art will appreciate that in Formulae (II) through (X) that X has been replaced by the respective diyl fragment shown below:

$R^{49}$, $R^{50}$, $R^{51}$, $R^{52}$, $R^{53}$, $R^{54}$, $R^{55}$ and $R^{56}$ are independently selected from the group consisting of hydrogen, alkyl, substituted alkyl, alkoxy, substituted alkoxy, acyl, substituted acyl, acylamino, substituted acylamino, acyloxy, substituted acyloxy, amino, alkylamino, substituted alkylamino, alklysulfinyl, substituted alkylsulfinyl, alkylsulfonyl, substituted alkylsulfonyl, alkylthio, substituted alkylthio, alkoxycarbonyl, substituted alkoxycarbonyl, aryl, substituted aryl, arylalkyl, substituted aryalkyl, aryloxy, substituted aryloxy, carbamoyl, cyano, cycloalkyl, substituted cycloalkyl, cycloheteroalkyl, substituted cycloheteroalkyl, dialkylamino, substituted dialkylamino, halo, heteroalkyl, substituted heteroalkyl, heteroaryl, substituted heteroaryl, heteroarylalkyl, substituted heteroarylalkyl, heteroalkyloxy, substituted heteroalkyloxy, heteroaryloxy, substituted heteroaryloxy and hydroxy;

or optionally, $R^{49}$ and $R^{50}$, $R^{51}$ and $R^{52}$, $R^{53}$ and $R^{54}$, $R^{55}$ and $R^{56}$, independently, together with the carbon atom(s) to which they are attached form a cycloalkyl, substituted cycloalkyl, cycloheteroalkyl or substituted cycloheteroalkyl ring;

or optionally $R^{49}$ and $R^{51}$, $R^{50}$ and $R^{52}$, $R^{49}$ and $R^{52}$, $R^{51}$ and $R^{53}$ independently, together with the carbon atom(s) to which they are attached form a cycloalkyl., substituted cycloalkyl, cycloheteroalkyl or substituted cycloheteroalkyl ring;

or optionally, $R^{52}$ and $R^{54}$, $R^{51}$ and $R^{54}$, $R^{52}$ and $R^{53}$ independently, together with the carbon atom(s) to which they are attached form a cycloalkyl, substituted cycloalkyl, cycloheteroalkyl or substituted cycloheteroalkyl ring;

or optionally, $R^{53}$ and $R^{55}$, $R^{54}$ and $R^{56}$, $R^{53}$ and $R^{56}$ and $R^{54}$ and $R^{55}$ independently, together with the carbon atom(s) to which they are attached form a cycloalkyl, substituted cycloalkyl, cycloheteroalkyl or substituted cycloheteroalkyl ring;

$R^{57}$ and $R^{58}$ are independently selected from the group consisting of hydrogen, alkyl, substituted alkyl, acylamino, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl and substituted heteroarylalkyl;

or optionally $R^{57}$ and $R^{58}$ together with the carbon atoms to which they are attached form an aryl, substituted aryl, heteroaryl, substituted heteroaryl, cycloalkyl, substituted cycloalkyl, cycloheteroalkyl or substituted cycloheteroalkyl ring.

In one embodiment of compounds of Formulae (I)-(X), n is 0. In another embodiment, n is 1. When n is 1, preferably the α-amino acid is of the L-stereochemical configuration or is glycine.

In an embodiment of compounds of Formulae (I)-(X), $R^7$ is selected from the group consisting of hydrogen, alkyl, substituted alkyl, aryl, substituted aryl, arylalkanyl, substituted arylalkanyl, cycloalkanyl, substituted cycloalkanyl, cycloheteroalkanyl and substituted cycloheteroalkanyl. In another embodiment, Y is O and $R^7$ is hydrogen. In still another embodiment, Y is O and $R^7$ is alkanyl, substituted alkanyl, alkenyl, substituted alkenyl, aryl or substituted aryl. Preferably, $R^7$ is —C(CH$_3$)═CH$_2$, —CH$_2$C(O)N(CH$_3$)$_2$, —CH$_2$C(O)N(CH$_2$CH$_3$)$_2$, or

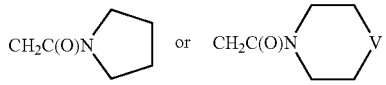

where V is O or CH$_2$.

In an embodiment of compounds of Formulae (I)-(X), $R^{47}$ is H and $R^2$ is hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl or substituted heteroarylalkyl. Preferably, $R^2$ is selected from the group consisting of hydrogen, alkanyl, substituted alkanyl, aryl, substituted aryl, arylalkanyl, substituted arylalkanyl, cycloalkanyl, heteroarylalkanyl and substituted heteroarylalkanyl.

In another embodiment, $R^{47}$ is H and $R^2$ is hydrogen, cycloalkanyl or alkanyl. Preferably, $R^2$ is hydrogen, methyl, 2-propyl, 2-butyl, isobutyl, t-butyl, cyclopentyl or cyclohexyl.

In still another embodiment, $R^{47}$ is H and $R^2$ is substituted alkanyl. Preferably, $R^2$ is —CH$_2$OH, —CH(OH)CH$_3$, —CH$_2$CO$_2$H, —CH$_2$CH$_2$CO$_2$H, —CH$_2$CONH$_2$, —CH$_2$CH$_2$CONH$_2$, —CH$_2$CH$_2$SCH$_3$, —CH$_2$SH, —CH$_2$(CH$_2$)$_3$NH$_2$ or —CH$_2$CH$_2$CH$_2$NHC(NH)NH$_2$.

In still another embodiment, $R^{47}$ is H and $R^2$ is selected from the group consisting of aryl, arylalkanyl, substituted arylalkanyl and heteroarylalkanyl. Preferably, $R^2$ is phenyl, benzyl, 4-hydroxybenzyl, 2-imidazolyl or 2-indolyl.

In yet another embodiment, $R^{47}$ and $R^2$ together with the atoms to which they are attached form a cycloheteroalkyl or substituted cycloheteroalkyl ring. Preferably $R^{47}$ and $R^2$ together with the atoms to which they are attached form an azetidine, pyrrolidine or piperidine ring.

In another embodiment of compounds of Formulae (I)-(X), $R^3$ is hydrogen. In still another embodiment, $R^6$ is hydrogen. In yet another embodiment, $R^3$ and $R^6$ are independently selected from the group consisting of hydrogen, alkyl, substituted alkyl, aryl, substituted aryl, cycloalkyl and substituted cycloalkyl. Preferably, $R^3$ and $R^6$ are independently selected from the group consisting of hydrogen and alkanyl. More preferably, $R^3$ is hydrogen or alkanyl and $R^6$ is hydrogen.

In still another embodiment of compounds of Formulae (I)-(X), $R^4$ and $R^5$ are independently selected from the group consisting of hydrogen, alkyl, substituted alkyl, aryl, substituted aryl, cycloalkyl, substituted cycloalkyl, cycloheteroalkyl, substituted cycloheteroalkyl, heteroaryl and substituted heteroaryl. Preferably, $R^4$ and $R^5$ are independently selected from the group consisting of hydrogen, alkanyl and substituted alkanyl.

In still another embodiment of compounds of Formulae (I)-(X), $R^4$ and $R^5$ together with the carbon atom to which they are attached are cycloalkanyl or substituted cycloalkanyl. Preferably, $R^4$ and $R^5$ together with the carbon atom to which they are attached are cyclobutyl, substituted cyclobutyl, cyclopentyl, substituted cyclopentyl, cyclohexyl or substituted cyclohexyl. In another embodiment, $R^4$ and $R^5$ together with the carbon atom to which they are attached are cycloheteroalkyl or substituted cycloheteroalkyl. In still another embodiment, $R^4$ and $R^5$ together with the carbon atom to which they are attached are bridged cycloalkyl.

In still another embodiment of compounds of Formulae (I)-(X), $R^{48}$ is selected from the group consisting of hydrogen, alkyl, substituted alkyl, alkoxycarbonyl, substituted alkoxycarbonyl, aryl, substituted aryl, arylalkyl, substituted arylalkyl, carbamoyl, cycloalkyl, substituted cycloalkyl, heteroaryl and substituted heteroaryl. Preferably $R^{48}$ is hydrogen, methyl, ethyl, isopropyl, methoxycarbonyl, ethoxycarbonyl, isopropoxycarbonyl or phenyl. More preferably $R^{48}$ is hydrogen.

In still another embodiment of compounds of Formulae (I)-(X), $R^{49}$, $R^{50}$, $R^{51}$, $R^{52}$, $R^{53}$, $R^{54}$, $R^{55}$ and $R^{56}$ are independently selected from the group consisting of hydrogen, alkyl, substituted alkyl, alkoxy, acyl, substituted acyl, acylamino, acyloxy, amino, alkylamino, alkoxycarbonyl, aryl, substituted aryl, arylalkyl, carbamoyl, cycloalkyl, substituted cycloalkyl, cycloheteroalkyl, substituted cycloheteroalkyl, dialkylamino, halo, heteroalkyl, heteroaryl and hydroxy. Preferably, $R^{49}$, $R^{50}$, $R^{51}$, $R^{52}$, $R^{53}$, $R^{54}$, $R^{55}$ and $R^{56}$ are independently hydrogen, methyl, ethyl, phenyl, methoxy, ethoxy, amino, acetamido, benzamido, acetoxy, benzoyloxy or hydroxy.

In a preferred embodiment, $R^{49}$ and $R^{50}$ are independently hydrogen, methyl, ethyl, phenyl, methoxy, ethoxy, amino, acetamido, benzamido, acetoxy, benzoyloxy or hydroxy and $R^{51}$, $R^{52}$, $R^{53}$, $R^{54}$, $R^{55}$ and $R^{56}$ are hydrogen. In another preferred embodiment, $R^{49}$ is hydrogen, methyl, ethyl, phenyl, methoxy, ethoxy, amino, acetamido, benzamido, acetoxy, benzoyloxy or hydroxy and $R^{50}$, $R^{51}$, $R^{52}$, $R^{53}$, $R^{54}$, $R^{55}$ and $R^{56}$ are hydrogen. In still another preferred embodiment, $R^{50}$ is hydrogen, methyl, ethyl, phenyl, methoxy, ethoxy, amino, acetamido, benzamido, acetoxy, benzoyloxy or hydroxy and $R^{49}$, $R^{51}$, $R^{52}$, $R^{53}$, $R^{54}$, $R^{55}$ and $R^{56}$ are hydrogen. In another preferred embodiment, $R^{49}$, $R^{50}$, $R^{51}$, $R^{52}$, $R^{53}$, $R^{54}$, $R^{55}$ and $R^{56}$ are hydrogen.

In one embodiment of compounds of Formulae (I), (II), (III) (IV) and (VIII), $R^{49}$ and $R^{51}$ together with the carbon atoms to which they are attached form a cycloalkyl, substituted cycloalkyl, cycloheteroalkyl or substituted cycloheteroalkyl ring. Preferably $R^{49}$ and $R^{51}$ together with the carbon atoms to which they are attached form a cyclobutyl, cyclopentyl, cyclohexyl or a 2,2-disubstituted 1,3-dioxolane ring.

In one embodiment of compounds of Formulae (I), (II), (III) (IV) and (VIII), $R^{50}$ and $R^{52}$ together with the carbon atoms to which they are attached form a cycloalkyl, substituted cycloalkyl, cycloheteroalkyl or substituted cycloheteroalkyl ring. Preferably $R^{50}$ and $R^{52}$ together with the carbon atoms to which they are attached form a cyclobutyl, cyclopentyl, cyclohexyl or a 2,2-disubstituted 1,3-dioxolane ring.

In another embodiment of compounds of Formulae (I), (II), (III) (IV) and (VIII), $R^{50}$ and $R^{51}$ together with the carbon atoms to which they are attached form a cycloalkyl, substituted cycloalkyl, cycloheteroalkyl or substituted cycloheteroalkyl ring. Preferably, $R^{50}$ and $R^{51}$ together with the carbon atoms to which they are attached form a cyclobutyl, cyclopentyl, cyclohexyl or a 2,2-disubstituted 1,3-dioxolane ring.

In still another embodiment of compounds of Formulae (I), (II), (III) (IV) and (VIII), $R^{49}$ and $R^{52}$ together with the carbon atoms to which they are attached form a cycloalkyl, substituted cycloalkyl, cycloheteroalkyl or substituted cycloheteroalkyl ring. Preferably, $R^{49}$ and $R^{52}$ together with the carbon atoms to which they are attached form a cyclobutyl, cyclopentyl, cyclohexyl or a 2,2-disubstituted 1,3-dioxolane ring.

In one embodiment of compounds of Formulae (III) and (IV), $R^{51}$ and $R^{53}$ together with the carbon atoms to which they are attached form a cycloalkyl, substituted cycloalkyl, cycloheteroalkyl or substituted cycloheteroalkyl ring. Preferably, $R^{51}$ and $R^{53}$ together with the carbon atoms to which they are attached form a cyclobutyl, cyclopentyl, cyclohexyl or a 2,2-disubstituted 1,3-dioxolane ring.

In another embodiment of compounds of Formulae (III) and (IV), $R^{52}$ and $R^{54}$ together with the carbon atoms to which they are attached form a cycloalkyl, substituted cycloalkyl, cycloheteroalkyl or substituted cycloheteroalkyl ring. Preferably, $R^{52}$ and $R^{54}$ together with the carbon atoms to which they are attached form a cyclobutyl, cyclopentyl, cyclohexyl or a 2,2-disubstituted 1,3-dioxolane ring.

In still another embodiment of compounds of Formulae (III) and (IV), $R^{52}$ and $R^{53}$ together with the carbon atoms to which they are attached form a cycloalkyl, substituted cycloalkyl, cycloheteroalkyl or substituted cycloheteroalkyl ring. Preferably, $R^{52}$ and $R^{53}$ together with the carbon atoms to which they are attached form a cyclobutyl, cyclopentyl, cyclohexyl or a 2,2-disubstituted 1,3-dioxolane ring.

In still another embodiment of compounds of Formulae (III) and (IV), $R^{51}$ and $R^{54}$ together with the carbon atoms to which they are attached form a cycloalkyl, substituted cycloalkyl, cycloheteroalkyl or substituted cycloheteroalkyl ring. Preferably, $R^{51}$ and $R^{54}$ together with the carbon atoms to which they are attached form a cyclobutyl, cyclopentyl, cyclohexyl or a 2,2-disubstituted 1,3-dioxolane ring.

In one embodiment of compounds of Formulae (IV) and (X), $R^{53}$ and $R^{55}$ together with the carbon atoms to which they are attached form a cycloalkyl, substituted cycloalkyl, cycloheteroalkyl or substituted cycloheteroalkyl ring. Preferably, $R^{53}$ and $R^{55}$ together with the carbon atoms to which they are attached form a cyclobutyl, cyclopentyl, cyclohexyl or a 2,2-disubstituted 1,3-dioxolane ring.

In another embodiment of compounds of Formulae (IV) and (X), $R^{54}$ and $R^{56}$ together with the carbon atoms to which they are attached form a cycloalkyl, substituted cycloalkyl, cycloheteroalkyl or substituted cycloheteroalkyl ring. Preferably, $R^{54}$ and $R^{56}$ together with the carbon atoms to which they are attached form a cyclobutyl, cyclopentyl, cyclohexyl or a 2,2-disubstituted 1,3-dioxolane ring.

In still another embodiment of compounds of Formulae (IV) and (X), $R^{53}$ and $R^{56}$ together with the carbon atoms to which they are attached form a cycloalkyl, substituted cycloalkyl, cycloheteroalkyl or substituted cycloheteroalkyl ring. Preferably, $R^{53}$ and $R^{56}$ together with the carbon atoms to which they are attached form a cyclobutyl, cyclopentyl, cyclohexyl or a 2,2-disubstituted 1,3-dioxolane ring.

In still another embodiment of compounds of Formulae (IV) and (X), $R^{54}$ and $R^{55}$ together with the carbon atoms to which they are attached form a cycloalkyl, substituted cycloalkyl, cycloheteroalkyl or substituted cycloheteroalkyl ring. Preferably, $R^{54}$ and $R^{55}$ together with the carbon atoms to which they are attached form a cyclobutyl, cyclopentyl, cyclohexyl or a 2,2-disubstituted 1,3-dioxolane ring.

In one embodiment of compounds of Formulae (V)-(X), $R^{57}$ and $R^{58}$ are independently hydrogen, alkyl, substituted alkyl, acylamino, aryl, substituted aryl, arylalkyl, cycloalkyl, cycloheteroalkyl, heteroalkyl, substituted heteroalkyl, heteroaryl or substituted heteroaryl. Preferably, $R^{57}$ and $R^{58}$ are independently hydrogen, methyl, ethyl or phenyl. Preferably $R^{57}$ is hydrogen, methyl, ethyl or phenyl and $R^{58}$ is hydrogen or methyl. Preferably $R^{58}$ is hydrogen, methyl, ethyl or phenyl and $R^{57}$ is hydrogen or methyl.

In another embodiment of compounds of Formulae (V)-(X), $R^{57}$ and $R^{58}$ together with the carbon atoms to which they are attached form an aryl, substituted aryl, heteroaryl, substituted heteroaryl, cycloalkyl or substituted cycloalkyl ring. Preferably $R^{57}$ and $R^{58}$ together with the carbon atoms to which they are attached form a cyclopentenyl, cyclohexenyl, phenyl, furyl, thienyl, pyrrolyl, benzothienyl, benzofuryl, indolyl, pyridyl, quinolyl, imidazolyl or oxazolyl ring. More preferably $R^{57}$ and $R^{58}$ together with the carbon atoms to which they are attached form a phenyl ring.

In another embodiment of compounds of Formulae (I)-(X), Y is O, $R^3$, $R^6$ and $R^7$ are hydrogen and $R^4$ and $R^5$ together with the carbon atom to which they are attached form a cycloalkyl, substituted cycloalkyl, cycloheteroalkyl, substituted cycloheteroalkyl, bridged cycloalkyl or substituted bridged cycloalkyl ring.

In a preferred embodiment, $R^4$ and $R^5$ together with the carbon atom to which they are attached form a cycloalkyl or substituted cycloalkyl ring. Preferably, n is 0. Preferably, n is 1, $R^{47}$ is hydrogen, and $R^2$ is hydrogen, methyl, 2-propyl, 2-butyl, isobutyl, t-butyl, cyclopentyl, cyclohexyl, phenyl, benzyl, 4-hydroxybenzyl, 2-imidazolyl, 2-indolyl, —CH$_2$OH, —CH(OH)CH$_3$, —CH$_2$CO$_2$H, —CH$_2$CH$_2$CO$_2$H, —CH$_2$CONH$_2$, —CH$_2$CH$_2$CONH$_2$, —CH$_2$CH$_2$SCH$_3$, —CH$_2$SH, —CH$_2$(CH$_2$)$_3$NH$_2$ or —CH$_2$CH$_2$CH$_2$NHC(NH)NH$_2$. Preferably, n is 1 and $R^{47}$ and $R^2$ together with the atoms to which they are attached form a pyrrolidine ring.

In another preferred embodiment, $R^4$ and $R^5$ together with the carbon atom to which they are attached form a cyclobutyl or substituted cyclobutyl ring. Preferably, the substituted cyclobutyl ring is substituted with one or more substituents selected from the group consisting of alkanyl, substituted alkanyl, halo, hydroxy, carboxy and alkoxycarbonyl.

In still another preferred embodiment, $R^4$ and $R^5$ together with the carbon atom to which they are attached form a cyclopentyl or substituted cyclopentyl ring. Preferably, the cyclopentyl ring is substituted with one or more substituents selected from the group consisting of alkanyl, substituted alkanyl, halo, hydroxy, carboxy or alkoxycarbonyl. More preferably, the cyclopentyl ring is substituted with alkanyl. Even more preferably, the cyclopentyl ring is selected from the group consisting of

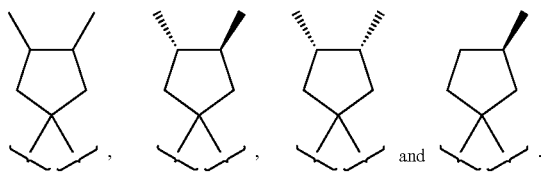

Preferably, in this embodiment, R$^7$ is hydrogen.

In still another embodiment, R$^4$ and R$^5$ together with the carbon atom to which they are attached form a cyclohexyl or substituted cyclohexyl ring. Preferably, the cyclohexyl ring is substituted with one or more substituents selected from the group consisting of alkanyl, substituted alkanyl, halo, hydroxy, carboxy or alkoxycarbonyl. More preferably, the cyclohexyl ring is substituted with alkanyl. Even more preferably, the cyclohexyl ring is selected from the group consisting of

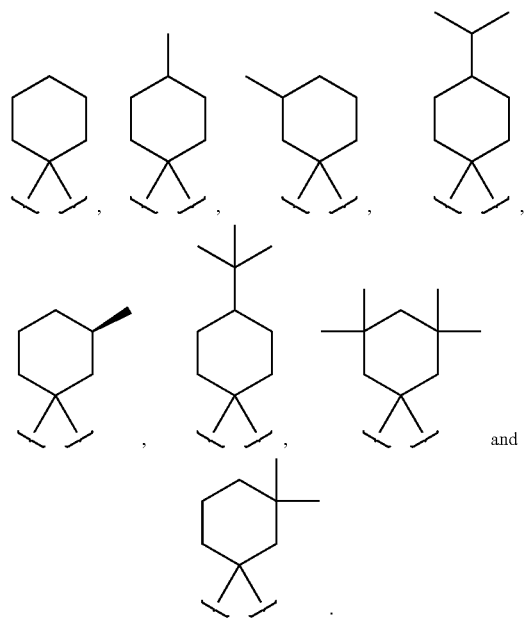

Preferably, in this embodiment, R$^7$ is hydrogen.

In still another embodiment of compounds of Formulae (I)-(X), R$^4$ and R$^5$ together with the carbon atom to which they are attached form a cycloheteroalkyl or substituted cycloheteroalkyl ring. In one embodiment, n is 0. In another embodiment, n is 1, R$^{47}$ is hydrogen, and R$^2$ is hydrogen, methyl, 2-propyl, 2-butyl, isobutyl, t-butyl, cyclopentyl, cyclohexyl, phenyl, benzyl, 4-hydroxybenzyl, 2-imidazolyl, 2-indolyl, —CH$_2$OH, —CH(OH)CH$_3$, —CH$_2$CO$_2$H, —CH$_2$CH$_2$CO$_2$H, —CH$_2$CONH$_2$, —CH$_2$CH$_2$CONH$_2$, —CH$_2$CH$_2$SCH$_3$, —CH$_2$SH, —CH$_2$(CH$_2$)$_3$NH$_2$ or —CH$_2$CH$_2$CH$_2$NHC(NH)NH$_2$. In still another embodiment, n is 1 and R$^{47}$ and R$^2$ together with the atoms to which they are attached form a pyrrolidine ring.

Preferably, R$^4$ and R$^5$ together with the carbon atom to which they are attached form a cycloheteroalkanyl ring. More preferably, the cycloheteroalkanyl ring is selected from the group consisting of

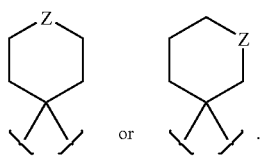

wherein Z is O, S(O)$_p$ or NR$^{18}$;
p is 0, 1 or 2; and
R$^{18}$ is selected from the group consisting of hydrogen, alkyl, substituted alkyl, acyl and alkoxycarbonyl.

More preferably, the cycloheteroalkanyl ring is selected from the group consisting of

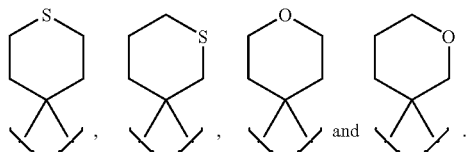

Preferably, in this embodiment, R$^7$ is hydrogen.

In still another embodiment of compounds of Formulae (I)-(X), R$^4$ and R$^5$ together with the carbon atom to which they are attached form a bridged cycloalkyl ring. In one embodiment, n is 0. In another embodiment, n is 1, R$^{47}$ is hydrogen, and R$^2$ is hydrogen, methyl, 2-propyl, 2-butyl, isobutyl, t-butyl, cyclopentyl, cyclohexyl, phenyl, benzyl, 4-hydroxybenzyl, 2-imidazolyl, 2-indolyl, —CH$_2$OH, —CH(OH)CH$_3$, —CH$_2$CO$_2$H, —CH$_2$CH$_2$CO$_2$H, —CH$_2$CONH$_2$, —CH$_2$CH$_2$CONH$_2$, —CH$_2$CH$_2$SCH$_3$, —CH$_2$SH, —CH$_2$(CH$_2$)$_3$NH$_2$ or —CH$_2$CH$_2$CH$_2$NHC(NH)NH$_2$. In another embodiment, n is 1 and R$^{47}$ and R$^2$ together with the atoms to which they are attached form a pyrrolidine ring. Preferably, the bridged cycloalkyl group is

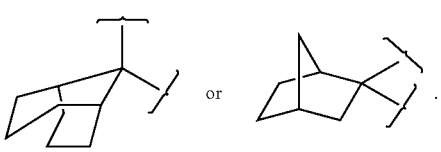

Preferably, in this embodiment, R$^7$ is hydrogen.

In still another embodiment of compounds of Formulae (I)-(X), Y is O, R$^6$ and R$^7$ are hydrogen, R$^4$ is alkyl, aryl, or cycloalkyl, R$^5$ is hydrogen or alkyl and R$^3$ is hydrogen or alkyl. In one embodiment, n is 0. In another embodiment, n is 1, R$^{47}$ is hydrogen, and R$^2$ is hydrogen, methyl, 2-propyl, 2-butyl, isobutyl, t-butyl, cyclopentyl, cyclohexyl, phenyl, benzyl, 4-hydroxybenzyl, 2-imidazolyl, 2-indolyl, —CH$_2$OH, —CH(OH)CH$_3$, —CH$_2$CO$_2$H, —CH$_2$CH$_2$CO$_2$H, —CH$_2$CONH$_2$, —CH$_2$CH$_2$CONH$_2$, —CH$_2$CH$_2$SCH$_3$, —CH$_2$SH, —CH$_2$(CH$_2$)$_3$NH$_2$ or —CH$_2$CH$_2$CH$_2$NHC(NH)NH$_2$. In another embodiment, n is 1 and R$^{47}$ and R$^2$ together with the atoms to which they are attached form a pyrrolidine ring. Preferably, R$^4$ is phenyl or cycloalkyl, R$^5$ is hydrogen or methyl and R$^3$ is hydrogen or methyl or R$^3$ is hydrogen, R$^4$ is isobutyl and R$^5$ is hydrogen.

In still another embodiment of compounds of Formulae (I)-(X), Y is O, R$^3$, R$^5$, R$^6$ and R$^7$ are hydrogen and R$^4$ is substituted aryl. In one embodiment, n is 0. In another embodiment, n is 1, R$^{47}$ is hydrogen, and R$^2$ is hydrogen, methyl, 2-propyl, 2-butyl, isobutyl, t-butyl, cyclopentyl, cyclohexyl, phenyl, benzyl, 4-hydroxybenzyl, 2-imidazolyl, 2-indolyl, —CH$_2$OH, —CH(OH)CH$_3$, —CH$_2$CO$_2$H, —CH$_2$CH$_2$CO$_2$H, —CH$_2$CONH$_2$, —CH$_2$CH$_2$CONH$_2$, —CH$_2$CH$_2$SCH$_3$, —CH$_2$SH, —CH$_2$(CH$_2$)$_3$NH$_2$ or —CH$_2$CH$_2$CH$_2$NHC(NH)NH$_2$. In another embodiment, n is 1 and R$^{47}$ and R$^2$ together with the atoms to which they are attached form a pyrrolidine ring. Preferably, R$^4$ is 4-chlorophenyl.

In still another embodiment of compounds of Formulae (I)-(X), Y is O, R$^5$ and R$^7$ are hydrogen or alkanyl, R$^3$ and R$^6$ are hydrogen and R$^4$ is substituted heteroalkyl. Preferably, R$^4$ is

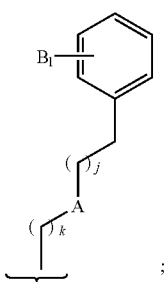

A is NR$^{19}$, O or S;

B is alkyl, substituted alkyl, alkoxy, halogen, hydroxy, carboxy, alkoxycarbonyl or amino;

R$^{19}$ is hydrogen, alkyl, cycloalkyl or aryl;

j is an integer from 0 to 4;

k is an integer from 1 to 4; and l is an integer from 0 to 3.

More preferably, k is 1.

In still another embodiment of compounds of Formulae (I)-(X), Y is O, R$^5$ and R$^7$ are hydrogen or alkanyl, R$^3$ and R$^6$ are hydrogen and R$^4$ is substituted alkanyl, cycloalkanyl or substituted cycloalkanyl. Preferably, R$^4$ is selected from the group consisting of

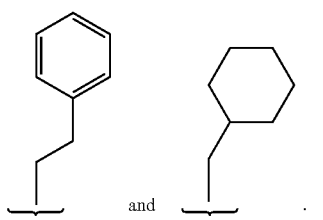

Preferably, R$^4$ is

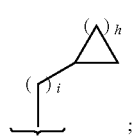

h is an integer from 1 to 6; and i is an integer from 0 to 6.

More preferably, h is 1, 2, 3 or 4 and i is 0 or 1. Even more preferably, R$^4$ is selected from the group consisting of

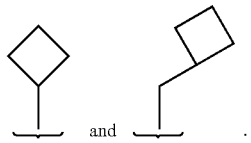

In a preferred embodiment, the compounds of Formula (II) have the structures of Formulae (XI) and (XII):

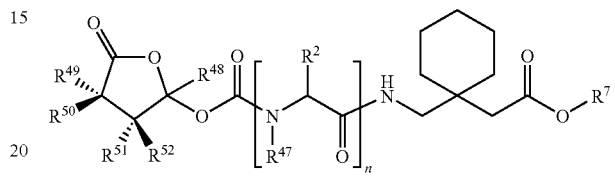

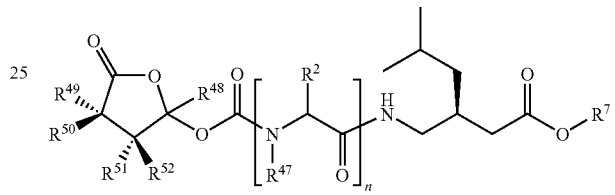

In a preferred embodiment of compounds of Formulae (XI) and (XII), R$^7$ is hydrogen. In another embodiment of compounds of Formulae (XI) and (XII), n is 0. In still another embodiment of compounds of Formulae (XI) and (XII), n is 1, R$^{47}$ is hydrogen and R$^2$ is hydrogen, methyl, 2-propyl, 2-butyl, isobutyl, t-butyl, cyclopentyl, cyclohexyl, phenyl, benzyl, 4-hydroxybenzyl, 2-imidazolyl, 2-indolyl, —CH$_2$OH, —CH(OH)CH$_3$, —CH$_2$CO$_2$H, —CH$_2$CH$_2$CO$_2$H, —CH$_2$CONH$_2$, —CH$_2$CH$_2$CONH$_2$, —CH$_2$CH$_2$SCH$_3$, —CH$_2$SH, —CH$_2$(CH$_2$)$_3$NH$_2$ or —CH$_2$CH$_2$CH$_2$NHC(NH)NH$_2$. In still another embodiment, n is 1 and R$^{47}$ and R$^2$ together with the atoms to which they are attached form a pyrrolidine ring.

In another embodiment of compounds of Formulae (XI) and (XII), R$^{48}$ is selected from the group consisting of hydrogen, alkyl, substituted alkyl, alkoxycarbonyl, substituted alkoxycarbonyl, aryl, substituted aryl, arylalkyl, substituted arylalkyl, carbamoyl, cycloalkyl, substituted cycloalkyl, heteroaryl and substituted heteroaryl. Preferably R$^{48}$ is hydrogen, methyl, ethyl, isopropyl, methoxycarbonyl, ethoxycarbonyl, isopropoxycarbonyl or phenyl. More preferably R$^{48}$ is hydrogen.

In still another embodiment of compounds of Formulae (XI) and (XII), R$^{49}$, R$^{50}$, R$^{51}$ and R$^{52}$ are independently selected from the group consisting of hydrogen, alkyl, substituted alkyl, alkoxy, acyl, substituted acyl, acylamino, acyloxy, amino, alkylamino, alkoxycarbonyl, aryl, substituted aryl, arylalkyl, carbamoyl, cycloalkyl, substituted cycloalkyl, cycloheteroalkyl, substituted cycloheteroalkyl, dialkylamino, halo, heteroalkyl, heteroaryl and hydroxy. Preferably R$^{49}$, R$^{50}$, R$^{51}$ and R$^{52}$ are independently hydrogen, methyl, ethyl, phenyl, methoxy, ethoxy, amino, acetamido, benzamido, acetoxy, benzoyloxy or hydroxy.

In a preferred embodiment, R$^{49}$ and R$^{50}$ are independently hydrogen, methyl, ethyl, phenyl, methoxy, ethoxy, amino, acetamido, benzamido, acetoxy, benzoyloxy or hydroxy and R$^{51}$ and R$^{52}$ are hydrogen. In another preferred embodiment, $R^{49}$ is hydrogen, methyl, ethyl, phenyl, methoxy, ethoxy, amino, acetamido, benzamido, acetoxy, benzoyloxy or hydroxy and $R^{50}$, $R^{51}$ and $R^{52}$ are hydrogen. In still another preferred embodiment, $R^{50}$ is hydrogen, methyl, ethyl, phenyl, methoxy, ethoxy, amino, acetamido, benzamido, acetoxy, benzoyloxy or hydroxy and $R^{49}$, $R^{51}$ and $R^{52}$ are hydrogen. In still another preferred embodiment, $R^{49}$, $R^{50}$, $R^{51}$ and $R^{52}$ are hydrogen.

In still another embodiment of compounds of Formulae (XI) and (XII), $R^{49}$ and $R^{51}$ together with the carbon atoms to which they are attached form a cycloalkyl, substituted cycloalkyl, cycloheteroalkyl or substituted cycloheteroalkyl ring. Preferably $R^{49}$ and $R^{51}$ together with the carbon atoms to which they are attached form a cyclobutyl, cyclopentyl, cyclohexyl, 2,2-dimethyl-1,3-dioxolane or 2,2-pentamethylene-1,3-dioxolane ring and $R^{50}$ and $R^{52}$ are each hydrogen.

In still another embodiment of compounds of Formulae (XI) and (XII), $R^{50}$ and $R^{52}$ together with the carbon atoms to which they are attached form a cycloalkyl, substituted cycloalkyl, cycloheteroalkyl or substituted cycloheteroalkyl ring. Preferably $R^{50}$ and $R^{52}$ together with the carbon atoms to which they are attached form a cyclobutyl, cyclopentyl, cyclohexyl, 2,2-dimethyl-1,3-dioxolane or 2,2-pentamethylene-1,3-dioxolane ring and $R^{49}$ and $R^{51}$ are hydrogen.

In still another embodiment of compounds of Formulae (XI) and (XII), $R^{50}$ and $R^{51}$ together with the carbon atoms to which they are attached form a cycloalkyl, substituted cycloalkyl, cycloheteroalkyl or substituted cycloheteroalkyl ring. Preferably $R^{50}$ and $R^{51}$ together with the carbon atoms to which they are attached form a cyclobutyl, cyclopentyl, cyclohexyl, 2,2-dimethyl-1,3-dioxolane or 2,2-pentamethylene-1,3-dioxolane ring, and $R^{49}$ and $R^{52}$ are hydrogen.

In still another embodiment of compounds of Formulae (XI) and (XII), $R^{49}$ and $R^{52}$ together with the carbon atoms to which they are attached form a cycloalkyl, substituted cycloalkyl, cycloheteroalkyl or substituted cycloheteroalkyl ring. Preferably $R^{49}$ and $R^{52}$ together with the carbon atoms to which they are attached form a cyclobutyl, cyclopentyl, cyclohexyl, 2,2-dimethyl-1,3-dioxolane or 2,2-pentamethylene-1,3-dioxolane ring, and $R^{50}$ and $R^{51}$ are each hydrogen.

In a preferred embodiment, compounds of Formula (III) have the structures of Formulae (XIII) and (XIV):

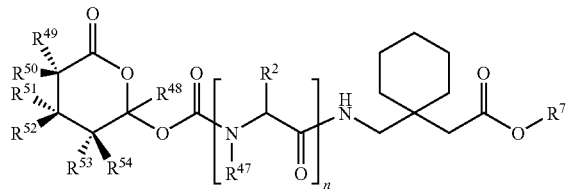

(XIII)

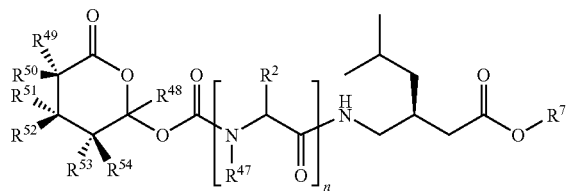

(XIV)

In a preferred embodiment of compounds of Formulae (XIII) and (XIV), $R^7$ is hydrogen. In another preferred embodiment of compounds of Formulae (XIII) and (XIV), n is 0. In still another embodiment of compounds of Formulae (XIII) and (XIV), n is 1, $R^{47}$ is hydrogen and $R^2$ is hydrogen, methyl, 2-propyl, 2-butyl, isobutyl, t-butyl, cyclopentyl, cyclohexyl, phenyl, benzyl, 4-hydroxybenzyl, 2-imidazolyl, 2-indolyl, —CH$_2$OH, —CH(OH)CH$_3$, —CH$_2$CO$_2$H, —CH$_2$CH$_2$CO$_2$H, —CH$_2$CONH$_2$, —H$_2$CH$_2$CONH$_2$, —CH$_2$CH$_2$SCH$_3$, —CH$_2$SH, —CH$_2$(CH$_2$)$_3$NH$_2$ or —CH$_2$CH$_2$CH$_2$NHC(NH)NH$_2$. In still another embodiment, n is 1 and $R^{47}$ and $R^2$ together with the atoms to which they are attached form a pyrrolidine ring.

In one embodiment of compounds of Formulae (XIII) and (XIV), $R^{48}$ is selected from the group consisting of hydrogen, alkyl, substituted alkyl, alkoxycarbonyl, substituted alkoxycarbonyl, aryl, substituted aryl, arylalkyl, substituted arylalkyl, carbamoyl, cycloalkyl, substituted cycloalkyl, heteroaryl and substituted heteroaryl. Preferably $R^{48}$ is hydrogen, methyl, ethyl, isopropyl, methoxycarbonyl, ethoxycarbonyl, isopropoxycarbonyl or phenyl. More preferably $R^{48}$ is hydrogen.

In one embodiment of compounds of Formulae (XIII) and (XIV), $R^{49}$, $R^{50}$, $R^{51}$, $R^{52}$, $R^{53}$ and $R^{54}$ are independently selected from the group consisting of hydrogen, alkyl, substituted alkyl, alkoxy, acyl, substituted acyl, acylamino, acyloxy, amino, alkylamino, alkoxycarbonyl, aryl, substituted aryl, arylalkyl, carbamoyl, cycloalkyl, substituted cycloalkyl, cycloheteroalkyl, substituted cycloheteroalkyl, dialkylamino, halo, heteroalkyl, heteroaryl and hydroxy. Preferably $R^{49}$, $R^{50}$, $R^{51}$, $R^{52}$, $R^{53}$ and $R^{54}$ are independently hydrogen, methyl, ethyl, phenyl, methoxy, ethoxy, amino, acetamido, benzamido, acetoxy, benzoyloxy or hydroxy.

In a preferred embodiment, $R^{49}$ and $R^{50}$ are independently hydrogen, methyl, ethyl, phenyl, methoxy, ethoxy, amino, acetamido, benzamido, acetoxy, benzoyloxy or hydroxy and $R^{51}$, $R^{52}$, $R^{53}$ and $R^{54}$ are hydrogen. In another preferred embodiment $R^{49}$ is hydrogen, methyl, ethyl, phenyl, methoxy, ethoxy, amino, acetamido, benzamido, acetoxy, benzoyloxy or hydroxy and $R^{50}$, $R^{51}$, $R^{52}$, $R^{53}$ and $R^{54}$ are hydrogen. In still another preferred embodiment, $R^{50}$ is hydrogen, methyl, ethyl, phenyl, methoxy, ethoxy, amino, acetamido, benzamido, acetoxy, benzoyloxy or hydroxy and $R^{49}$, $R^{51}$, $R^{52}$, $R^{53}$ and $R^{54}$ are hydrogen. In still another preferred embodiment, $R^{49}$, $R^{50}$, $R^{51}$, $R^{52}$, $R^{53}$ and $R^{54}$ are hydrogen.

In still another embodiment of compounds of Formulae (XIII) and (XIV), $R^{49}$ and $R^{51}$ together with the carbon atoms to which they are attached form a cycloalkyl, substituted cycloalkyl, cycloheteroalkyl or substituted cycloheteroalkyl ring. Preferably, $R^{49}$ and $R^{51}$ together with the carbon atoms to which they are attached form a cyclobutyl, cyclopentyl, cyclohexyl, 2,2-dimethyl-1,3-dioxolane or 2,2-pentamethylene-1,3-dioxolane ring and $R^{50}$, $R^{52}$, $R^{53}$ and $R^{54}$ are hydrogen.

In still another embodiment of compounds of Formulae (XIII) and (XIV), $R^{50}$ and $R^{52}$ together with the carbon atoms to which they are attached form a cycloalkyl, substituted cycloalkyl, cycloheteroalkyl or substituted cycloheteroalkyl ring. Preferably, $R^{50}$ and $R^{52}$ together with the carbon atoms to which they are attached form a cyclobutyl, cyclopentyl, cyclohexyl, 2,2-dimethyl-1,3-dioxolane or 2,2-pentamethylene-1,3-dioxolane ring and $R^{49}$, $R^{51}$, $R^{53}$ and $R^{54}$ are hydrogen.

In still another embodiment of compounds of Formulae (XIII) and (XIV), $R^{50}$ and $R^{51}$ together with the carbon atoms to which they are attached form a cycloalkyl, substituted cycloalkyl, cycloheteroalkyl or substituted cycloheteroalkyl ring. Preferably, $R^{50}$ and $R^{51}$ together with the carbon atoms to which they are attached form a cyclobutyl, cyclopentyl, cyclohexyl, 2,2-dimethyl-1,3-dioxolane or 2,2-pentamethylene-1,3-dioxolane ring and $R^{49}$, $R^{52}$, $R^{53}$ and $R^{54}$ are hydrogen.

In still another embodiment of compounds of Formulae (XIII) and (XIV), $R^{49}$ and $R^{52}$ together with the carbon atoms to which they are attached form a cycloalkyl, substituted cycloalkyl, cycloheteroalkyl or substituted cycloheteroalkyl ring. Preferably, $R^{49}$ and $R^{52}$ together with the carbon atoms to which they are attached form a cyclobutyl, cyclopentyl, cyclohexyl, 2,2-dimethyl-1,3-dioxolane or 2,2-pentamethylene-1,3-dioxolane ring and $R^{50}$, $R^{51}$, $R^{53}$ and $R^{54}$ are each hydrogen.

In still another embodiment of compounds of Formulae (XIII) and (XIV), $R^{51}$ and $R^{53}$ together with the carbon atoms to which they are attached form a cycloalkyl, substituted cycloalkyl, cycloheteroalkyl or substituted cycloheteroalkyl ring. Preferably, $R^{51}$ and $R^{53}$ together with the carbon atoms to which they are attached form a cyclobutyl, cyclopentyl, cyclohexyl, 2,2-dimethyl-1,3-dioxolane or 2,2-pentamethylene-1,3-dioxolane ring and $R^{49}$, $R^{50}$, $R^{52}$ and $R^{54}$ are hydrogen.

In still another embodiment of compounds of Formulae (XIII) and (XIV), $R^{52}$ and $R^{54}$ together with the carbon atoms to which they are attached form a cycloalkyl, substituted cycloalkyl, cycloheteroalkyl or substituted cycloheteroalkyl ring. Preferably, $R^{52}$ and $R^{54}$ together with the carbon atoms to which they are attached form a cyclobutyl, cyclopentyl, cyclohexyl, 2,2-dimethyl-1,3-dioxolane or 2,2-pentamethylene-1,3-dioxolane ring and $R^{49}$, $R^{50}$, $R^{51}$ and $R^{53}$ are each hydrogen.

In still another embodiment of compounds of Formulae (XIII) and (XIV), $R^{52}$ and $R^{53}$ together with the carbon atoms to which they are attached form a cycloalkyl, substituted cycloalkyl, cycloheteroalkyl or substituted cycloheteroalkyl ring. Preferably, $R^{52}$ and $R^{53}$ together with the carbon atoms to which they are attached form a cyclobutyl, cyclopentyl, cyclohexyl, 2,2-dimethyl-1,3-dioxolane or 2,2-pentamethylene-1,3-dioxolane ring and $R^{49}$, $R^{50}$, $R^{51}$ and $R^{54}$ are each hydrogen.

In still another embodiment of compounds of Formulae (XIII) and (XIV), $R^{51}$ and $R^{54}$ together with the carbon atoms to which they are attached form a cycloalkyl, substituted cycloalkyl, cycloheteroalkyl or substituted cycloheteroalkyl ring. Preferably, $R^{51}$ and $R^{54}$ together with the carbon atoms to which they are attached form a cyclobutyl, cyclopentyl, cyclohexyl, 2,2-dimethyl-1,3-dioxolane or 2,2-pentamethylene-1,3-dioxolane ring and $R^{49}$, $R^{50}$, $R^{52}$ and $R^{53}$ are hydrogen.

In a preferred embodiment, the compounds of Formula (IV) have the structures of Formulae (XV) and (XVI):

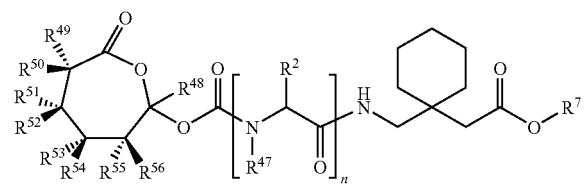

(XV)

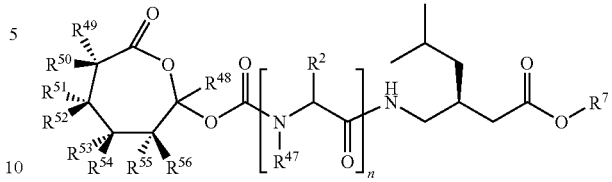

(XVI)

In a preferred embodiment of compounds of Formulae (XV) and (XVI), $R^7$ is hydrogen. In another preferred embodiment of compounds of Formulae (XV) and (XVI), n is 0. In still another embodiment of compounds of Formulae (XV) and (XVI), n is 1, $R^{47}$ is hydrogen and $R^2$ is hydrogen, methyl, 2-propyl, 2-butyl, isobutyl, t-butyl, cyclopentyl, cyclohexyl, phenyl, benzyl, 4-hydroxybenzyl, 2-imidazolyl, 2-indolyl, —$CH_2OH$, —$CH(OH)CH_3$, —$CH_2CO_2H$, —$CH_2CH_2CO_2H$, —$CH_2CONH_2$, —$CH_2CH_2CONH_2$, —$CH_2CH_2SCH_3$, —$CH_2SH$, —$CH_2(CH_2)_3NH_2$ or —$CH_2CH_2CH_2NHC(NH)NH_2$. In another embodiment, n is 1 and $R^{47}$ and $R^2$ together with the atoms to which they are attached form a pyrrolidine ring.

In an embodiment of compounds of Formulae (XV) and (XVI), $R^{48}$ is selected from the group consisting of hydrogen, alkyl, substituted alkyl, alkoxycarbonyl, substituted alkoxycarbonyl, aryl, substituted aryl, arylalkyl, substituted arylalkyl, carbamoyl, cycloalkyl, substituted cycloalkyl, heteroaryl and substituted heteroaryl. Preferably $R^{48}$ is hydrogen, methyl, ethyl, isopropyl, methoxycarbonyl, ethoxycarbonyl, isopropoxycarbonyl or phenyl. More preferably $R^{48}$ is hydrogen.

In another embodiment of compounds of Formulae (XV) and (XVI), $R^{49}$, $R^{50}$, $R^{51}$, $R^{52}$, $R^{53}$, $R^{54}$, $R^{55}$ and $R^{56}$ are independently selected from the group consisting of hydrogen, alkyl, substituted alkyl, alkoxy, acyl, substituted acyl, acylamino, acyloxy, amino, alkylamino, alkoxycarbonyl, aryl, substituted aryl, arylalkyl, carbamoyl, cycloalkyl, substituted cycloalkyl, cycloheteroalkyl, substituted cycloheteroalkyl, dialkylamino, halo, heteroalkyl, heteroaryl and hydroxy. Preferably $R^{49}$, $R^{50}$, $R^{51}$, $R^{52}$, $R^{53}$, $R^{54}$, $R^{55}$ and $R^{56}$ are independently hydrogen, methyl, ethyl, phenyl, methoxy, ethoxy, amino, acetamido, benzamido, acetoxy, benzoyloxy or hydroxy.

In a preferred embodiment, $R^{49}$ and $R^{50}$ are independently hydrogen, methyl, ethyl, phenyl, methoxy, ethoxy, amino, acetamido, benzamido, acetoxy, benzoyloxy or hydroxy and $R^{51}$, $R^{52}$, $R^{53}$, $R^{54}$, $R^{55}$ and $R^{56}$ are hydrogen. In another preferred embodiment, $R^{49}$ is hydrogen, methyl, ethyl, phenyl, methoxy, ethoxy, amino, acetamido, benzamido, acetoxy, benzoyloxy or hydroxy, and $R^{50}$, $R^{51}$, $R^{52}$, $R^{53}$, $R^{54}$, $R^{55}$ and $R^{56}$ are hydrogen. In still another preferred embodiment, $R^{50}$ is hydrogen, methyl, ethyl, phenyl, methoxy, ethoxy, amino, acetamido, benzamido, acetoxy, benzoyloxy or hydroxy and $R^{49}$, $R^{51}$, $R^{52}$, $R^{53}$, $R^{54}$, $R^{55}$ and $R^{56}$ are hydrogen. In still another preferred embodiment $R^{49}$, $R^{50}$, $R^{51}$, $R^{52}$, $R^{53}$, $R^{54}$, $R^{55}$ and $R^{56}$ are hydrogen.

In still another embodiment of compounds of Formulae (XV) and (XVI), $R^{49}$ and $R^{51}$ together with the carbon atoms to which they are attached form a cycloalkyl, substituted cycloalkyl, cycloheteroalkyl or substituted cycloheteroalkyl ring. Preferably, $R^{49}$ and $R^{51}$ together with the carbon atoms to which they are attached form a cyclobutyl, cyclopentyl, cyclohexyl, 2,2-dimethyl-1,3-dioxolane or 2,2-pentamethylene-1,3-dioxolane ring and $R^{50}$, $R^{52}$, $R^{53}$, $R^{54}$, $R^{55}$ and $R^{56}$ are hydrogen.

In still another embodiment of compounds of Formulae (XV) and (XVI), $R^{50}$ and $R^{52}$ together with the carbon atoms to which they are attached form a cycloalkyl, substituted cycloalkyl, cycloheteroalkyl or substituted cycloheteroalkyl ring. Preferably, $R^{50}$ and $R^{52}$ together with the carbon atoms to which they are attached form a cyclobutyl, cyclopentyl, cyclohexyl, 2,2-dimethyl-1,3-dioxolane or 2,2-pentamethylene-1,3-dioxolane ring and $R^{49}$, $R^{51}$, $R^{53}$, $R^{54}$, $R^{55}$ and $R^{56}$ are hydrogen.

In still another embodiment of compounds of Formulae (XV) and (XVI), $R^{50}$ and $R^{51}$ together with the carbon atoms to which they are attached form a cycloalkyl, substituted cycloalkyl, cycloheteroalkyl or substituted cycloheteroalkyl ring. Preferably, $R^{50}$ and $R^{51}$ together with the carbon atoms to which they are attached form a cyclobutyl, cyclopentyl, cyclohexyl, 2,2-dimethyl-1,3-dioxolane or 2,2-pentamethylene-1,3-dioxolane ring and $R^{49}$, $R^{52}$, $R^{53}$, $R^{54}$, $R^{55}$ and $R^{56}$ are hydrogen.

In still another embodiment of compounds of Formulae (XV) and (XVI), $R^{49}$ and $R^{52}$ together with the carbon atoms to which they are attached form a cycloalkyl, substituted cycloalkyl, cycloheteroalkyl or substituted cycloheteroalkyl ring. Preferably, $R^{49}$ and $R^{52}$ together with the carbon atoms to which they are attached form a cyclobutyl, cyclopentyl, cyclohexyl, 2,2-dimethyl-1,3-dioxolane or 2,2-pentamethylene-1,3-dioxolane ring and $R^{50}$, $R^{51}$, $R^{53}$, $R^{54}$, $R^{55}$ and $R^{56}$ are hydrogen.

In still another embodiment of compounds of Formulae (XV) and (XVI), $R^{51}$ and $R^{53}$ together with the carbon atoms to which they are attached form a cycloalkyl, substituted cycloalkyl, cycloheteroalkyl or substituted cycloheteroalkyl ring. Preferably, $R^{51}$ and $R^{53}$ together with the carbon atoms to which they are attached form a cyclobutyl, cyclopentyl, cyclohexyl, 2,2-dimethyl-1,3-dioxolane or 2,2-pentamethylene-1,3-dioxolane ring, and $R^{49}$, $R^{50}$, $R^{52}$, $R^{54}$, $R^{55}$ and $R^{56}$ are hydrogen.

In still another embodiment, of compounds of Formulae (XV) and (XVI), $R^{52}$ and $R^{54}$ together with the carbon atoms to which they are attached form a cycloalkyl, substituted cycloalkyl, cycloheteroalkyl or substituted cycloheteroalkyl ring. Preferably, $R^{52}$ and $R^{54}$ together with the carbon atoms to which they are attached form a cyclobutyl, cyclopentyl, cyclohexyl, 2,2-dimethyl-1,3-dioxolane or 2,2-pentamethylene-1,3-dioxolane ring and $R^{49}$, $R^{50}$, $R^{51}$, $R^{53}$, $R^{55}$ and $R^{56}$ are each hydrogen.

In still another embodiment of compounds of Formulae (XV) and (XVI), $R^{52}$ and $R^{53}$ together with the carbon atoms to which they are attached form a cycloalkyl, substituted cycloalkyl, cycloheteroalkyl or substituted cycloheteroalkyl ring. Preferably, $R^{52}$ and $R^{53}$ together with the carbon atoms to which they are attached form a cyclobutyl, cyclopentyl, cyclohexyl, 2,2-dimethyl-1,3-dioxolane or 2,2-pentamethylene-1,3-dioxolane ring and $R^{49}$, $R^{50}$, $R^{51}$, $R^{54}$, $R^{55}$ and $R^{56}$ are hydrogen.

In still another embodiment of compounds of Formulae (XV) and (XVI), $R^{51}$ and $R^{54}$ together with the carbon atoms to which they are attached form a cycloalkyl, substituted cycloalkyl, cycloheteroalkyl or substituted cycloheteroalkyl ring. Preferably, $R^{51}$ and $R^{54}$ together with the carbon atoms to which they are attached form a cyclobutyl, cyclopentyl, cyclohexyl, 2,2-dimethyl-1,3-dioxolane or 2,2-pentamethylene-1,3-dioxolane ring and $R^{49}$, $R^{50}$, $R^{52}$, $R^{53}$, $R^{55}$ and $R^{56}$ are hydrogen.

In still another embodiment of compounds of Formulae (XV) and (XVI), $R^{53}$ and $R^{55}$ together with the carbon atoms to which they are attached form a cycloalkyl, substituted cycloalkyl, cycloheteroalkyl or substituted cycloheteroalkyl ring. Preferably, $R^{53}$ and $R^{55}$ together with the carbon atoms to which they are attached form a cyclobutyl, cyclopentyl, cyclohexyl, 2,2-dimethyl-1,3-dioxolane or 2,2-pentamethylene-1,3-dioxolane ring and $R^{49}$, $R^{50}$, $R^{51}$, $R^{52}$, $R^{54}$ and $R^{56}$ are each hydrogen.

In still another embodiment of compounds of Formulae (XV) and (XVI), $R^{54}$ and $R^{56}$ together with the carbon atoms to which they are attached form a cycloalkyl, substituted cycloalkyl, cycloheteroalkyl or substituted cycloheteroalkyl ring. Preferably, $R^{54}$ and $R^{56}$ together with the carbon atoms to which they are attached form a cyclobutyl, cyclopentyl, cyclohexyl, 2,2-dimethyl-1,3-dioxolane or 2,2-pentamethylene-1,3-dioxolane ring and $R^{49}$, $R^{50}$, $R^{51}$, $R^{52}$, $R^{53}$ and $R^{55}$ are each hydrogen.

In still another embodiment of compounds of Formulae (XV) and (XVI), $R^{54}$ and $R^{55}$ together with the carbon atoms to which they are attached form a cycloalkyl, substituted cycloalkyl, cycloheteroalkyl or substituted cycloheteroalkyl ring. Preferably, $R^{54}$ and $R^{55}$ together with the carbon atoms to which they are attached form a cyclobutyl, cyclopentyl, cyclohexyl, 2,2-dimethyl-1,3-dioxolane or 2,2-pentamethylene-1,3-dioxolane ring, and $R^{49}$, $R^{50}$, $R^{51}$, $R^{52}$, $R^{53}$ and $R^{56}$ are each hydrogen.

In still another embodiment of compounds of Formulae (XV) and (XVI), $R^{53}$ and $R^{56}$ together with the carbon atoms to which they are attached form a cycloalkyl, substituted cycloalkyl, cycloheteroalkyl or substituted cycloheteroalkyl ring. Preferably, $R^{53}$ and $R^{56}$ together with the carbon atoms to which they are attached form a cyclobutyl, cyclopentyl, cyclohexyl, 2,2-dimethyl-1,3-dioxolane or 2,2-pentamethylene-1,3-dioxolane ring, and $R^{49}$, $R^{50}$, $R^{51}$, $R^{52}$, $R^{54}$ and $R^{55}$ are each hydrogen.

In a preferred embodiment, the compounds of Formula (V) have the structures of Formulae (XVII) and (XVIII):

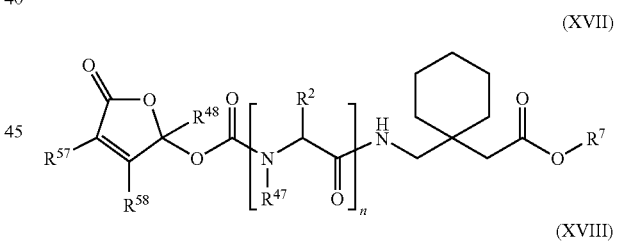

(XVII)

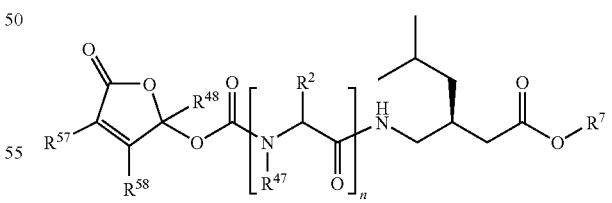

(XVIII)

In a preferred embodiment of compounds of Formulae (XVII) and (XVIII), $R^7$ is hydrogen. In another preferred embodiment of compounds of Formulae (XVII) and (XVIII), n is 0. In still another embodiment of compounds of Formulae (XVII) and (XVIII), n is 1, $R^{47}$ is hydrogen and $R^2$ is hydrogen, methyl, 2-propyl, 2-butyl, isobutyl, t-butyl, cyclopentyl, cyclohexyl, phenyl, benzyl, 4-hydroxybenzyl, 2-imidazolyl, 2-indolyl, —CH$_2$OH, —CH(OH)CH$_3$, —CH$_2$CO$_2$H, —CH$_2$CH$_2$CO$_2$H, —CH$_2$CONH$_2$, —CH$_2$CH$_2$CONH$_2$, —$CH_2CH_2SCH_3$, —$CH_2SH$, —$CH_2(CH_2)_3NH_2$ or —$CH_2CH_2CH_2NHC(NH)NH_2$. In still another embodiment, n is 1 and $R^{47}$ and $R^2$ together with the atoms to which they are attached form a pyrrolidine ring.

In an embodiment of compounds of Formulae (XVII) and (XVIII), $R^{48}$ is selected from the group consisting of hydrogen, alkyl, substituted alkyl, alkoxycarbonyl, substituted alkoxycarbonyl, aryl, substituted aryl, arylalkyl, substituted arylalkyl, carbamoyl, cycloalkyl, substituted cycloalkyl, heteroaryl and substituted heteroaryl. Preferably $R^{48}$ is hydrogen, methyl, ethyl, isopropyl, methoxycarbonyl, ethoxycarbonyl, isopropoxycarbonyl or phenyl. More preferably $R^{48}$ is hydrogen.

In another embodiment of compounds of Formulae (XVII) and (XVIII), $R^{57}$ and $R^{58}$ are independently hydrogen, alkyl, substituted alkyl, acylamino, aryl, substituted aryl, arylalkyl, cycloalkyl, cycloheteroalkyl, heteroalkyl, substituted heteroalkyl, heteroaryl or substituted heteroaryl. Preferably, $R^{57}$ and $R^{58}$ are independently hydrogen, methyl, ethyl or phenyl. Preferably $R^{57}$ is hydrogen, methyl, ethyl or phenyl and $R^{58}$ is hydrogen or methyl. Preferably $R^{58}$ is selected from the group consisting of hydrogen, methyl, ethyl or phenyl and $R^{57}$ is hydrogen or methyl.

In still another embodiment of compounds of Formulae (XVII) and (XVIII), $R^{57}$ and $R^{58}$ together with the carbon atoms to which they are attached form an aryl, substituted aryl, heteroaryl, substituted heteroaryl, cycloalkyl or substituted cycloalkyl ring. Preferably, $R^{57}$ and $R^{58}$ together with the carbon atoms to which they are attached form a cyclopentenyl, cyclohexenyl, phenyl, furyl, thienyl, pyrrolyl, benzothienyl, benzofuryl, indolyl, pyridyl, quinolyl, imidazolyl or oxazolyl ring. More preferably, $R^{57}$ and $R^{58}$ together with the carbon atoms to which they are attached form a phenyl ring.

In a preferred embodiment, compounds of Formula (VI) have the structures of Formulae (XIX) and (XX):

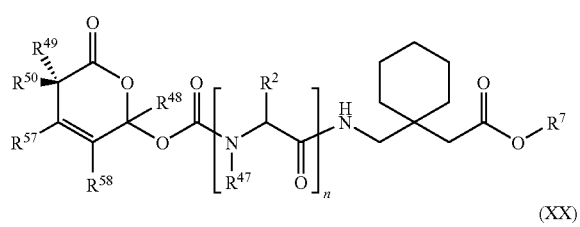

(XIX)

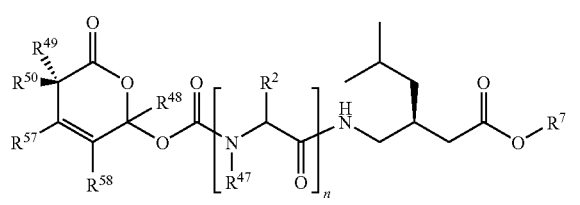

(XX)

In a preferred embodiment of compounds of Formulae (XIX) and (XX), $R^7$ is hydrogen. In another preferred embodiment of compounds of Formulae (XIX) and (XX), n is 0. In still another preferred embodiment, of compounds of Formulae (XIX) and (XX), n is 1, $R^{47}$ is hydrogen and $R^2$ is hydrogen, methyl, 2-propyl, 2-butyl, isobutyl, t-butyl, cyclopentyl, cyclohexyl, phenyl, benzyl, 4-hydroxybenzyl, 2-imidazolyl, 2-indolyl, —$CH_2OH$, —$CH(OH)CH_3$, —$CH_2CO_2H$, —$CH_2CH_2CO_2H$, —$CH_2CONH_2$, —$CH_2CH_2CONH_2$, —$CH_2CH_2SCH_3$, —$CH_2SH$, —$CH_2(CH_2)_3NH_2$ or —$CH_2CH_2CH_2NHC(NH)NH_2$. In still another embodiment, n is 1 and $R^{47}$ and $R^2$ together with the atoms to which they are attached form a pyrrolidine ring.

In one embodiment of compounds of Formulae (XIX) and (XX), $R^{48}$ is selected from the group consisting of hydrogen, alkyl, substituted alkyl, alkoxycarbonyl, substituted alkoxycarbonyl, aryl, substituted aryl, arylalkyl, substituted arylalkyl, carbamoyl, cycloalkyl, substituted cycloalkyl, heteroaryl and substituted heteroaryl. Preferably $R^{48}$ is hydrogen, methyl, ethyl, isopropyl, methoxycarbonyl, ethoxycarbonyl, isopropoxycarbonyl or phenyl. More preferably $R^{48}$ is hydrogen.

In another embodiment of compounds of Formulae (XIX) and (XX), $R^{49}$ and $R^{50}$ are independently selected from the group consisting of hydrogen, alkyl, substituted alkyl, alkoxy, acyl, substituted acyl, acylamino, acyloxy, amino, alkylamino, alkoxycarbonyl, aryl, substituted aryl, arylalkyl, carbamoyl, cycloalkyl, substituted cycloalkyl, cycloheteroalkyl, substituted cycloheteroalkyl, dialkylamino, halo, heteroalkyl, heteroaryl and hydroxy and $R^{57}$ and $R^{58}$ are independently hydrogen, alkyl, substituted alkyl, acylamino, aryl, substituted aryl, arylalkyl, cycloalkyl, cycloheteroalkyl, heteroalkyl, substituted heteroalkyl, heteroaryl or substituted heteroaryl. Preferably, $R^{49}$ and $R^{50}$ are independently hydrogen, methyl, ethyl, phenyl, methoxy, ethoxy, amino, acetamido, benzamido, acetoxy, benzoyloxy or hydroxy and $R^{57}$ and $R^{58}$ are independently hydrogen, methyl, ethyl or phenyl.

In a preferred embodiment, $R^{49}$ and $R^{50}$ are hydrogen, methyl, ethyl, phenyl, methoxy, ethoxy, amino, acetamido, benzamido, acetoxy, benzoyloxy or hydroxy and $R^{57}$ and $R^{58}$ are hydrogen. In another preferred embodiment, $R^{49}$ is hydrogen, methyl, ethyl, phenyl, methoxy, ethoxy, amino, acetamido, benzamido, acetoxy, benzoyloxy or hydroxy and $R^{50}$, $R^{57}$ and $R^{58}$ are hydrogen. In still another preferred embodiment $R^{50}$ is hydrogen, methyl, ethyl, phenyl, methoxy, ethoxy, amino, acetamido, benzamido, acetoxy, benzoyloxy or hydroxy and $R^{49}$, $R^{57}$ and $R^{58}$ are hydrogen. In another preferred embodiment $R^{49}$, $R^{50}$, $R^{57}$ and $R^{58}$ are hydrogen.

In yet another preferred embodiment of compounds of Formulae (XIX) and (XX), $R^{49}$ and $R^{50}$ are independently selected from the group consisting of hydrogen, alkyl, substituted alkyl, alkoxy, acyl, substituted acyl, acylamino, acyloxy, amino, alkylamino, alkoxycarbonyl, aryl, substituted aryl, arylalkyl, carbamoyl, cycloalkyl, substituted cycloalkyl, cycloheteroalkyl, substituted cycloheteroalkyl, dialkylamino, halo, heteroalkyl, heteroaryl and hydroxy and $R^{57}$ and $R^{58}$ together with the carbon atoms to which they are attached form an aryl, substituted aryl, heteroaryl, substituted heteroaryl, cycloalkyl or substituted cycloalkyl ring. Preferably, $R^{49}$ and $R^{50}$ are independently hydrogen or methyl and $R^{57}$ and $R^{58}$ together with the carbon atoms to which they are attached form a cyclopentenyl, cyclohexenyl, phenyl, furyl, thienyl, pyrrolyl, benzothienyl, benzofuryl, indolyl, pyridyl, quinolyl, imidazolyl or oxazolyl ring. More preferably, $R^{49}$ and $R^{50}$ are independently hydrogen or methyl and $R^{57}$ and $R^{58}$ together with the carbon atoms to which they are attached form a phenyl ring. Most preferably, $R^{49}$ and $R^{50}$ are hydrogen, and $R^{57}$ and $R^{58}$ together with the carbon atoms to which they are attached form a phenyl ring.

In a preferred embodiment, the compounds of Formula (VII) have the structures of Formulae (XXI) and (XXII):

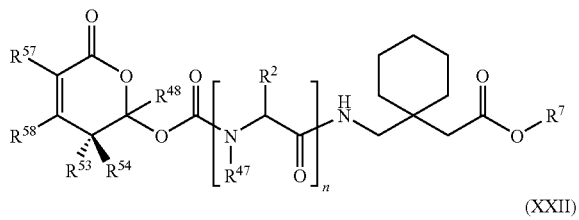

(XXI)

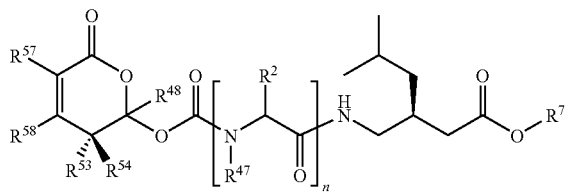

(XXII)

In a preferred embodiment of compounds of Formulae (XXI) and (XXII), $R^7$ is hydrogen. In another preferred embodiment of compounds of Formulae (XXI) and (XXII), n is 0. In still another embodiment of compounds of Formulae (XXI) and (XXII), n is 1, $R^{47}$ is hydrogen and $R^2$ is hydrogen, methyl, 2-propyl, 2-butyl, isobutyl, t-butyl, cyclopentyl, cyclohexyl, phenyl, benzyl, 4-hydroxybenzyl, 2-imidazolyl, 2-indolyl, —CH$_2$OH, —CH(OH)CH$_3$, —CH$_2$CO$_2$H, —CH$_2$CH$_2$CO$_2$H, —CH$_2$CONH$_2$, —CH$_2$CH$_2$CONH$_2$, —CH$_2$CH$_2$SCH$_3$, —CH$_2$SH, —CH$_2$(CH$_2$)$_3$NH$_2$ or —CH$_2$CH$_2$CH$_2$NHC(NH)NH$_2$. In still another embodiment, n is 1 and $R^{47}$ and $R^2$ together with the atoms to which they are attached form a pyrrolidine ring.

In one embodiment of compounds of Formulae (XXI) and (XXII), $R^{48}$ is selected from the group consisting of hydrogen, alkyl, substituted alkyl, alkoxycarbonyl, substituted alkoxycarbonyl, aryl, substituted aryl, arylalkyl, substituted arylalkyl, carbamoyl, cycloalkyl, substituted cycloalkyl, heteroaryl and substituted heteroaryl. Preferably $R^{48}$ is hydrogen, methyl, ethyl, isopropyl, methoxycarbonyl, ethoxycarbonyl, isopropoxycarbonyl or phenyl. More preferably, $R^{48}$ is hydrogen.

In another embodiment of compounds of Formulae (XXI) and (XXII), $R^{53}$ and $R^{54}$ are independently selected from the group consisting of hydrogen, alkyl, substituted alkyl, alkoxy, acyl, substituted acyl, acylamino, acyloxy, amino, alkylamino, alkoxycarbonyl, aryl, substituted aryl, arylalkyl, carbamoyl, cycloalkyl, substituted cycloalkyl, cycloheteroalkyl, substituted cycloheteroalkyl, dialkylamino, halo, heteroalkyl, heteroaryl and hydroxy and $R^{57}$ and $R^{58}$ are independently hydrogen, alkyl, substituted alkyl, acylamino, aryl, substituted aryl, arylalkyl, cycloalkyl, cycloheteroalkyl, heteroalkyl, substituted heteroalkyl, heteroaryl or substituted heteroaryl. Preferably $R^{53}$ and $R^{54}$ are independently hydrogen, methyl, ethyl, phenyl, methoxy, ethoxy, amino, acetamido, benzamido, acetoxy, benzoyloxy or hydroxy and $R^{57}$ and $R^{58}$ are independently hydrogen, methyl, ethyl or phenyl.

In a preferred embodiment, $R^{53}$ and $R^{54}$ are independently hydrogen, methyl, ethyl, phenyl, methoxy, ethoxy, amino, acetamido, benzamido, acetoxy, benzoyloxy or hydroxy and $R^{57}$ and $R^{58}$ are hydrogen. In another preferred embodiment, $R^{53}$ is hydrogen, methyl, ethyl, phenyl, methoxy, ethoxy, amino, acetamido, benzamido, acetoxy, benzoyloxy or hydroxy and $R^{54}$, $R^{57}$ and $R^{58}$ are hydrogen. In still another preferred embodiment $R^{54}$ is hydrogen, methyl, ethyl, phenyl, methoxy, ethoxy, amino, acetamido, benzamido, acetoxy, benzoyloxy or hydroxy and $R^{53}$, $R^{57}$ and $R^{58}$ are hydrogen. In still another preferred embodiment, $R^{53}$, $R^{54}$, $R^{57}$ and $R^{58}$ are hydrogen.

In yet another preferred embodiment of compounds of Formulae (XXI) and (XXII), $R^{53}$ and $R^{54}$ are independently selected from the group consisting of hydrogen, alkyl, substituted alkyl, alkoxy, acyl, substituted acyl, acylamino, acyloxy, amino, alkylamino, alkoxycarbonyl, aryl, substituted aryl, arylalkyl, carbamoyl, cycloalkyl, substituted cycloalkyl, cycloheteroalkyl, substituted cycloheteroalkyl, dialkylamino, halo, heteroalkyl, heteroaryl and hydroxy and $R^{57}$ and $R^{58}$ together with the carbon atoms to which they are attached form an aryl, substituted aryl, heteroaryl, substituted heteroaryl, cycloalkyl or substituted cycloalkyl ring. Preferably, $R^{53}$ and $R^{54}$ are independently hydrogen or methyl and $R^{57}$ and $R^{58}$ together with the carbon atoms to which they are attached form a cyclopentenyl, cyclohexenyl, phenyl, furyl, thienyl, pyrrolyl, benzothienyl, benzofuryl, indolyl, pyridyl, quinolyl, imidazolyl or oxazolyl ring. More preferably, $R^{53}$ and $R^{54}$ are independently hydrogen or methyl, and $R^{57}$ and $R^{58}$ together with the carbon atoms to which they are attached form a phenyl ring. Even more preferably, $R^{53}$ and $R^{54}$ are hydrogen, and $R^{57}$ and $R^{58}$ together with the carbon atoms to which they are attached form a phenyl ring.

In a preferred embodiment, compounds of Formula (VIII) have the structures of Formulae (XXIII) and (XXIV):

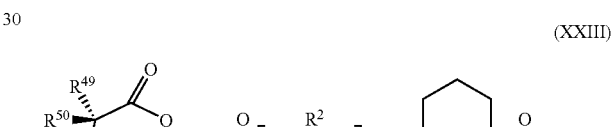

(XXIII)

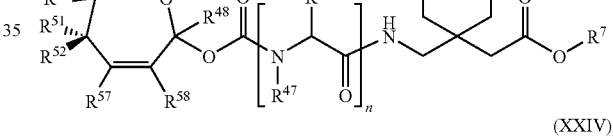

(XXIV)

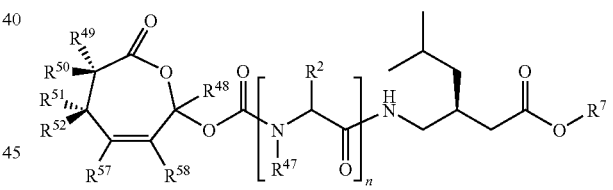

In a preferred embodiments of compounds of Formulae (XXIII) and (XXIV), $R^7$ is hydrogen. In another preferred embodiment of compounds of Formulae (XXIII) and (XXIV), n is 0. In still another embodiment of compounds of Formulae (XXIII) and (XXIV), n is 1, $R^{47}$ is hydrogen and $R^2$ is hydrogen, methyl, 2-propyl, 2-butyl, isobutyl, t-butyl, cyclopentyl, cyclohexyl, phenyl, benzyl, 4-hydroxybenzyl, 2-imidazolyl, 2-indolyl, —CH$_2$OH, —CH(OH)CH$_3$, —CH$_2$CO$_2$H, —CH$_2$CH$_2$CO$_2$H, —CH$_2$CONH$_2$, —CH$_2$CH$_2$CONH$_2$, —CH$_2$CH$_2$SCH$_3$, —CH$_2$SH, —CH$_2$(CH$_2$)$_3$NH$_2$ or —CH$_2$CH$_2$CH$_2$NHC(NH)NH$_2$. In still another embodiment, n is 1 and $R^{47}$ and $R^2$ together with the atoms to which they are attached form a pyrrolidine ring.

In one embodiment of compounds of Formulae (XXIII) and (XXIV), $R^{48}$ is selected from the group consisting of hydrogen, alkyl, substituted alkyl, alkoxycarbonyl, substituted alkoxycarbonyl, aryl, substituted aryl, arylalkyl, substituted arylalkyl, carbamoyl, cycloalkyl, substituted cycloalkyl, heteroaryl and substituted heteroaryl. Preferably, $R^{48}$ is hydrogen, methyl, ethyl, isopropyl, methoxycarbonyl, ethoxycarbonyl, isopropoxycarbonyl or phenyl. More preferably, $R^{48}$ is hydrogen.

In another embodiment of compounds of Formulae (XXIII) and (XXIV), $R^{49}$, $R^{50}$, $R^{51}$ and $R^{52}$ are independently selected from the group consisting of hydrogen, alkyl, substituted alkyl, alkoxy, acyl, substituted acyl, acylamino, acyloxy, amino, alkylamino, alkoxycarbonyl, aryl, substituted aryl, arylalkyl, carbamoyl, cycloalkyl, substituted cycloalkyl, cycloheteroalkyl, substituted cycloheteroalkyl, dialkylamino, halo, heteroalkyl, heteroaryl and hydroxy and $R^{57}$ and $R^{58}$ are independently hydrogen, alkyl, substituted alkyl, acylamino, aryl, substituted aryl, arylalkyl, cycloalkyl, cycloheteroalkyl, heteroalkyl, substituted heteroalkyl, heteroaryl or substituted heteroaryl. Preferably, $R^{49}$, $R^{50}$, $R^{51}$ and $R^{52}$ are independently hydrogen, methyl, ethyl, phenyl, methoxy, ethoxy, amino, acetamido, benzamido, acetoxy, benzoyloxy or hydroxy and $R^{57}$ and $R^{58}$ are independently hydrogen, methyl, ethyl or phenyl.

In a preferred embodiment, $R^{49}$, $R^{50}$, $R^{51}$ and $R^{52}$ are independently hydrogen, methyl, ethyl, phenyl, methoxy, ethoxy, amino, acetamido, benzamido, acetoxy, benzoyloxy or hydroxy and $R^{57}$ and $R^{58}$ are hydrogen. In another preferred embodiment, $R^{49}$ is hydrogen, methyl, ethyl, phenyl, methoxy, ethoxy, amino, acetamido, benzamido, acetoxy, benzoyloxy or hydroxy and $R^{50}$, $R^{51}$, $R^{52}$, $R^{57}$ and $R^{58}$ are hydrogen. In still another preferred embodiment, $R^{50}$ is hydrogen, methyl, ethyl, phenyl, methoxy, ethoxy, amino, acetamido, benzamido, acetoxy, benzoyloxy or hydroxy and $R^{49}$, $R^{51}$, $R^{52}$, $R^{57}$ and $R^{58}$ are hydrogen. In still another preferred embodiment, $R^{49}$, $R^{50}$, $R^{51}$, $R^{52}$, $R^{57}$ and $R^{58}$ are hydrogen.

In yet another preferred embodiment of compounds of Formulae (XXIII) and (XXIV), $R^{49}$, $R^{50}$, $R^{51}$ and $R^{52}$ are independently selected from the group consisting of hydrogen, alkyl, substituted alkyl, alkoxy, acyl, substituted acyl, acylamino, acyloxy, amino, alkylamino, alkoxycarbonyl, aryl, substituted aryl, arylalkyl, carbamoyl, cycloalkyl, substituted cycloalkyl, cycloheteroalkyl, substituted cycloheteroalkyl, dialkylamino, halo, heteroalkyl, heteroaryl and hydroxy and $R^{57}$ and $R^{58}$ together with the carbon atoms to which they are attached form an aryl, substituted aryl, heteroaryl, substituted heteroaryl, cycloalkyl or substituted cycloalkyl ring. Preferably, $R^{49}$, $R^{50}$, $R^{51}$ and $R^{52}$ are independently hydrogen or methyl, and $R^{57}$ and $R^{58}$ together with the carbon atoms to which are attached form a cyclopentenyl, cyclohexenyl, phenyl, furyl, thienyl, pyrrolyl, benzothienyl, benzofuryl, indolyl, pyridyl, quinolyl, imidazolyl or oxazolyl ring. More preferably, $R^{49}$, $R^{50}$, $R^{51}$ and $R^{52}$ are independently hydrogen or methyl and $R^{57}$ and $R^{58}$ together with the carbon atoms to which they are attached form a phenyl ring. Even more preferably, $R^{49}$, $R^{50}$, $R^{51}$ and $R^{52}$ are hydrogen, and $R^{57}$ and $R^{58}$ together with the carbon atoms to which they are attached form a phenyl ring.

In a preferred embodiment, the compounds of Formula (IX) have the structures of Formulae (XXV) and (XXVI):

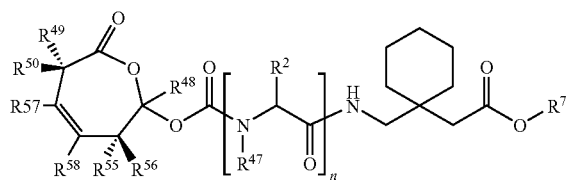

(XXV)

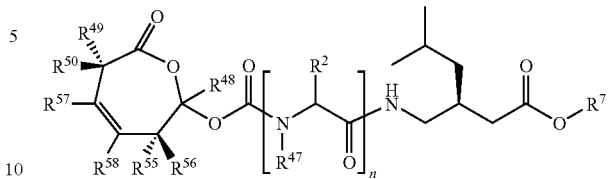

(XXVI)

In a preferred embodiment of compounds of Formulae (XXV) and (XXVI), $R^7$ is hydrogen. In another preferred embodiment of compounds of Formulae (XXV) and (XXVI), n is 0. In still another embodiment of compounds of Formulae (XXV) and (XXVI), n is 1, $R^{47}$ is hydrogen and $R^2$ is hydrogen, methyl, 2-propyl, 2-butyl, isobutyl, t-butyl, cyclopentyl, cyclohexyl, phenyl, benzyl, 4-hydroxybenzyl, 2-imidazolyl, 2-indolyl, —$CH_2OH$, —$CH(OH)CH_3$, —$CH_2CO_2H$, —$CH_2CH_2CO_2H$, —$CH_2CONH_2$, —$CH_2CH_2CONH_2$, —$CH_2CH_2SCH_3$, —$CH_2SH$, —$CH_2(CH_2)_3NH_2$ or —$CH_2CH_2CH_2NHC(NH)NH_2$. In still another embodiment, n is 1 and $R^{47}$ and $R^2$ together with the atoms to which they are attached form a pyrrolidine ring.

In one embodiment of compounds of Formulae (XXV) and (XXVI), $R^{48}$ is selected from the group consisting of hydrogen, alkyl, substituted alkyl, alkoxycarbonyl, substituted alkoxycarbonyl, aryl, substituted aryl, arylalkyl, substituted arylalkyl, carbamoyl, cycloalkyl, substituted cycloalkyl, heteroaryl and substituted heteroaryl. Preferably $R^{48}$ is hydrogen, methyl, ethyl, isopropyl, methoxycarbonyl, ethoxycarbonyl, isopropoxycarbonyl or phenyl. More preferably $R^{48}$ is hydrogen.

In another embodiment of compounds of Formulae (XXV) and (XXVI), $R^{49}$, $R^{50}$, $R^{55}$ and $R^{56}$ are independently selected from the group consisting of hydrogen, alkyl, substituted alkyl, alkoxy, acyl, substituted acyl, acylamino, acyloxy, amino, alkylamino, alkoxycarbonyl, aryl, substituted aryl, arylalkyl, carbamoyl, cycloalkyl, substituted cycloalkyl, cycloheteroalkyl, substituted cycloheteroalkyl, dialkylamino, halo, heteroalkyl, heteroaryl and hydroxy and $R^{57}$ and $R^{58}$ are independently selected from the group consisting of hydrogen, alkyl, substituted alkyl, acylamino, aryl, substituted aryl, arylalkyl, cycloalkyl, cycloheteroalkyl, heteroalkyl, substituted heteroalkyl, heteroaryl or substituted heteroaryl. Preferably $R^{49}$, $R^{50}$, $R^{55}$ and $R^{56}$ are independently hydrogen, methyl, ethyl, phenyl, methoxy, ethoxy, amino, acetamido, benzamido, acetoxy, benzoyloxy or hydroxy and $R^{57}$ and $R^{58}$ are independently hydrogen, methyl, ethyl or phenyl.

In a preferred embodiment $R^{49}$, $R^{50}$, $R^{55}$ and $R^{56}$ are independently hydrogen, methyl, ethyl, phenyl, methoxy, ethoxy, amino, acetamido, benzamido, acetoxy, benzoyloxy or hydroxy and $R^{57}$ and $R^{58}$ are hydrogen. In another preferred embodiment $R^{49}$ is hydrogen, methyl, ethyl, phenyl, methoxy, ethoxy, amino, acetamido, benzamido, acetoxy, benzoyloxy or hydroxy and $R^{50}$, $R^{55}$, $R^{56}$, $R^{57}$ and $R^{58}$ are hydrogen. In still another preferred embodiment, $R^{50}$ is hydrogen, methyl, ethyl, phenyl, methoxy, ethoxy, amino, acetamido, benzamido, acetoxy, benzoyloxy or hydroxy and $R^{49}$, $R^{55}$, $R^{56}$, $R^{57}$ and $R^{58}$ are hydrogen. In another preferred embodiment, $R^{49}$, $R^{50}$, $R^{55}$, $R^{56}$, $R^{57}$ and $R^{58}$ are hydrogen.

In yet another preferred embodiment of compounds of Formulae (XXV) and (XXVI), $R^{49}$, $R^{50}$, $R^{55}$ and $R^{56}$ are independently selected from the group consisting of hydrogen, alkyl, substituted alkyl, alkoxy, acyl, substituted acyl, acylamino, acyloxy, amino, alkylamino, alkoxycarbonyl, aryl, substituted aryl, arylalkyl, carbamoyl, cycloalkyl, substituted cycloalkyl, cycloheteroalkyl, substituted cycloheteroalkyl, dialkylamino, halo, heteroalkyl, heteroaryl and hydroxy and $R^{57}$ and $R^{58}$ together with the carbon atoms to which they are attached form an aryl, substituted aryl, heteroaryl, substituted heteroaryl, cycloalkyl or substituted cycloalkyl ring. Preferably $R^{49}$, $R^{50}$, $R^{55}$ and $R^{56}$ are independently hydrogen or methyl and $R^{57}$ and $R^{58}$ together with the carbon atoms to which they are attached form a cyclopentenyl, cyclohexenyl, phenyl, furyl, thienyl, pyrrolyl, benzothienyl, benzofuryl, indolyl, pyridyl, quinolyl, imidazolyl or oxazolyl ring. More preferably, $R^{49}$, $R^{50}$, $R^{55}$ and $R^{56}$ are each independently hydrogen or methyl and $R^{57}$ and $R^{58}$ together with the carbon atoms to which they are attached form a phenyl ring. Even more preferably, $R^{49}$, $R^{50}$, $R^{55}$ and $R^{56}$ are hydrogen, and $R^{57}$ and $R^{58}$ together with the carbon atoms to which they are attached form a phenyl ring.

In one preferred embodiment, the compounds of Formula (IX) have the structures of Formulae (XXVII) and (XXVIII):

(XXVII)

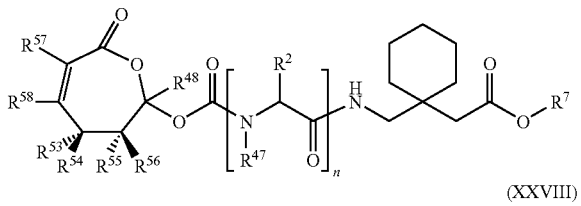

(XXVIII)

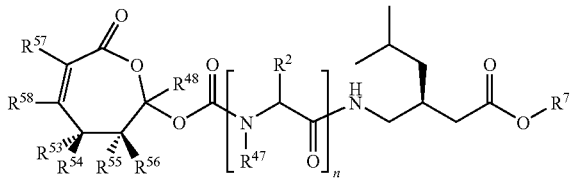

In a preferred embodiment of compounds of Formulae (XXVII) and (XXVIII), $R^7$ is hydrogen. In another preferred embodiment of compounds of Formulae (XXVII) and (XXVIII), n is 0. In still another embodiment of compounds of Formulae (XXVII) and (XXVIII), n is 1, $R^{47}$ is hydrogen and $R^2$ is hydrogen, methyl, 2-propyl, 2-butyl, isobutyl, t-butyl, cyclopentyl, cyclohexyl, phenyl, benzyl, 4-hydroxybenzyl, 2-imidazolyl, 2-indolyl, —CH$_2$OH, —CH(OH)CH$_3$, —CH$_2$CO$_2$H, —CH$_2$CH$_2$CO$_2$H, —CH$_2$CONH$_2$, —CH$_2$CH$_2$CONH$_2$, —CH$_2$CH$_2$SCH$_3$, —CH$_2$SH, —CH$_2$(CH$_2$)$_3$NH$_2$ or —CH$_2$CH$_2$CH$_2$NHC(NH)NH$_2$. In still another embodiment, n is 1 and $R^{47}$ and $R^2$ together with the atoms to which they are attached form a pyrrolidine ring.

In one embodiment of compounds of Formulae (XXVII) and (XXVIII), $R^{48}$ is selected from the group consisting of hydrogen, alkyl, substituted alkyl, alkoxycarbonyl, substituted alkoxycarbonyl, aryl, substituted aryl, arylalkyl, substituted arylalkyl, carbamoyl, cycloalkyl, substituted cycloalkyl, heteroaryl and substituted heteroaryl. Preferably, $R^{48}$ is hydrogen, methyl, ethyl, isopropyl, methoxycarbonyl, ethoxycarbonyl, isopropoxycarbonyl or phenyl. More preferably, $R^{48}$ is hydrogen.

In one embodiment of compounds of Formulae (XXVII) and (XXVIII), $R^{53}$, $R^{54}$, $R^{55}$ and $R^{56}$ are independently selected from the group consisting of hydrogen, alkyl, substituted alkyl, alkoxy, acyl, substituted acyl, acylamino, acyloxy, amino, alkylamino, alkoxycarbonyl, aryl, substituted aryl, arylalkyl, carbamoyl, cycloalkyl, substituted cycloalkyl, cycloheteroalkyl, substituted cycloheteroalkyl, dialkylamino, halo, heteroalkyl, heteroaryl and hydroxy and $R^{57}$ and $R^{58}$ are independently hydrogen, alkyl, substituted alkyl, acylamino, aryl, substituted aryl, arylalkyl, cycloalkyl, cycloheteroalkyl, heteroalkyl, substituted heteroalkyl, heteroaryl or substituted heteroaryl. Preferably, $R^{53}$, $R^{54}$, $R^{55}$ and $R^{56}$ are independently hydrogen, methyl, ethyl, phenyl, methoxy, ethoxy, amino, acetamido, benzamido, acetoxy, benzoyloxy or hydroxy and $R^{57}$ and $R^{58}$ are independently hydrogen, methyl, ethyl or phenyl.

In a preferred embodiment, $R^{53}$, $R^{54}$, $R^{55}$ and $R^{56}$ are independently hydrogen, methyl, ethyl, phenyl, methoxy, ethoxy, amino, acetamido, benzamido, acetoxy, benzoyloxy or hydroxy and $R^{57}$ and $R^{58}$ are hydrogen. In another preferred embodiment, $R^{53}$, $R^{54}$, $R^{55}$, $R^{56}$, $R^{57}$ and $R^{58}$ are hydrogen.

In yet another preferred embodiment of compounds of Formulae (XXVII) and (XXVIII), $R^{53}$, $R^{54}$, $R^{55}$ and $R^{56}$ are independently selected from the group consisting of hydrogen, alkyl, substituted alkyl, alkoxy, acyl, substituted acyl, acylamino, acyloxy, amino, alkylamino, alkoxycarbonyl, aryl, substituted aryl, arylalkyl, carbamoyl, cycloalkyl, substituted cycloalkyl, cycloheteroalkyl, substituted cycloheteroalkyl, dialkylamino, halo, heteroalkyl, heteroaryl and hydroxy and $R^{57}$ and $R^{58}$ together with the carbon atoms to which they are attached form an aryl, substituted aryl, heteroaryl, substituted heteroaryl, cycloalkyl or substituted cycloalkyl ring. Preferably, $R^{53}$, $R^{54}$, $R^{55}$ and $R^{56}$ are independently hydrogen or methyl and $R^{57}$ and $R^{58}$ together with the carbon atoms to which they are attached form a cyclopentenyl, cyclohexenyl, phenyl, furyl, thienyl, pyrrolyl, benzothienyl, benzofuryl, indolyl, pyridyl, quinolyl, imidazolyl or oxazolyl ring. More preferably, $R^{53}$, $R^{54}$, $R^{55}$ and $R^{56}$ are independently hydrogen or methyl and $R^{57}$ and $R^{58}$ together with the carbon atoms to which they are attached form a phenyl ring. Even more preferably, $R^{53}$, $R^{54}$, $R^{55}$ and $R^{56}$ are hydrogen, and $R^{57}$ and $R^{58}$ together with the carbon atoms to which they are attached form a phenyl ring.

4.3 Synthesis of the Compounds of the Invention

The compounds of the invention may be obtained via the synthetic methods illustrated in Schemes 1-11. Those of skill in the art will appreciate that a preferred synthetic route to the compounds of the invention will consist of attaching promoieties to GABA analogs. Numerous methods have been described in the art for the synthesis of GABA analogs (See, e.g., Satzinger et al., U.S. Pat. No. 4,024,175; Silverman et al., U.S. Pat. No. 5,563,175; Horwell et al., U.S. Pat. No. 6,020,370; Silverman et al., U.S. Pat. No. 6,028,214; Horwell et al., U.S. Pat. No. 6,103,932; Silverman et al., U.S. Pat. No. 6,117,906; Silverman, International Application No. WO 92/09560; Silverman et al., International Application No. WO 93/23383; Horwell et al., International Application No. WO 97/29101, Horwell et al., International Application No. WO 97/33858; Horwell et al., International Application No. WO 97/33859; Bryans et al., International Application No. WO 98/17627; Guglietta et al., International Application No. WO 99/08671; Bryans et al., International Application No. WO 99/21824; Bryans et al., International Application No. WO 99/31057; Belliotti et al., International Application No. WO 99/31074; Bryans et al., International Application No. WO 99/31075; Bryans et al., International Application No. WO 99/61424; Bryans et al., International Application No. WO 00/15611; Bryans, International Application No. WO 00/31020; and Bryans et al., International Application No. WO 00/50027). Other methods are known in the art for synthesizing GABA analogs, which are readily accessible to the skilled artisan. The promoieties described herein, are known in the art and may be prepared and attached to GABA analogs by established procedures (See e.g., Green et al., "Protective Groups in Organic Chemistry", (Wiley, $2^{nd}$ ed. 1991); Harrison et al., "Compendium of Synthetic Organic Methods", Vols. 1-8 (John Wiley and Sons, 1971-1996); "Beilstein Handbook of Organic Chemistry," Beilstein Institute of Organic Chemistry, Frankfurt, Germany; Feiser et al., "Reagents for Organic Synthesis," Volumes 1-17, Wiley Interscience; Trost et al., "Comprehensive Organic Synthesis," Pergamon Press, 1991; "Theilheimer's Synthetic Methods of Organic Chemistry," Volumes 1-45, Karger, 1991; March, "Advanced Organic Chemistry," Wiley Interscience, 1991; Larock "Comprehensive Organic Transformations," VCH Publishers, 1989; Paquette, "Encyclopedia of Reagents for Organic Synthesis," John Wiley & Sons, 1995, Bodanzsky, "Principles of Peptide Synthesis," Springer Verlag, 1984; Bodanzsky, "Practice of Peptide Synthesis," Springer Verlag, 1984).

Accordingly, starting materials useful for preparing compounds of the invention and intermediates thereof are commercially available or can be prepared by well-known synthetic methods. Other methods for synthesis of the prodrugs described herein are either described in the art or will be readily apparent to the skilled artisan in view of the references provided above and may be used to synthesize the compounds of the invention. Accordingly, the methods presented in the Schemes herein are illustrative rather than comprehensive.

In any of the Schemes below, after the amino group of a GABA analog has been functionalized with a promoiety or other protecting group, the carboxylic acid group may be converted to an ester or thioester by many synthetic methods, which are well-known to the skilled artisan. In one preferred embodiment, GABA analogs may be reacted with an alcohol or thiol in the presence of a coupling reagent (e.g., carbodiimide and dimethylaminopyridine) to provide the ester. In another preferred embodiment, GABA analogs may be reacted with an alkyl halide in the presence of base to yield the ester. Other methods for converting GABA analogs to esters or thioesters are well within the purview of the skilled artisan in view of the references provided herein.

One method for synthesis of compounds of Formulae (I)-(IX), where n is 0, involves the reaction of an appropriate lactol with a isocyanate derivative of a GABA analog, as illustrated specifically for the 5-membered compound of Formula (II) in Scheme 1. Note that other compounds (i.e., those of Formulae (III)-(X)) may be synthesized in a similar fashion from an appropriate lactol.

Scheme 1

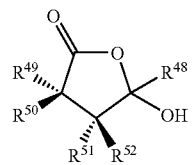

11

+

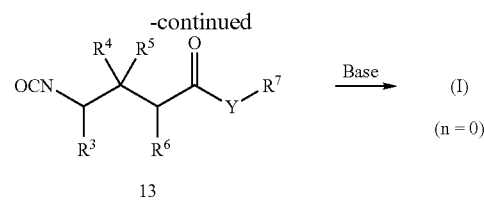

13

Lactol (11) is reacted with isocyanate (13) in an appropriate solvent (e.g. toluene) at a temperature between 0° C. and 120° C., preferably between 25° C. and 120° C., in the presence of a base (e.g., DBU, $Et_3N$, pyridine, DIEA, etc.) to afford a compound of Formula (II). Lactol (11) may be obtained from commercial sources or may be prepared by methods well known in the art. For example, addition of organometallic reagents (e.g., alkyl lithium, Grignard reagents) or hydride reagents (e.g., $LiAlH(O^tBu)_3$, $NaBH_4$, $LiAlH_4$ or $Na_2Fe(CO)_4$) to cyclic anhydride (15) provides lactol (11) as illustrated in Scheme 2.

Scheme 2

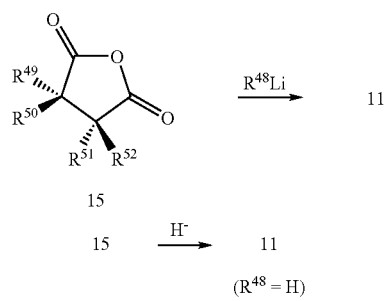

Five-membered lactols (11) and six-membered lactols (21) are also readily accessible by tautomerization of the α, γ-carboxyaldehydes (17) and α,δ-carboxyaldehydes (19) respectively, as shown in Scheme 3. Compounds (17) and (19) in turn are available by methods well known to the skilled artisan.

Scheme 3

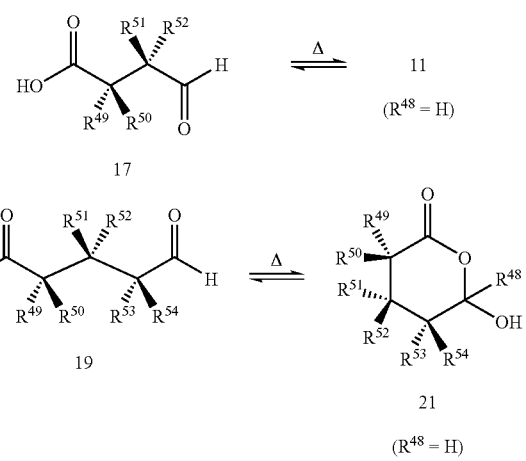

One method for preparation of isocyanate derivatives (13) begins with an appropriate six-membered anhydride (23) as illustrated in Scheme 4. The anhydride ring is opened by reaction with an alcohol or thiol nucleophile to afford carboxylic acid (25), which may be converted to an intermediate acyl azide in either a 2-step sequence (i.e., first activation of the carboxyl group as a mixed anhydride, acyl halide or synthetic equivalent and then displacement with azide) or directly (i.e., by treatment with $Ph_2P(O)N_3$). Curtius rearrangement of the acyl azide intermediate by thermolysis in an appropriate solvent (e.g., toluene) at a temperature between 0° C. and 120° C. affords isocyanate (13). Optionally, the isocyanate is not isolated but rather is generated in situ and quenched by reaction with lactol (11) to afford the desired product of Formula (II).

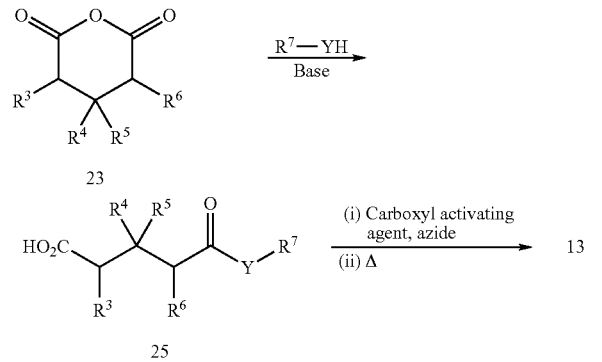

Another method for synthesis of compounds of Formulae (I)-(X) involves activation of an appropriate lactol by treatment with phosgene or its synthetic equivalent (27) (e.g., triphosgene, carbonyldiimidazole, p-nitrophenylchloroformate) to provide (29), which may be reacted with GABA analog derivative (31) to afford the desired product, as illustrated specifically for the 5-membered compound of Formula (II) in Scheme 5. Note that other compounds (of Formulae (III)-(X)) may be synthesized in a similar fashion from the appropriate lactol.

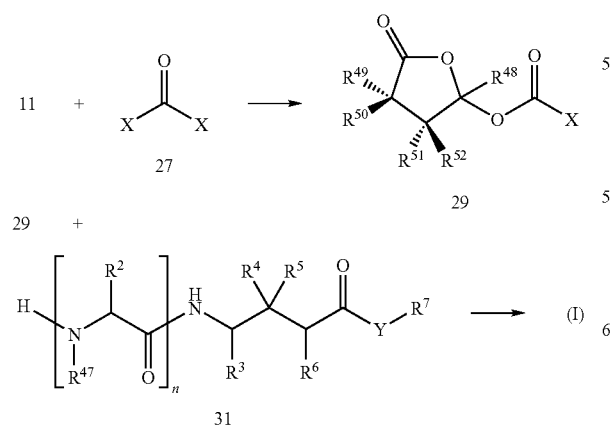

Alternatively compounds of Formulae (I)-(X) can be prepared from activated lactol (29) in a stepwise fashion as illustrated in Scheme 6. Here reaction of (29) with an α-amino acid, optionally protected as a carboxylate ester, affords intermediate (32), which upon deprotection, if necessary, provides compound (34). Compound (34) may be coupled to GABA analog (36) using standard peptide coupling reagents well known in the art.

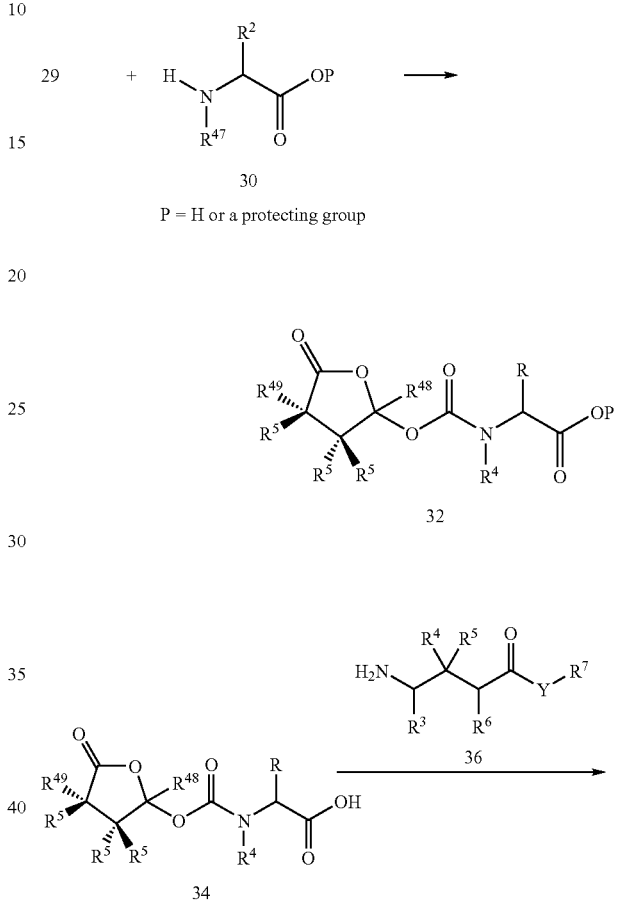

Another method for synthesis of compounds of Formulae (I)-(X) proceeds via carbonylation of GABA analog derivative (31) to an intermediate carbamic acid, which may be captured by an in situ alkylation (Butcher, Synlett, 1994, 825-6; Ferres et al., U.S. Pat. No. 4,036,829). Carbon dioxide gas may be added to a solution containing (31) and a base (e.g., $Cs_2CO_3$, $Ag_2CO_3$, AgO) in polar diprotic solvent (e.g., DMF, NMP). The activated halide may be added, optionally in the presence of iodide ion as a catalyst, to the solution and the reaction continued until complete. This method is illustrated in Scheme 7 for the preparation of compounds of Formula (II) and (V), from saturated and unsaturated halides (33) and (35), respectively. Compounds of Formula (III), (IV), (VI)-(X) may be similarly prepared from an appropriate cyclic halide.

Scheme 7

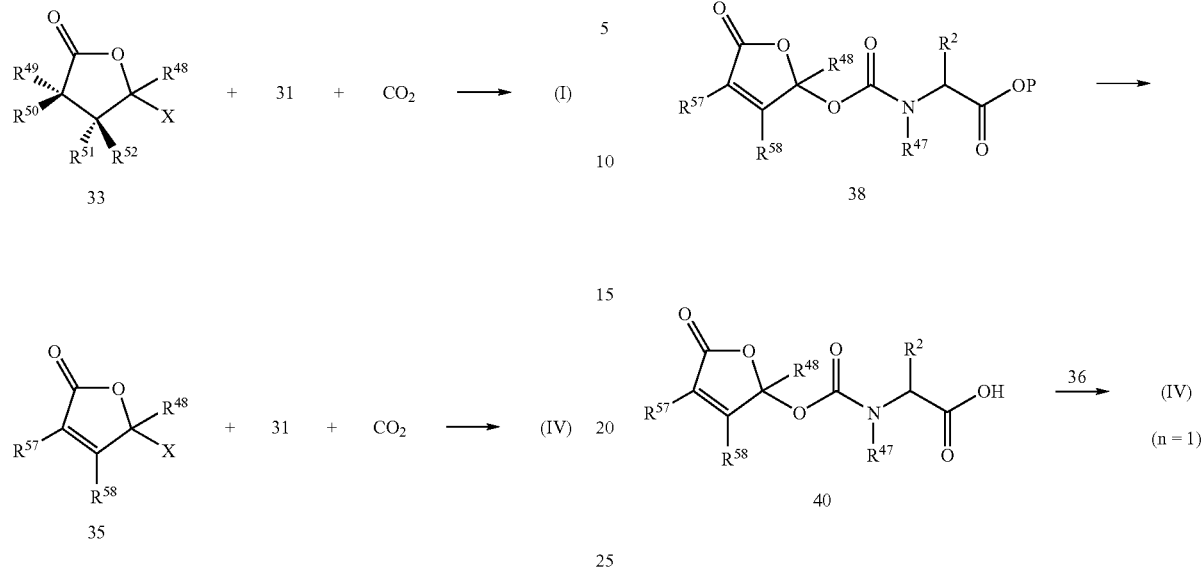

X = Cl, Br

Alternatively compounds of Formulae (I)-(X) may be prepared in a stepwise fashion as illustrated in Scheme 8. Carbonylation and alkylation of carboxyl protected α-amino acid (30) provides intermediates (32) and (38), which upon deprotection are coupled to GABA analog (36) as previously described in Scheme 6.

Scheme 8

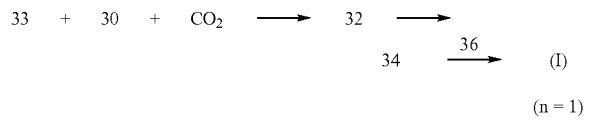

Another method for synthesis of compounds of Formulae (I)-(X) relies upon oxidation of ketocarbamate derivatives of GABA analogs, as disclosed in a copending U.S. patent application Ser. No. 10/167,797 entitled "Methods for Synthesis of Prodrugs from 1-Acyl-Alkyl Derivatives and Compositions." As illustrated in Scheme 9, oxidation of ketocarbamates (37) and (39) affords compounds of Formulae (III) and (IV). Preferred solvents for this reaction will dissolve, at least partially, both the oxidant and the ketocarbamate and will be inert to the reaction conditions. Preferred solvents include, but are not limited to, t-butanol, diethylether, acetic acid, hexane, dichloroethane, dichloromethane, ethyl acetate, acetonitrile, methanol, chloroform and water. Generally, the oxidant may be an organism (e.g., yeast or bacteria), or a chemical reagent (e.g., an enzyme or peroxide), and preferred oxidants include those, which have been successfully used in Baeyer-Villager oxidations of ketones to esters or lactones (Strukul, *Angnew. Chem. Int. Ed.,* 1998, 37, 1198; Renz et al., *Eur. J. Org. Chem.* 1999, 737; Beller et al., in "Transitions Metals in Organic Synthesis" Chapter 2, Wiley VCH; Stewart, *Current Organic Chemistry,* 1998, 2, 195; Kayser et al., *Synlett,* 1999, 1, 153).

Scheme 9

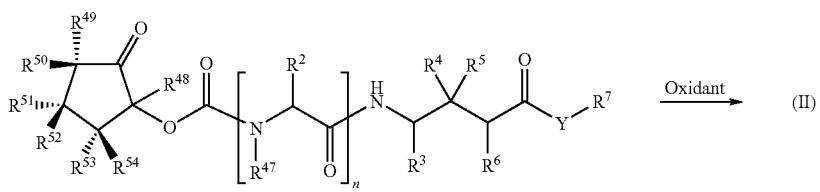

-continued

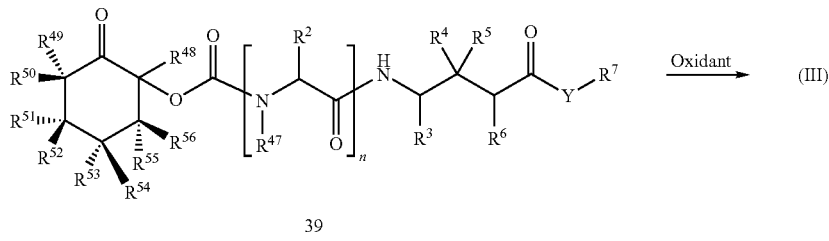

39

In one embodiment, the oxidant is yeast (e.g., *Saccharomyces cerevisiae*) or bacteria (e.g., *Acinetobacter* sp. NCIB 9871). In another embodiment, the oxidant is a peroxide (preferably, $H_2O_2$, t-BuOOH or $(TMS)_2O_2$) or a peroxyacid (preferably, $CF_3CO_3H$, $MeCO_3H$, m-CPBA, monopermaleic acid, mono-o-perphthalic acid, 3,5 dinitroperbenzoic acid, o-nitroperbenzoic acid, m-nitroperbenzoic acid, p-nitroperbenzoic acid, performic acid, perbenzoic acid, persulfuric acid, or a salt thereof). In still another embodiment, the oxidant is an enzyme and oxygen. Preferably, the enzyme is cyclohexanone monooxygenase.

Other compounds of the invention may also be prepared from an appropriate ketocarbamate derivative via Baeyer-Villiger oxidation. Preferably, as is well known to the skilled artisan, such compounds do not contain functional groups susceptible to decomposition or further transformation under the reaction conditions.

Ketocarbamates (37) and (39) may be prepared from the corresponding cyclic α-hydroxyketone compounds either directly, via reaction with isocyanate (13) (see Scheme 1 above), or by conversion of the α-hydroxyketone compound to a haloformate or activated carbonate intermediate and subsequent reaction with compound (31), as illustrated in Scheme 5. For cyclic α-hydroxyketones that are easily dimerized under normal conditions (e.g., lower 2-hydroxycycloalkanones) the keto moiety may be protected until carbamate formation is completed. For example, as shown in Scheme 10, dialkyl ketal (41) serves as a masked 2-hydroxycyclohexanone precursor, which may be converted to ketocarbamate (39) by acidic hydrolysis.

Scheme 10

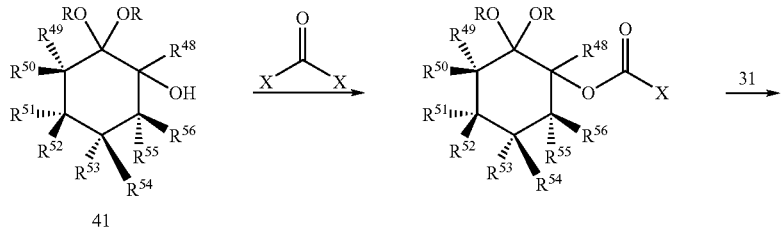

41

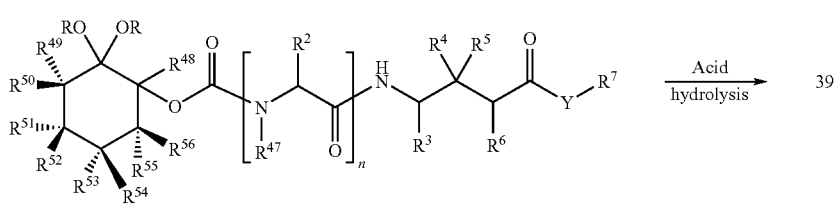

Alternatively ketocarbamate (39) can be prepared in a stepwise manner via the α-amino acid carbamate (43) as illustrated in Scheme 11, following the coupling methodologies used in Scheme 6 and 8.

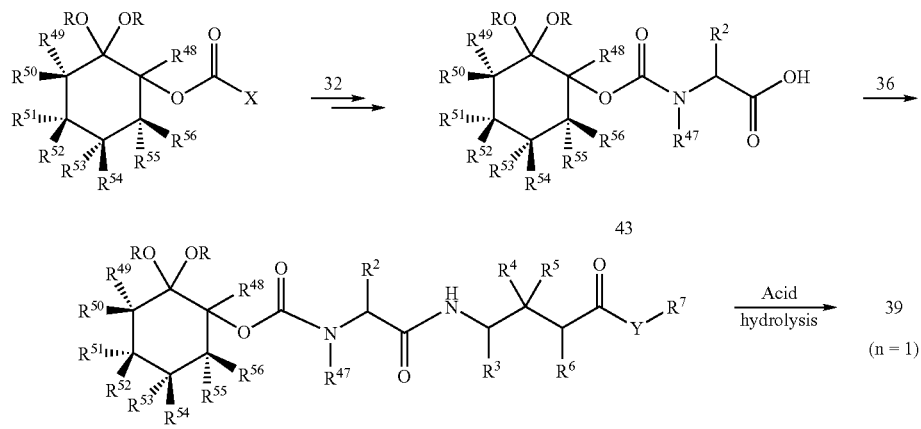

Scheme 11

4.4 Therapeutic Uses of the Compounds of the Invention

In accordance with the invention, a compound and/or composition of the invention is administered to a patient, preferably a human, suffering from epilepsy, depression, anxiety, psychosis, faintness attacks, hypokinesia, cranial disorders, neurodegenerative disorders, panic, pain (especially, neuropathic pain and muscular and skeletal pain), inflammatory disease (i.e., arthritis), insomnia, gastrointestinal disorders or ethanol withdrawal syndrome. Further, in certain embodiments, the compounds and/or compositions of the invention are administered to a patient, preferably a human, as a preventative measure against various diseases or disorders. Thus, the compounds and/or compositions of the invention may be administered as a preventative measure to a patient having a predisposition for epilepsy, depression, anxiety, psychosis, faintness attacks, hypokinesia, cranial disorders, neurodegenerative disorders, panic, pain (especially, neuropathic pain and muscular and skeletal pain), inflammatory disease (i.e., arthritis), insomnia, gastrointestinal disorders and ethanol withdrawal syndrome. Accordingly, the compounds and/or compositions of the invention may be used for the prevention of one disease or disorder and concurrently treating another (e.g., prevention of psychosis while treating gastrointestinal disorders; prevention of neuropathic pain while treating ethanol withdrawal syndrome).

The suitability of the compounds and/or compositions of the invention in treating epilepsy, depression, anxiety, psychosis, faintness attacks, hypokinesia, cranial disorders, neurodegenerative disorders, panic, pain (especially neuropathic pain and muscular and skeletal pain), inflammatory disease (i.e., arthritis), insomnia, gastrointestinal disorders and ethanol withdrawal syndrome may be determined by methods described in the art (See, e.g., Satzinger et al., U.S. Pat. No. 4,024,175; Satzinger et al., U.S. Pat. No. 4,087,544, Woodruff, U.S. Pat. No. 5,084,479; Silverman et al., U.S. Pat. No. 5,563,175; Singh, U.S. Pat. No. 6,001,876; Horwell et al., U.S. Pat. No. 6,020,370; Silverman et al., U.S. Pat. No. 6,028,214; Horwell et al., U.S. Pat. No. 6,103,932; Silverman et al., U.S. Pat. No. 6,117,906; Silverman, International Application No. WO 92/09560; Silverman et al., International Application No. WO 93/23383; Horwell et al., International Application No. WO 97/29101, Horwell et al., International Application No. WO 97/33858; Horwell et al., International Application No. WO 97/33859; Bryans et al., International Application No. WO 98/17627; Guglietta et al., International Application No. WO 99/08671; Bryans et al., International Application No. WO 99/21824; Bryans et al., International Application No. WO 99/31057; Magnus-Miller et al., International Application No. WO 99/37296; Bryans et al., International Application No. WO 99/31075; Bryans et al., International Application No. WO 99/61424; Pande, International Application No. WO 00/23067; Bryans, International Application No. WO 00/31020; Bryans et al., International Application No. WO 00/50027; and Bryans et al, International Application No. WO 02/00209). Procedures for using the compounds and/or compositions of the invention for treating epilepsy, depression, anxiety, psychosis, faintness attacks, hypokinesia, cranial disorders, neurodegenerative disorders, panic, pain (especially neuropathic pain and muscular and skeletal pain), inflammatory disease (i.e., arthritis), insomnia, gastrointestinal disorders and ethanol withdrawal syndrome have also been described in the art (see references above). Thus, it is well with the capability of those of skill in the art to assay and use the compounds and/or of the invention to treat epilepsy, depression, anxiety, psychosis, faintness attacks, hypokinesia, cranial disorders, neurodegenerative disorders, panic, pain (especially, neuropathic pain and muscular and skeletal pain), inflammatory disease i.e., arthritis), insomnia, gastrointestinal disorders and ethanol withdrawal syndrome.

4.5 Therapeutic/Prophylactic Administration

The compounds and/or compositions of the invention may be advantageously used in human medicine. As previously described in Section 4.4 above, compounds and compositions of the invention are useful for the treatment or prevention of epilepsy, depression, anxiety, psychosis, faintness attacks, hypokinesia, cranial disorders, neurodegenerative disorders, panic, pain (especially, neuropathic pain and muscular and skeletal pain), inflammatory disease (i.e., arthritis), insomnia, gastrointestinal disorders or ethanol withdrawal syndrome.

When used to treat or prevent the above disease or disorders compounds and/or compositions of the invention may be administered or applied singly, in combination with other agents. The compounds and/or compositions of the invention may also be administered or applied singly, in combination with other pharmaceutically active agents, including other compounds of the invention.

The current invention provides methods of treatment and prophylaxis by administration to a patient of a therapeutically effective amount of a composition or compound of the invention. The patient may be an animal, is more preferably a mammal, and most preferably a human.

The present compounds and/or compositions of the invention, which comprise one or more compounds of the invention, are preferably administered orally. The compounds and/or compositions of the invention may also be administered by any other convenient route, for example, by infusion or bolus injection, by absorption through epithelial or mucocutaneous linings (e.g., oral mucosa, rectal and intestinal mucosa, etc.). Administration can be systemic or local. Various delivery systems are known, (e.g., encapsulation in liposomes, microparticles, microcapsules, capsules, etc.) that can be used to administer a compound and/or composition of the invention. Methods of administration include, but are not limited to, intradermal, intramuscular, intraperitoneal, intravenous, subcutaneous, intranasal, epidural, oral, sublingual, intranasal, intracerebral, intravaginal, transdermal, rectally, by inhalation, or topically, particularly to the ears, nose, eyes, or skin.

In particularly preferred embodiments, the compounds of the invention can be delivered via sustained release systems, preferably oral sustained release systems. In one embodiment, a pump may be used (see Langer, supra; Sefton, 1987, *CRC Crit Ref Blamed Eng.* 14:201; Saudek et al., 1989, *N. Engl. J Med.* 321:574).

In another embodiment, polymeric materials can be used (see "Medical Applications of Controlled Release," Langer and Wise (eds.), CRC Pres., Boca Raton, Fla. (1974); "Controlled Drug Bioavailability," Drug Product Design and Performance, Smolen and Ball (eds.), Wiley, New York (1984); Ranger and Peppas, 1983, *J Macromol. Sci. Rev. Macromol Chem.* 23:61; see also Levy et al., 1985, *Science* 228: 190; During et al., 1989, *Ann. Neurol.* 25:351; Howard et al, 1989, *J. Neurosurg.* 71:105). In a preferred embodiment, polymeric materials are used for oral sustained release delivery. Preferred polymers include sodium carboxymethylcellulose, hydroxypropylcellulose, hydroxypropylmethylcellulose and hydroxyethylcellulose (most preferred, hydroxypropylmethylcellulose). Other preferred cellulose ethers have been described (Alderman, *Int. J. Pharm. Tech. & Prod. Mfr.*, 1984, 5(3) 1-9). Factors affecting drug release are well known to the skilled artisan and have been described in the art (Bamba et al., *Int. J. Pharm.*, 1979, 2, 307).

In another embodiment, enteric-coated preparations can be used for oral sustained release administration. Preferred coating materials include polymers with a pH-dependent solubility (i.e., pH-controlled release), polymers with a slow or pH-dependent rate of swelling, dissolution or erosion (i.e., time-controlled release), polymers that are degraded by enzymes (i.e., enzyme-controlled release) and polymers that form firm layers that are destroyed by an increase in pressure (i.e., pressure-controlled release).

In still another embodiment, osmotic delivery systems are used for oral sustained release administration (Verma et al., *Drug Dev. Ind. Pharm.*, 2000, 26:695-708). In a preferred embodiment, OROS™ osmotic devices are used for oral sustained release delivery devices (Theeuwes et al., U.S. Pat. No. 3,845,770; Theeuwes et al., U.S. Pat. No. 3,916,899).

In yet another embodiment, a controlled-release system can be placed in proximity of the target of the compounds and/or composition of the invention, thus requiring only a fraction of the systemic dose (see, e.g., Goodson, in "Medical Applications of Controlled Release," supra, vol. 2, pp. 115-138 (1984)). Other controlled-release systems discussed in Langer, 1990, *Science* 249:1527-1533 may also be used.

The compounds and/or compositions of the invention preferably provide GABA analogs (e.g., gabapentin and pregabalin) upon in vivo administration to a patient. While not wishing to bound by theory, the promoiety or promoieties of the compounds and/or compositions of the invention may be cleaved either chemically and/or enzymatically. One or more enzymes present in the stomach, intestinal lumen, intestinal tissue, blood, liver, brain or any other suitable tissue of a mammal may enzymatically cleave the promoiety or promoieties of the compounds and/or compositions of the invention. The mechanism of cleavage is not important to the current invention. Preferably, GABA analogs formed by cleavage of prodrugs from the compounds of the invention do not contain substantial quantities of lactam contaminant (preferably, less than 0.5% by weight, more preferably, less than 0.2% by weight, most preferably less than 0.1% by weight). The extent of release of lactam contaminant from the prodrugs of this invention may be assessed using the standard in vitro analytical methods.

While not wishing to bound by theory, the promoiety or promoieties of the compounds and/or compositions of the invention may be cleaved prior to absorption by the gastrointestinal tract (e.g., within the stomach or intestinal lumen) and/or after absorption by the gastrointestinal tract (e.g., in intestinal tissue, blood, liver or other suitable tissue of a mammal). If the promoiety or promoieties of the compounds of the invention are cleaved prior to absorption by the gastrointestinal tract, the resulting GABA analogs may be absorbed into the systemic circulation conventionally (e.g., via the large neutral amino acid transporter located in the small intestine). If the promoiety or promoieties of the compounds of the invention are cleaved after absorption by the gastrointestinal tract, these GABA analog prodrugs may have the opportunity to be absorbed into the systemic circulation either by passive diffusion, active transport or by both passive and active processes.

If the promoiety or promoieties of the compounds of the invention are cleaved after absorption by the gastrointestinal tract, these GABA analog prodrugs may have the opportunity to be absorbed into the systemic circulation from the large intestine. In this situation, the compounds and/or compositions of the invention are preferably administered as sustained release systems. In a preferred embodiment, the compounds of the invention are delivered by oral sustained release administration. Preferably, in this embodiment, the compounds of the invention are administered twice per day (more preferably, once per day).

4.6 Compositions of the Invention

The present compositions contain a therapeutically effective amount of one or more compounds of the invention, preferably in purified form, together with a suitable amount of a pharmaceutically acceptable vehicle, which so as to provide the form for proper administration to a patient. When administered to a patient, the compounds of the invention and pharmaceutically acceptable vehicles are preferably sterile. Water is a preferred vehicle when the compound of the invention is administered intravenously. Saline solutions and aqueous dextrose and glycerol solutions can also be employed as liquid vehicles, particularly for injectable solutions. Suitable pharmaceutical vehicles also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The present compositions, if desired, can also contain minor amounts of wetting or emulsifying agents, or pH buffering agents. In addition, auxiliary, stabilizing, thickening, lubricating and coloring agents may be used.

In one embodiment, the compositions of the invention are free of lactam side products formed by intramolecular cyclization. In a preferred embodiment, the compositions of the invention are stable to extended storage (preferably, greater than one year) without substantial lactam formation (preferably, less than 0.5% lactam by weight, more preferably, less than 0.2% lactam by weight, most preferably, less than 0.1% lactam by weight).

Pharmaceutical compositions comprising a compound of the invention may be manufactured by means of conventional mixing, dissolving, granulating, dragee-making, levigating, emulsifying, encapsulating, entrapping or lyophilizing processes. Pharmaceutical compositions may be formulated in conventional manner using one or more physiologically acceptable carriers, diluents, excipients or auxiliaries, which facilitate processing of compounds of the invention into preparations which can be used pharmaceutically. Proper formulation is dependent upon the route of administration chosen.

The present compositions can take the form of solutions, suspensions, emulsion, tablets, pills, pellets, capsules, capsules containing liquids, powders, sustained-release formulations, suppositories, emulsions, aerosols, sprays, suspensions, or any other form suitable for use. In one embodiment, the pharmaceutically acceptable vehicle is a capsule (see e.g., Grosswald et al., U.S. Pat. No. 5,698,155). Other examples of suitable pharmaceutical vehicles have been described in the art (see Remington's Pharmaceutical Sciences, Philadelphia College of Pharmacy and Science, 17th Edition, 1985). Preferred compositions of the invention are formulated for oral delivery, particularly for oral sustained release administration.

Compositions for oral delivery may be in the form of tablets, lozenges, aqueous or oily suspensions, granules, powders, emulsions, capsules, syrups, or elixirs, for example. Orally administered compositions may contain one or more optionally agents, for example, sweetening agents such as fructose, aspartame or saccharin; flavoring agents such as peppermint, oil of wintergreen, or cherry coloring agents and preserving agents, to provide a pharmaceutically palatable preparation. Moreover, where in tablet or pill form, the compositions may be coated to delay disintegration and absorption in the gastrointestinal tract, thereby providing a sustained action over an extended period of time. Selectively permeable membranes surrounding an osmotically active driving compound are also suitable for orally administered compounds of the invention. In these later platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time delay material such as glycerol monostearate or glycerol stearate may also be used. Oral compositions can include standard vehicles such as mannitol, lactose, starch, magnesium stearate, sodium saccharine, cellulose, magnesium carbonate, etc. Such vehicles are preferably of pharmaceutical grade.

For oral liquid preparations such as, for example, suspensions, elixirs and solutions, suitable carriers, excipients or diluents include water, saline, alkyleneglycols (e.g., propylene glycol), polyalkylene glycols (e.g., polyethylene glycol) oils, alcohols, slightly acidic buffers between pH 4 and pH 6 (e.g., acetate, citrate, ascorbate at between about 5 mM to about 50 mM) etc. Additionally, flavoring agents, preservatives, coloring agents, bile salts, acylcarnitines and the like may be added.

Compositions for administration via other routes may also be contemplated. For buccal administration, the compositions may take the form of tablets, lozenges, etc. formulated in conventional manner. Liquid drug formulations suitable for use with nebulizers and liquid spray devices and EHD aerosol devices will typically include a compound of the invention with a pharmaceutically acceptable vehicle. Preferably, the pharmaceutically acceptable vehicle is a liquid such as alcohol, water, polyethylene glycol or a perfluorocarbon. Optionally, another material may be added to alter the aerosol properties of the solution or suspension of compounds of the invention. Preferably, this material is liquid such as an alcohol, glycol, polyglycol or a fatty acid. Other methods of formulating liquid drug solutions or suspension suitable for use in aerosol devices are known to those of skill in the art (see, e.g., Biesalski, U.S. Pat. No. 5,112,598; Biesalski, U.S. Pat. No. 5,556,611). A compound of the invention may also be formulated in rectal or vaginal compositions such as suppositories or retention enemas, e.g., containing conventional suppository bases such as cocoa butter or other glycerides. In addition to the formulations described previously, a compound of the invention may also be formulated as a depot preparation. Such long acting formulations may be administered by implantation (for example, subcutaneously or intramuscularly) or by intramuscular injection. Thus, for example, a compound of the invention may be formulated with suitable polymeric or hydrophobic materials (for example, as an emulsion in an acceptable oil) or ion exchange resins, or as sparingly soluble derivatives, for example, as a sparingly soluble salt.

When a compound of the invention is acidic, it may be included in any of the above-described formulations as the free acid, a pharmaceutically acceptable salt, a solvate or hydrate. Pharmaceutically acceptable salts substantially retain the activity of the free acid, may be prepared by reaction with bases and tend to be more soluble in aqueous and other protic solvents than the corresponding free acid form.

4.7 Methods of Use and Doses

A compound of the invention, or compositions thereof, will generally be used in an amount effective to achieve the intended purpose. For use to treat or prevent diseases or disorders such as epilepsy, depression, anxiety, psychosis, faintness attacks, hypokinesia, cranial disorders, neurodegenerative disorders, panic, pain (especially, neuropathic pain and muscular and skeletal pain), inflammatory disease (i.e., arthritis), insomnia, gastrointestinal disorders or ethanol withdrawal syndrome the compounds of the invention or compositions thereof, are administered or applied in a therapeutically effective amount.

The amount of a compound of the invention that will be effective in the treatment of a particular disorder or condition disclosed herein will depend on the nature of the disorder or condition, and can be determined by standard clinical techniques known in the art as previously described. In addition, in vitro or in vivo assays may optionally be employed to help identify optimal dosage ranges. The amount of a compound of the invention administered will, of course, be dependent on, among other factors, the patient being treated, the weight of the patient, the severity of the affliction, the manner of administration and the judgment of the prescribing physician.

For example, the dosage may be delivered in a pharmaceutical composition by a single administration, by multiple applications or controlled release. In a preferred embodiment, the compounds of the invention are delivered by oral sustained release administration. Preferably, in this embodiment, the compounds of the invention are administered twice per day (more preferably, once per day). Dosing may be repeated intermittently, may be provided alone or in combination with other drugs and may continue as long as required for effective treatment of the disease state or disorder.

Suitable dosage ranges for oral administration are dependent on the potency of the parent GABA analog drug, but are generally about 0.001 mg to about 200 mg of a compound of the invention per kilogram body weight. When the GABA analog is gabapentin, typical daily doses of the parent drug in adult patients are 900 mg/day to 3600 mg/day and the dose of gabapentin prodrug may be adjusted to provide an equivalent molar quantity of gabapentin. Other GABA analogs may be more potent than gabapentin (e.g., pregabalin), and lower doses may be appropriate for both the parent drug and any prodrug (measured on an equivalent molar basis). Dosage ranges may be readily determined by methods known to the skilled artisan.

The compounds of the invention are preferably assayed in vitro and in vivo, for the desired therapeutic or prophylactic activity, prior to use in humans. For example, in vitro assays can be used to determine whether administration of a specific compound of the invention or a combination of compounds of the invention is preferred for reducing convulsion. The compounds of the invention may also be demonstrated to be effective and safe using animal model systems.

Preferably, a therapeutically effective dose of a compound of the invention described herein will provide therapeutic benefit without causing substantial toxicity. Toxicity of compounds of the invention may be determined using standard pharmaceutical procedures and may be readily ascertained by the skilled artisan. The dose ratio between toxic and therapeutic effect is the therapeutic index. A compound of the invention will preferably exhibit particularly high therapeutic indices in treating disease and disorders. The dosage of a compound of the inventions described herein will preferably be within a range of circulating concentrations that include an effective dose with little or no toxicity.

4.8. Combination Therapy

In certain embodiments of the present invention, the compounds of the invention can be used in combination therapy with at least one other therapeutic agent. The compound of the invention and the therapeutic agent can act additively or, more preferably, synergistically. In a preferred embodiment, a composition comprising a compound of the invention is administered concurrently with the administration of another therapeutic agent, which can be part of the same composition as the compound of the invention or a different composition. In another embodiment, a composition comprising a compound of the invention is administered prior or subsequent to administration of another therapeutic agent.

5. EXAMPLES

The invention is further defined by reference to the following examples, which describe in detail preparation of compounds and compositions of the invention and assays for using compounds and compositions of the invention. It will be apparent to those skilled in the art that many modifications, both to materials and methods, may be practiced without departing from the scope of the invention.

In the examples below, the following abbreviations have the following meanings. If an abbreviation is not defined, it has its generally accepted meaning.

| | |
|---|---|
| Atm = | atmosphere |
| Boc = | tert-butyloxycarbonyl |
| Cbz = | carbobenzyloxy |
| CPM = | counts per minute |
| DCC = | dicyclohexylcarbodiimide |
| DMAP = | 4-N,N-dimethylaminopyridine |
| DMEM = | Dulbecco's minimum eagle medium |
| DMF = | N,N-dimethylformamide |
| DMSO = | dimethylsulfoxide |
| Fmoc = | 9-fluorenylmethyloxycarbonyl |
| g = | gram |
| h = | hour |
| HBSS = | Hank's buffered saline solution |
| L = | liter |
| LC/MS = | liquid chromatography/mass spectroscopy |
| M = | molar |
| min = | minute |
| mL = | milliliter |
| mmol = | millimoles |
| MRM = | multiple reaction monitoring |
| NADPH = | reduced nicotinamide adenine dinucleotide phosphate |
| NHS = | N-hydroxysuccinimide |
| PBS = | phosphate buffered saline |
| THF = | tetrahydrofuran |
| TFA = | trifluoroacetic acid |
| TMS = | trimethylsilyl |
| μL = | microliter |
| μM = | micromolar |
| v/v = | volume to volume |

5.1 Example 1

Preparation of 1-{{[(ε-Caprolacton-6-yl)oxy]carbonyl}aminomethyl}-1-Cyclohexane Acetic Acid (44)

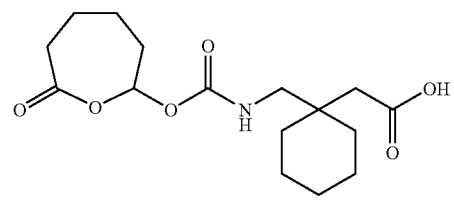

Step A: 2,2-Dimethoxycyclohex-1-yl Chloroformate (45)

To a stirred solution of 2,2'-dimethoxycyclohexanol (1.49 mL, 10 mmol) in dichloromethane (25 mL) under nitrogen atmosphere at 0° C. was added pyridine (1.21 mL, 15 mmol) followed by a solution of triphosgene (1.48 g, 5 mmol) in dichloromethane (25 mL). The reaction mixture was stirred at 0° C. for 30 minutes to provide compound 45 which was used in the next step without further purification.

Step B: 1-{{[(Cyclohexanon-2-yl)oxy]carbonyl}aminomethyl}-1-Cyclohexane Acetic Acid (46)

To a stirred solution of gabapentin (2.56 g, 15 mmol) and chlorotrimethylsilane (3.7 mL, 30 mmol) in dichloromethane (25 mL) at 0° C. under nitrogen atmosphere was added triethylamine in portions. After having stirred for 15 min at 0° C. the chloroformate (45) was added dropwise into the reaction mixture. The mixture was stirred at 0° C. for 2 h and then at room temperature for 2 h (monitored by TLC). The reaction mixture was concentrated in vacuo and the residue was poured into cold water (50 mL) and then acidified to about pH 5.0 using 0.1 N HCl. The crude product was then extracted using ethyl acetate (2×50 mL). The combined extracts were washed with brine (40 mL), dried over MgSO$_4$ and the solvent removed in vacuo. The crude product was dissolved in acetone (25 mL) and treated using Amberlyst-15 (1.0 g) for 1.5 h (monitored by LC/MS). The reaction mixture was filtered and the filtercake was washed with acetone (2×15 mL). The combined extracts were evaporated under reduced pressure and the residue was purified using prep-HPLC/MS method to provide 1.71 g (55% yield) of compound 46 as a white solid. $^1$H NMR (CDCl$_3$, 400 MHz): 5.42 (1H, t), 5.12 (1H, m), 3.35-3.16 (2H, m), 2.39 (4H, m), 1.80-1.40 (16H, m). MS (ESI): m/z=310.27 (M−H$^-$), and 312.28 (M+H$^+$).

Step C: 1-{{[(ε-Caprolacton-6-yl)oxy]carbonyl}aminomethyl}-1-Cyclohexane Acetic Acid (44)

To a stirred solution of (46) (0.31 g, 1 mmol) in dichloromethane (10 mL) was added mCPBA (0.68 g, 4 mmol) and Na$_2$HPO$_4$ (0.56 g, 4 mmol). The mixture was stirred at room temperature for 12 h (monitored by LC/MS), then concentrated in vacuo. The resulting residue was dissolved in water and then acidified to about pH 5.0 using 0.1N HCl. The aqueous solution was extracted using ethyl acetate (3×25 mL). The combined extracts were washed with brine (50 mL), dried over Na$_2$SO$_4$ and concentrated in vacuo. The resulting residue was purified using prep-HPLC/MS to provide 0.27 g (85%) of compound 44 as light yellow viscous liquid. $^1$H NMR (CDCl$_3$, 400 MHz): δ 6.40 (1H, m); 5.65 (1H, t); 3.31-3.25 (2H, m); 2.40-2.22 (4H, m); 1.60-1.30 (16H, m). MS (ESI): m/z=326.18 (M−H$^-$), 328.26 (M+H$^+$).

5.2 Example 2

Preparation of 1-{{[(δ-Valerolacton-2(R)-yl)oxy]carbonyl}aminomethyl}-1-Cyclohexane Acetic Acid (47)

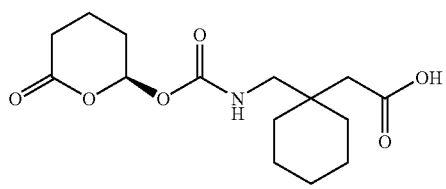

47

Step A: 1-{{{[2(R)-Acetoxycyclopent-1(R)-yl]oxy}carbonyl}aminomethyl}-1-Cyclohexane Acetic Acid (48)

To a stirred solution of (1R,2R)-trans-2-acetoxy-1-cyclopentanol (1.0 g, 6.9 mmol) in dichloromethane (25 mL) at 0° C. under nitrogen atmosphere was added pyridine (0.88 mL, 10.4 mmol) followed by a solution of triphosgene (1.03 g, 3.5 mmol) in dichloromethane (25 mL). The reaction mixture was stirred at 0° C. for 30 min. to provide the corresponding 2(R)-acetoxycyclopent-1(R)-yl chloroformate which was carried to next step without further purification.

In a separate reaction flask, to a stirred solution of gabapentin (1.8 g, 10 mmol) and triethylamine (4.3 mL, 31 mmol) in dichloromethane (100 mL) at 0° C. under nitrogen atmosphere, was added dropwise a solution of chlorotrimethylsilane (2.6 mL, 21 mmol) in dichloromethane (10 mL). After stirring for 30 min at 0° C., 2(R)-acetoxycyclopent-1(R)-yl chloroformate was added dropwise into the reaction mixture. The resulting mixture was stirred at 0° C. for 2 h and then at room temperature for 2 h (monitored by TLC). The reaction mixture was then concentrated in vacuo and the resulting residue was poured into cold water (50 mL), acidified to about pH 5.0 using 0.1 N HCl, then extracted using ethyl acetate (2×50 mL). The combined extracts were washed with brine (40 mL), dried over MgSO$_4$ and concentrated in vacuo. The crude product was purified using flash chromatography on silica gel using hexane/ethyl acetate (2:1) as eluant to afford 2.0 g (84%) of compound 48 as a colorless oil. $^1$H NMR (400 MHz, CDCl$_3$): δ1.31-1.78 (14H, m); 2.03-2.04 (5H, m); 2.31 (2H, s); 3.20 (2H, t, J=6.4 Hz); 5.07-4.97 (2H, m), 5.20 (1H, broad s). MS (ESI): m/z=340.25 (M−H$^-$).

Step B: 1-{{{[2(R)-Hydroxycyclopent-1(R)-yl]oxy}carbonyl}aminomethyl}-1-Cyclohexane Acetic Acid (49)

To a stirred solution of compound (48) (2.0 g, 5.9 mmol) in methanol (25 mL) was added a solution of NaOH (0.8 g, 20 mmol) in 20 mL of water. The reaction mixture was stirred at room temperature for 2 h (monitored by TLC). The reaction mixture was acidified to about pH 5.0 using 0.1 N HCl and then extracted using ethyl acetate (2×50 mL). The combined extracts were washed with brine (40 mL), dried over MgSO$_4$ and concentrated in vacuo. The crude product was purified using flash chromatography on silica gel using hexane/ethyl acetate (1:1) as eluant to provide 1.3 g (75%) of compound (49) as a colorless oil. $^1$H NMR (400 MHz, CDCl$_3$): δ1.36-1.78 (14H, m); 1.99-2.12 (2H, m); 2.34 (2H, s); 3.23 (2H, d, J=6.4 Hz); 4.09 (1H, m); 5.26 (1H, t, J=6.4 Hz); 5.89 (1H, m). MS (ESI): m/z=298.23 (M−H$^-$).

Step C: Benzyl 1-{{{[2(R)-Hydroxycyclopent-1(R)-yl]oxy}carbonyl}aminomethyl}-1-Cyclohexane Acetate (50)

To a stirred solution of compound (49) (0.5 g, 1.67 mmol), 1,3-dicyclohexylcarbodiimide (1.0 g, 5.0 mmol) and DMAP (19 mg, 0.16 mmol) in dichloromethane (100 mL) at room temperature under nitrogen atmosphere was added benzyl alcohol (1.1 mL, 10 mmol). The reaction mixture was stirred at room temperature for 15 h (monitored by tlc and LC/MS), then filtered, and the white solid was washed with dichloromethane (2×15 mL). The combined filtrates were washed with water (2×25 mL), dried over Na$_2$SO$_4$ and concentrated in vacuo. The crude product was purified using flash chromatography on silica gel using hexane/ethyl acetate (2:1) as eluant to provide 0.51 g (78%) of compound (50) as a colorless liquid. $^1$H NMR (400 MHz, CDCl$_3$): δ1.36-1.75 (14H, m); 1.99-2.10 (2H, m); 2.35 (2H, s); 3.17 (2H, d, J=6.8 Hz); 4.05 (1H, m); 4.65 (1H, m); 5.12 (2H, s); 5.34 (1H, t, J=6.8 Hz); 7.36 (5H, m). MS (ESI): m/z=390.22 (M+H$^+$).

Step D: Benzyl 1-{{{[2-Oxo-cyclopent-1(R)-yl]oxy}carbonyl}aminomethyl}-1-Cyclohexane Acetate (51)

To a stirred solution of compound (50) (0.50 g, 1.3 mmol) in dichloromethane (15 mL) was added pyridinium chlorochromate (0.55 g, 2.6 mmol) followed by NaOAc (0.21 g, 2.57 mmol) at room temperature. The resulting reaction was stirred overnight at room temperature (monitored by LC/MS), then filtered. The solid was washed with dichloromethane (2×25 mL) and the combined filtrates were washed with water (2×25 mL), dried over MgSO$_4$ and concentrated in vacuo to provide compound 51 which was used in the next step without further purification. MS (ESI): m/z=388.38 (M+H$^+$).

Step E: Benzyl 1-{{{(δ-valerolacton-2(R)-yl)oxy]carbonyl}aminomethyl}-1-Cyclohexane Acetate (52)

To a stirred solution of compound (51) (0.50 g, 1.2 mmol) in dichloromethane (20 mL) was added 3-chloroperoxybenzoic acid (0.82 g, 4.8 mmol) and Na$_2$HPO$_4$ (0.68 g, 4.8 mmol). The resulting reaction was stirred at room temperature for 12 h (monitored by LC/MS), then concentrated in vacuo and the resulting residue was dissolved in water and acidified to about pH 5.0 using 0.1N HCl. The reaction mixture was extracted using ethyl acetate (3×25 mL), and the combined extracts were washed with brine (50 mL), dried over Na$_2$SO$_4$ and concentrated in vacuo. The resulting residue was purified using preparative-HPLC/MS to afford 0.20 g (41%) of compound (52) as a colorless oil. $^1$H NMR (400 MHz, CDCl$_3$): δ1.32-1.60 (10H, m); 1.82-1.92 (2H, m); 2.00-2.11 (2H, m); 2.36 (2H, s); 2.52-2.67 (2H, m); 3.20 (2H, m); 5.20 (2H, s); 5.49 (1H, broad t), 6.50 (1H, t, J=4.0 Hz); 7.32-7.40 (5H, m). MS (ESI): m/z=404.22 (M+H$^+$).

Step F: 1-{{{(δ-Valerolacton-2(R)-yl)oxy]carbonyl}aminomethyl}-1-Cyclohexane Acetic Acid (47)

To a stirred solution of benzyl ester (52) (0.17 g, 0.42 mmol) in ethyl acetate (5 mL) was added 50 mg of 5% w/w palladium on carbon (Pd/C). The resulting reaction was stirred overnight at room temperature under a hydrogen atmosphere (monitored by LC/MS). The reaction mixture was then filtered through a Celite® pad and the pad was washed with ethyl acetate (2×10 mL). The combined filtrates were concentrated in vacuo to afford 0.12 g (99%) of compound (47) as a white solid. $^1$HNMR (400 MHz, CDCl$_3$): δ1.40-1.54 (10H, m); 1.84-1.92 (2H, m); 2.00-2.13 (2H, m); 2.35 (2H, s); 2.52-2.67 (2H, m); 3.26 (2H, d, J=6.4 Hz); 5.39 (1H, t, J=6.4 Hz); 6.51 (1H, t, J=4 Hz). MS (ESI): m/z=312.26 (M−H$^−$).

5.3 Example 3

Preparation of 1-{{[(3-Oxo-1,3-dihydro-isobenzofuran-1-yl)-oxy]carbonyl}aminomethyl}-1-Cyclohexane Acetic Acid (53)

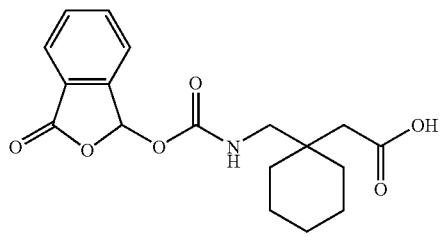

53

Step A: (1-Allyloxycarbonylmethyl-1-Cyclohexane Acetic Acid (54)

To a stirred suspension of sodium hydride (0.84 g, 35 mmol) in dry tetrahydrofuran (200 mL) under nitrogen atmosphere at 0° C. was added allyl alcohol (2.0 mL, 30 mmol) dropwise. The resulting reaction was stirred at 0° C. for 30 min and then at room temperature for 2 hours. A solution of 3-oxa-spiro[5,5]undecane-2,3-dione (4.5 g, 25 mmol) in dry tetrahydrofuran (10 mL) was then added dropwise to the reaction mixture at 0° C. The resulting reaction was stirred at 0° C. for 30 min, at room temperature for 3 h (monitored by TLC and LC/MS), and then concentrated in vacuo. The resulting residue was poured into a saturated aqueous NH$_4$Cl solution (100 mL) and the resulting mixture was extracted using ethyl acetate (2×100 mL). The combined extracts were washed with brine (100 mL), dried over MgSO$_4$ and concentrated in vacuo. The resulting residue was purified using flash chromatography on silica gel using hexane/ethyl acetate (4:1) as eluant to afford 3.2 g of compound (54) as a colorless liquid in (50% yield). $^1$H NMR (400 MHz, CDCl$_3$): δ1.50 (10H, m); 2.58 (4H, broad s); 4.57-4.59 (2H, m); 5.21-5.25 (1H, m); 5.29-5.35 (1H, m); 5.86-5.96 (1H, m). MS (ESI): m/z=239.29 (M−H$^−$).

Step B: 1-{{[(3-Oxo-1,3-dihydro-isobenzofuran-1-yl)-oxy]carbonyl}aminomethyl}-1-Cyclohexane Acetic Acid Allyl Ester (55)

To a stirred solution of (54) (3.2 g, 12 mmol) and ethyl chloroformate (1.4 mL, 15 mmol) in dry tetrahydrofuran (50 mL) at 0° C. under nitrogen atmosphere was added triethylamine (2.1 mL, 15 mmol) dropwise and the resulting reaction was allowed to stir for 15 min. A solution of sodium azide (1.95 g, 30 mmol) in water (10 mL) was added and the resulting reaction was stirred for 1 h (monitored by tlc), then poured into cold water (25 mL) and extracted using toluene (2×100 mL). The combined extracts were washed with brine (100 mL), dried over MgSO$_4$ and filtered. The resulting solution was then heated at refluxed (~110° C.) for 4 h to provide an isocyanate intermediate that was used in the next step without further purification.

To a stirred solution of the isocyanate intermediate in toluene from above at room temperature was added 2-carboxybenzaldehyde (1.8 g, 12 mmol) and the resulting reaction was allowed to stir at reflux for 15 h (monitored by tlc). The reaction mixture was cooled to room temperature, concentrated in vacuo, and the resulting residue was purified using flash chromatography on silica gel using hexane/ethyl acetate (2:1) as eluant to provide 1.2 g of compound (55) as a white solid (25% yield). $^1$H NMR (400 MHz, CDCl$_3$): δ1.39-1.55 (10H, m); 2.34 (2H, s); 3.20-3.38 (2H, m); 4.56 (2H, d, J=6.0 Hz); 5.33-5.22 (2H, m); 5.64 (1H, t, J=6.8 Hz); 5.84-5.94 (1H, m); 7.43 (1H, s); 7.60-7.66 (2H, dd, J=7.6 Hz); 7.74 (1H, t, J=7.6 Hz); 7.93 (1H, d, J=7.6 Hz). MS (ESI): m/z=388.36 (M+H$^+$).

Step C: 1-{{[(3-Oxo-1,3-dihydro-isobenzofuran-1-yl)-oxy]carbonyl}aminomethyl}-1-Cyclohexane Acetic Acid (53)

To a stirred solution of (55) (0.12 g, 0.31 mmol) in dry tetrahydrofuran was added tetrakis(triphenylphosphine)-palladium(0) (5.5 mg, 4.8×10$^{-3}$ mmol) and formic acid (57 mg, 1.24 mmol). The resulting reaction was stirred at room temperature for 12 h (monitored by LC/MS), then filtered through a Celite® and activated charcoal pad. The pad was washed with ethyl acetate (2×15 mL) and the combined filtrates were washed with brine (20 mL), dried over MgSO$_4$ and concentrated in vacuo. The resulting residue was purified using preparative-LC/MS to provide 80 mg of compound (53) as a white solid (74% yield). $^1$H NMR (400 MHz, CDCl$_3$) δ1.35-1.58 (10H, m); 2.34 (2H, s); 3.23-3.40 (2H, m); 5.56 (1H, t, J=7.2 Hz); 7.42 (1H, s); 7.60-7.66 (2H, dd, J=7.6 Hz); 7.74 (1H, t, J=7.6 Hz); 7.91 (1H, d, J=7.6 Hz). MS (ESI): m/z=346.40 (M+H$^+$).

5.4 Example 4

Standard Methods for Determination of Enzymatic Cleavage of Prodrugs in Vitro

The stability of novel prodrugs is evaluated in one or more in vitro systems using tissues representative of those encountered in vivo (i.e., intestinal luminal contents, small intestinal cells, blood, liver, etc.) following methods known in the art. Tissues may be obtained from any vertebrate species but most commonly are obtained from mouse, rat, hamster, guinea pig, rabbit, pig, dog, monkey or human sources. Fractions, homogenates, supernatants, extracts or other preparations of these tissues are obtained from suitable commercial sources (e.g., Pel-Freez Biologicals, Rogers, A R, or GenTest Corporation, Woburn, Mass.), or prepared by methods well known in the art.

Representative conditions typically used for in vitro studies conducted with these preparations are described in Table 1 below herein. For example, a prodrug (50 μM) is incubated with 90% human liver S9 fraction containing 1.3 mM NADPH or a suitable NADPH-generating system (e.g., 1.3 mM NADP$^+$, 3.3 mM glucose-6-phosphate, 0.4 U/mL glucose-6-phosphate dehydrogenase, 3.3 mM magnesium chloride and 0.95 mg/mL potassium phosphate, pH 7.4). The mixture is incubated at 37° C. for one hour. Aliquots (50 μL) are removed at 0, 30, and 60 min and quenched with 0.1% trifluoroacetic acid in acetonitrile. Samples are then centrifuged and analyzed by LC/MS. Similar conditions may be used with other homogenates, preparations or extracts of the tissues encountered in vivo. For drugs that are poorly absorbed, a preferred prodrug is one that demonstrates at least 1% cleavage to produce the free drug or an active metabolite thereof within a 60 minute period, when examined by one or more of methods III through XI as listed in Table 1. Additional biological matrices are examined when considered relevant to the distribution of the drug. Stability of prodrugs towards specific enzymes or enzyme mixtures (e.g., carboxylesterases, pancreatin, etc.) is also assessed in vitro by incubation with the purified enzyme.

Concentrations of prodrug or of released drug in tissue extracts were determined by direct injection of quenched samples onto an Applied Biosystems (Foster, Calif.) API 2000 LC/MS equipped with an Agilent (Palo Alto, Calif.) 1100 binary pump and autosampler. Separation was achieved using a 3.5 μm Zorbax Ellipse XDB-C8 4.4×150 mm chromatography column (Capital HPLC, Ltd., West Lothian, UK) heated to 45° C. during the analysis. The mobile phases were: 0.1% formic acid in water (A) and 0.1% formic acid in acetonitrile (B). The gradient condition was: 2% B for 0.5 min, increasing to 90% B in 2.0 min, maintained for 2.5 min and returning to 2% B for 2 min. A TurbolonSpray source was used on the API 2000. For example, the analysis was performed in the positive ion mode and MRM (multiple reaction monitoring) transitions of 172.0/137.2 were used in the analysis of gabapentin; appropriate MRM transitions were used for prodrugs depending on structure. Ten microliters of the sample extracts were injected. Peaks were integrated using Analyst quantitation software. The method was linear for gabapentin and prodrugs over the concentration range 0.002 to 10 μg/mL.

TABLE 1

Standard Conditions for In Vitro Evaluation of Prodrug Stability

| Method | Tissue | Preparation | Tissue Prep Concn. | Prodrug Concn. | Additional Cofactors | Incubation Condition |
|---|---|---|---|---|---|---|
| I | Intestinal Luminal Contents | Intestinal Wash or Pancreatic Juice | 90% | 5 μM | None | 37° C. for 1 hr |
| II | Intestinal Luminal Contents | Purified Enzymes (eg: carboxypeptidase A, pancreatin, etc.) | 90% | 5 μM | None | 37° C. for 1 hr |
| III | Small Intestinal Cells | Cultured Enterocytes | N/A | 5 μM | None | 37° C. for 1 hr |

TABLE 1-continued

Standard Conditions for In Vitro Evaluation of Prodrug Stability

| Method | Tissue | Preparation | Tissue Prep Concn. | Prodrug Concn. | Additional Cofactors | Incubation Condition |
|---|---|---|---|---|---|---|
| IV | Small Intestinal Cells | S9 Fraction or Cytosol | 90% | 5 μM | NADPH or NADPH generating system* | 37° C. for 1 hr |
| V | Small Intestinal Cells | Microsomes | 0.8 mg protein/mL | 5 μM | NADPH or NADPH generating system* | 37° C. for 1 hr |
| VI | Blood | Whole Blood, Plasma, Serum, etc. | 90% | 5 μM | None | 37° C. for 1 hr |
| VII | Liver | Cultured Hepatocytes | N/A | 5 μM | None | 37° C. for 1 hr |
| VIII | Liver | Precision Cut Liver Slices | N/A | 5 μM | None | 37° C. for 1 hr |
| IX | Liver | S9 Fraction or Cytosol | 90% | 5 μM | NADPH or NADPH generating system* | 37° C. for 1 hr |
| X | Liver | Microsomes | 0.8 mg protein/mL | 5 μM | NADPH or NADPH generating system* | 37° C. for 1 hr |
| XI | Liver | Purified Enzymes (e.g., porcine liver esterase) | 1.0 U/mL | 5 μM | Enzyme dependent | 37° C. for 1 hr |
| XII | Biliary Tract | Bile | 90% | 5 μM | None | 37° C. for 1 hr |

*NADPH generating system, e.g., 1.3 mM NADP$^+$, 3.3 mM glucose-6-phosphate, 0.4 U/mL glucose-6-phosphate dehydrogenase, 3.3 mM magnesium chloride and 0.95 mg/mL potassium phosphate, pH 7.4.

5.5 Example 5

General Procedure for the Measurement of the Uptake of Gabapentin Following Administration of Gabapentin or a Cyclic Prodrug of the Invention Intracolonically in Rats Sustained-release oral dosage forms, which release drug slowly over periods of 6-24 hours, generally release a significant proportion of the dose within the colon. Thus, drugs suitable for use in such sustained-release oral dosage forms will preferably exhibit good colonic absorption. The suitability of gabapentin prodrugs for use in an oral sustained release dosage form can be assessed using the method described below:

Rats are obtained commercially and are pre-cannulated in the both the ascending colon and the jugular vein. The rats are then fasted overnight and until 4 hours post-dosing. Gabapentin or prodrugs are administered as aqueous solutions directly into the colon via the cannula at a suitable dose, including, but not limited to 25 mg/kg. Blood samples (0.5 mL) are obtained from the jugular cannula at intervals over an 8 hour period following dosing and are quenched immediately by adding 0.3 mL of a solution of acetonitrile/methanol (1:1). The quenched samples are then processed for plasma by centrifugation and the concentration of gabapentin or prodrug in the plasma is determined by LC/MS as described above. It is to be noted that the rats remain conscious during the course of this procedure.

Examples 6 and 7 below summarize the results obtained for Compounds (44) and (47), respectively, using the methodology described in Example 5.

5.6 Example 6

Evaluation of Compound (44)

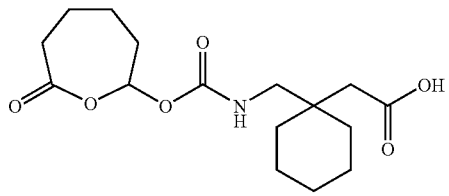

Using the method of Example 5, following intracolonic dosing of compound (44) in rats, the maximum concentration of gabapentin in plasma was 78% higher than the corresponding maximum concentration observed after intracolonic dosing of gabapentin itself at an equimolar dose.

5.7 Example 7

Evaluation of Compound (47)

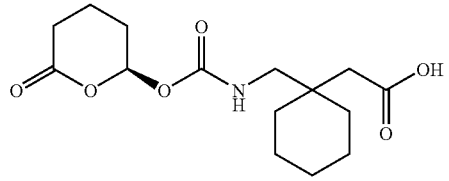

Using the method of Example 5, following intracolonic dosing of compound (47) in rats, the maximum concentration of gabapentin in plasma was 40% higher than the corresponding maximum concentration observed after intracolonic dosing of gabapentin itself at an equimolar dose.

What is claimed is:

1. A compound of Formula (I):

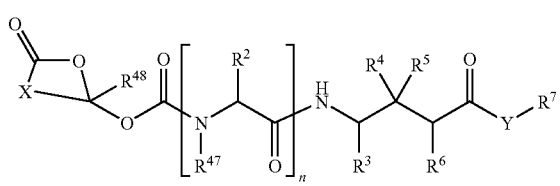

or a pharmaceutically acceptable salt, thereof, wherein:
n is 0 or 1;
Y is O or S;
X is alkyldiyl, substituted alkyldiyl, arylalkyldiyl, substituted arylalkyldiyl, aryldiyl, substituted aryldiyl, cycloheteroalkyldiyl, substituted cycloheteroalkyldiyl, heteroaryldiyl, substituted heteroaryldiyl, heteroarylalkyldiyl, substituted heteroarylalkyldiyl, heteroalkyldiyl or substituted heteroalkyldiyl;
$R^{47}$ is hydrogen, alkyl, substituted alkyl, arylalkyl or substituted arylalkyl;
$R^2$ is hydrogen, alkyl, substituted alkyl, alkoxy, substituted alkoxy, acyl, substituted acyl, acylamino, substituted acylamino, alkylamino, substituted alkylamino, alkylsulfinyl, substituted alkylsulfinyl, alkylsulfonyl, substituted alkylsulfonyl, alkylthio, substituted alkylthio, alkoxycarbonyl, substituted alkylthio, aryl, substituted aryl, arylalkyl, substituted arylalkyl, aryloxy, substituted aryloxy, carbamoyl, substituted carbamoyl, cycloalkyl, substituted cycloalkyl, cycloheteroalkyl, substituted cycloheteroalkyl, dialkylamino, substituted dialkylamino, halo, heteroalkyl, substituted heteroalkyl, heteroaryl, substituted heteroaryl, heteroarylalkyl, substituted heteroarylalkyl, heteroalkyloxy, substituted heteroalkyloxy, heteroaryloxy, substituted heteroaryloxy, or optionally, $R^{47}$ and $R^2$ taken together are alkyldiyl or substituted alkyldiyl;
$R^3$ and $R^6$ are independently selected from the group consisting of hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroaryl, substituted heteroaryl, heteroarylalkyl and substituted heteroarylalkyl;
$R^4$ and $R^5$ are independently hydrogen, alkyl, substituted alkyl, acyl, substituted acyl, aryl, substituted aryl, arylalkyl, substituted arylalkyl, cycloalkyl, substituted cycloalkyl, cycloheteroalkyl, substituted cycloheteroalkyl, heteroaryl, substituted heteroaryl, heteroarylalkyl, substituted heteroarylalkyl or optionally, $R^4$ and $R^5$ taken together are alkyldiyl, substituted alkyldiyl, heteroalkyldiyl, substituted heteroalkyldiyl, or together with the carbon atom to which they are attached form a bridged cycloalkyl ring;
$R^7$ is hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl or substituted heteroarylalkyl; and $R^{48}$ is selected from the group consisting of hydrogen, alkyl, substituted alkyl, alkoxycarbonyl, substituted alkoxycarbonyl, aryl, substituted aryl, arylalkyl, substituted arylalkyl, carbamoyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl and substituted heteroarylalkyl.

2. The compound of claim 1 having the formula:

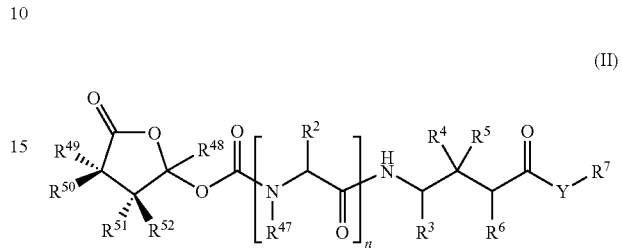

or a pharmaceutically acceptable salt, hydrate or solvate thereof, wherein:
n is 0 or 1;
Y is O or S;
$R^{47}$ is hydrogen, alkyl, substituted alkyl, arylalkyl or substituted arylalkyl;
$R^2$ is hydrogen, alkyl, substituted alkyl, alkoxy, substituted alkoxy, acyl, substituted acyl, acylamino, substituted acylamino, alkylamino, substituted alkylamino, alklysulfinyl substituted alkylsulfinyl, alkylsulfonyl, substituted alkylsulfonyl, alkylthio, substituted alkylthio, alkoxycarbonyl, substituted alkylthio, aryl, substituted aryl, arylalkyl, substituted arylalkyl, aryloxy, substituted aryloxy, carbamoyl, substituted carbamoyl, cycloalkyl, substituted cycloalkyl, cycloheteroalkyl, substituted cycloheteroalkyl, dialkylamino, substituted dialkylamino, halo, heteroalkyl, substituted heteroalkyl, heteroaryl, substituted heteroaryl, heteroarylalkyl, substituted heteroarylalkyl, heteroalkyloxy, substituted heteroalkyloxy, heteroaryloxy, substituted heteroaryloxy, or optionally, $R^{47}$ and $R^2$ taken together are alkyldiyl or substituted alkyldiyl;
$R^3$ and $R^6$ are independently selected from the group consisting of hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroaryl, substituted heteroaryl, heteroarylalkyl and substituted heteroarylalkyl;
$R^4$ and $R^5$ are independently hydrogen, alkyl, substituted alkyl, acyl, substituted acyl, aryl, substituted aryl, arylalkyl, substituted arylalkyl, cycloalkyl, substituted cycloalkyl, cycloheteroalkyl, substituted cycloheteroalkyl, heteroaryl, substituted heteroaryl, heteroarylalkyl, substituted heteroarylalkyl or optionally, $R^4$ and $R^5$ taken together are alkyldiyl, substituted alkyldiyl, heteroalkyldiyl, substituted heteroalkyldiyl, or together with the carbon atom to which they are attached form a bridged cycloalkyl ring;
$R^7$ is hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl or substituted heteroarylalkyl;
$R^{48}$ is selected from the group consisting of hydrogen, alkyl, substituted alkyl, alkoxycarbonyl, substituted alkoxycarbonyl, aryl, substituted aryl, arylalkyl, substituted arylalkyl, carbamoyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl and substituted heteroarylalkyl; and $R^{49}$, $R^{50}$, $R^{51}$ and $R^{52}$ are independently selected from the group consisting of hydrogen, alkyl, substituted alkyl, alkoxy, substituted alkoxy, acyl, substituted acyl, acylamino, substituted acylamino, acyloxy, substituted acyloxy, amino, alkylamino, substituted alkylamino, alklysulfinyl, substituted alkylsulfinyl, alkylsulfonyl, substituted alkylsulfonyl, alkylthio, substituted alkylthio, alkoxycarbonyl, substituted alkoxycarbonyl, aryl, substituted aryl, arylalkyl, substituted arylalkyl, aryloxy, substituted aryloxy, carbamoyl, cyano, cycloalkyl, substituted cycloalkyl, cycloheteroalkyl, substituted cycloheteroalkyl, dialkylamino, substituted dialkylamino, halo, heteroalkyl, substituted heteroalkyl, heteroaryl, substituted heteroaryl, heteroarylalkyl, substituted heteroarylalkyl, heteroalkyloxy, substituted heteroalkyloxy, heteroaryloxy, substituted heteroaryloxy and hydroxy, or optionally, $R^{49}$ and $R^{50}$, or $R^{51}$ and $R^{52}$ independently, together with the carbon atom(s) to which they are attached form a cycloalkyl, substituted cycloalkyl, cycloheteroalkyl or substituted cycloheteroalkyl ring, or optionally $R^{49}$ and $R^{51}$, $R^{50}$ and $R^{52}$, or $R^{49}$ and $R^{52}$ independently, together with the carbon atom(s) to which they are attached form a cycloalkyl, substituted cycloalkyl, cycloheteroalkyl or substituted cycloheteroalkyl ring.

3. The compound of claim 1 having the formula:

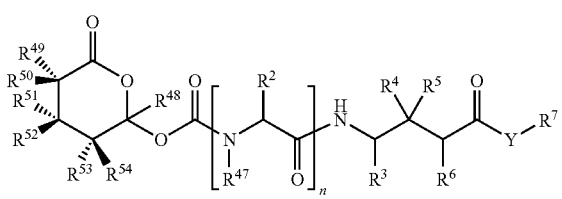

(III)

or a pharmaceutically acceptable salt, hydrate or solvate thereof, wherein:

n is 0 or 1;

Y is O or S;

$R^{47}$ is hydrogen, alkyl, substituted alkyl, arylalkyl or substituted arylalkyl;

$R^2$ is hydrogen, alkyl, substituted alkyl, alkoxy, substituted alkoxy, acyl, substituted acyl, acylamino, substituted acylamino, alkylamino, substituted alkylamino, alklysulfinyl, substituted alkylsulfinyl, alkylsulfonyl, substituted alkylsulfonyl, alkylthio, substituted alkylthio, alkoxycarbonyl, substituted alkylthio, aryl, substituted aryl, arylalkyl, substituted arylalkyl, aryloxy, substituted aryloxy, carbamoyl, substituted carbamoyl, cycloalkyl, substituted cycloalkyl, cycloheteroalkyl, substituted cycloheteroalkyl, dialkylamino, halo, heteroalkyl, substituted heteroalkyl, heteroaryl, substituted heteroaryl, heteroarylalkyl, substituted heteroarylalkyl, heteroalkyloxy, substituted heteroalkyloxy, heteroaryloxy, substituted heteroaryloxy, or optionally, $R^{47}$ and $R^2$ taken together are alkyldiyl or substituted alkyldiyl;

$R^3$ and $R^6$ are independently selected from the group consisting of hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroaryl, substituted heteroaryl, heteroarylalkyl and substituted heteroarylalkyl;

$R^4$ and $R^5$ are independently hydrogen, alkyl, substituted alkyl, acyl, substituted acyl, aryl, substituted aryl, arylalkyl, substituted arylalkyl, cycloalkyl, substituted cycloalkyl, cycloheteroalkyl, substituted cycloheteroalkyl, heteroaryl, substituted heteroaryl, heteroarylalkyl, substituted heteroarylalkyl or optionally, $R^4$ and $R^5$ taken together are alkyldiyl, substituted alkyldiyl, heteroalkyldiyl, substituted heteroalkyldiyl, or together with the carbon atom to which they are attached form a bridged cycloalkyl ring;

$R^7$ is hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl or substituted heteroarylalkyl;

$R^{48}$ is selected from the group consisting of hydrogen, alkyl, substituted alkyl, alkoxycarbonyl, substituted alkoxycarbonyl, aryl, substituted aryl, arylalkyl, substituted arylalkyl, carbamoyl, cycloalkyl, substituted cycloalkyl, cycloheteroalkyl, substituted cycloheteroalkyl, heteroalkyl substituted heteroalkyl, heteroaryl, substituted heteroaryl, heteroarylalkyl and substituted heteroarylalkyl; and $R^{49}$, $R^{50}$, $R^{51}$, $R^{52}$, $R^{53}$ and $R^{54}$ are independently selected from the group consisting of hydrogen, alkyl, substituted alkyl, alkoxy, substituted alkoxy, acyl, substituted acyl, acylamino, substituted acylamino, acyloxy, substituted acyloxy, amino, alkylamino, substituted alkylamino, alklysulfinyl, substituted alkylsulfinyl, alkylsulfonyl, substituted alkylsulfonyl, alkylthio, substituted alkylthio, alkoxycarbonyl, substituted alkoxycarbonyl, aryl, substituted aryl, arylalkyl, substituted arylalkyl, aryloxy, substituted aryloxy, carbamoyl, cyano, cycloalkyl, substituted cycloalkyl, cycloheteroalkyl, substituted cycloheteroalkyl, dialkylamino, substituted dialkylamino, halo, heteroalkyl, substituted heteroalkyl, heteroaryl, substituted heteroaryl, heteroarylalkyl, substituted heteroarylalkyl, heteroalkyloxy, substituted heteroalkyloxy, heteroaryloxy, substituted heteroaryloxy and hydroxy, or optionally, $R^{49}$ and $R^{50}$, $R^{51}$ and $R^{52}$, or $R^{53}$ and $R^{54}$, independently, together with the carbon atom(s) to which they are attached form a cycloalkyl, substituted cycloalkyl, cycloheteroalkyl or substituted cycloheteroalkyl ring, or optionally, $R^{49}$ and $R^{51}$, $R^{50}$ and $R^{52}$, $R^{49}$ and $R^{52}$, $R^{51}$ and $R^{53}$ independently, together with the carbon atom(s) to which they are attached form a cycloalkyl, substituted cycloalkyl, cycloheteroalkyl or substituted cycloheteroalkyl ring, or optionally, $R^{52}$ and $R^{54}$, $R^{51}$ and $R^{54}$, $R^{52}$ and $R^{53}$ independently, together with the carbon atom(s) to which they are attached form a cycloalkyl, substituted cycloalkyl, cycloheteroalkyl or substituted cycloheteroalkyl ring.

4. The compound of claim 1 having the formula:

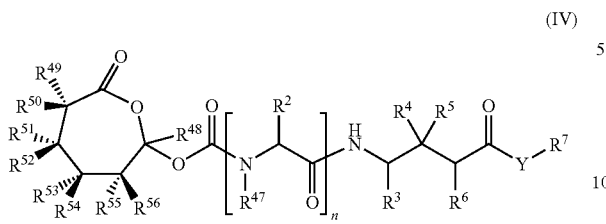

(IV)

or a pharmaceutically acceptable salt, hydrate or solvate thereof, wherein:

n is 0 or 1;

Y is O or S;

$R^{47}$ is hydrogen, alkyl, substituted alkyl, arylalkyl or substituted arylalkyl;

$R^2$ is hydrogen, alkyl, substituted alkyl, alkoxy, substituted alkoxy, acyl, substituted acyl, acylamino, substituted acylamino, alkylamino, substituted alkylamino, alklysulfinyl, substituted alkylsulfinyl, alkylsulfonyl, substituted alkylsulfonyl, alkylthio, substituted alkylthio, alkoxycarbonyl, substituted alkylthio, aryl, substituted aryl, arylalkyl, substituted arylalkyl, aryloxy, substituted aryloxy, carbamoyl, substituted carbamoyl, cycloalkyl, substituted cycloalkyl, cycloheteroalkyl, substituted cycloheteroalkyl, dialkylamino, substituted dialkylamino, halo, heteroalkyl, substituted heteroalkyl, heteroaryl, substituted heteroaryl, heteroarylalkyl, substituted heteroarylalkyl, heteroalkyloxy, substituted heteroalkyloxy, heteroaryloxy, substituted heteroaryloxy, or optionally, $R^{47}$ and $R^2$ taken together are alkyldiyl or substituted alkyldiyl;

$R^3$ and $R^6$ are independently selected from the group consisting of hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroaryl, substituted heteroaryl, heteroarylalkyl and substituted heteroarylalkyl;

$R^4$ and $R^5$ are independently hydrogen, alkyl, substituted alkyl, acyl, substituted acyl, aryl, substituted aryl, arylalkyl, substituted arylalkyl, cycloalkyl, substituted cycloalkyl, cycloheteroalkyl, substituted cycloheteroalkyl, heteroaryl, substituted heteroaryl, heteroarylalkyl, substituted heteroarylalkyl or optionally, $R^4$ and $R^5$ taken together are alkyldiyl, substituted alkyldiyl, heteroalkyldiyl, substituted heteroalkyldiyl, or together with the carbon atom to which they are attached form a bridged cycloalkyl ring;

$R^7$ is hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl or substituted heteroarylalkyl;

$R^{48}$ is selected from the group consisting of hydrogen, alkyl, substituted alkyl, alkoxycarbonyl, substituted alkoxycarbonyl, aryl, substituted aryl, arylalkyl, substituted arylalkyl, carbamoyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl and substituted heteroarylalkyl; and $R^{49}, R^{50}, R^{51}, R^{52}, R^{53}, R^{54}, R^{55}$ and $R^{56}$ are independently selected from the group consisting of hydrogen, alkyl, substituted alkyl, alkoxy, substituted alkoxy, acyl, substituted acyl, acylamino, substituted acylamino, acyloxy, substituted acyloxy, amino, alkylamino, substituted alkylamino, alklysulfinyl, substituted alkylsulfinyl, alkylsulfonyl, substituted alkylsulfonyl, alkylthio, substituted alkylthio, alkoxycarbonyl, substituted alkoxycarbonyl, aryl, substituted aryl, arylalkyl, substituted arylalkyl, aryloxy, substituted aryloxy, carbamoyl, cyano, cycloalkyl, substituted cycloalkyl, cycloheteroalkyl, substituted cycloheteroalkyl, dialkylamino, substituted dialkylamino, halo, heteroalkyl, substituted heteroalkyl, heteroaryl, substituted heteroaryl, heteroarylalkyl, substituted heteroarylalkyl, heteroalkyloxy, substituted heteroalkyloxy, heteroaryloxy, substituted heteroaryloxy and hydroxy, or optionally, $R^{49}$ and $R^{50}$, $R^{51}$ and $R^{52}$, $R^{53}$ and $R^{54}$, $R^{55}$ and $R^{56}$, independently, together with the carbon atom(s) to which they are attached form a cycloalkyl, substituted cycloalkyl, cycloheteroalkyl or substituted cycloheteroalkyl ring, or optionally $R^{49}$ and $R^{51}$, $R^{50}$ and $R^{52}$, $R^{49}$ and $R^{52}$, $R^{51}$ and $R^{53}$ independently, together with the carbon atom(s) to which they are attached form a cycloalkyl, substituted cycloalkyl, cycloheteroalkyl or substituted cycloheteroalkyl ring, or optionally, $R^{52}$ and $R^{54}$, $R^{51}$ and $R^{54}$, $R^{52}$ and $R^{53}$ independently, together with the carbon atom(s) to which they are attached form a cycloalkyl, substituted cycloalkyl, cycloheteroalkyl or substituted cycloheteroalkyl ring, or optionally, $R^{53}$ and $R^{55}$, $R^{54}$ and $R^{56}$, $R^{53}$ and $R^{56}$ and $R^{54}$ and $R^{55}$ independently, together with the carbon atom(s) to which they are attached form a cycloalkyl, substituted cycloalkyl, cycloheteroalkyl or substituted cycloheteroalkyl ring.

5. The compound of claim 1 having the formula:

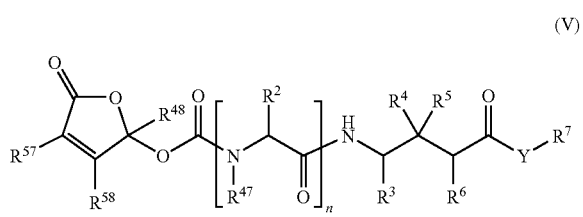

(V)

or a pharmaceutically acceptable salt, hydrate or solvate thereof, wherein:

n is 0 or 1;

Y is O or S;

$R^{47}$ is hydrogen, alkyl, substituted alkyl, arylalkyl or substituted arylalkyl;

$R^2$ is hydrogen, alkyl, substituted alkyl, alkoxy, substituted alkoxy, acyl, substituted acyl, acylamino, substituted acylamino, alkylamino, substituted alkylamino, alklysulfinyl, substituted alkylsulfinyl, alkylsulfonyl, substituted alkylsulfonyl, alkylthio, substituted alkylthio, alkoxycarbonyl, substituted alkylthio, aryl, substituted aryl, arylalkyl, substituted arylalkyl, aryloxy, substituted aryloxy, carbamoyl, substituted carbamoyl, cycloalkyl, substituted cycloalkyl, cycloheteroalkyl, substituted cycloheteroalkyl, dialkylamino, substituted dialkylamino, halo, heteroalkyl, substituted heteroalkyl, heteroaryl, substituted heteroaryl, heteroarylalkyl, substituted heteroarylalkyl, heteroalkyloxy, substituted heteroalkyloxy, heteroaryloxy, substituted heteroaryloxy, or optionally, $R^{47}$ and $R^2$ taken together are alkyldiyl or substituted alkyldiyl;

$R^3$ and $R^6$ are independently selected from the group consisting of hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroaryl, substituted heteroaryl, heteroarylalkyl and substituted heteroarylalkyl;

$R^4$ and $R^5$ are independently hydrogen, alkyl, substituted alkyl, acyl, substituted acyl, aryl, substituted aryl, arylalkyl, substituted arylalkyl, cycloalkyl, substituted cycloalkyl, cycloheteroalkyl, substituted cycloheteroalkyl, heteroaryl, substituted heteroaryl, heteroarylalkyl, substituted heteroarylalkyl or optionally, $R^4$ and $R^5$ taken together are alkyldiyl, substituted alkyldiyl, heteroalkyldiyl, substituted heteroalkyldiyl, or together with the carbon atom to which they are attached form a bridged cycloalkyl ring;

$R^7$ is hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl or substituted heteroarylalkyl;

$R^{48}$ is selected from the group consisting of hydrogen, alkyl, substituted alkyl, alkoxycarbonyl, substituted alkoxycarbonyl, aryl, substituted aryl, arylalkyl, substituted arylalkyl, carbamoyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl and substituted heteroarylalkyl; and $R^{57}$ and $R^{58}$ are independently selected from the group consisting of hydrogen, alkyl, substituted alkyl, acylamino, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl and substituted heteroarylalkyl, or optionally $R^{57}$ and $R^{58}$ together with the carbon atoms to which they are attached form an aryl, substituted aryl, heteroaryl, substituted heteroaryl, cycloalkyl, substituted cycloalkyl, cycloheteroalkyl or substituted cycloheteroalkyl ring.

6. The compound of claim 1 having the formula:

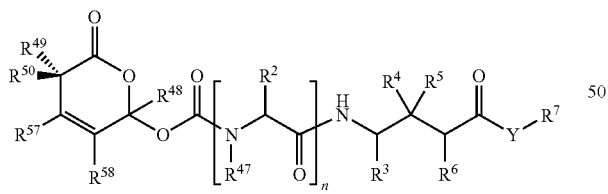

(VI)

or a pharmaceutically acceptable salt, hydrate or solvate thereof, wherein:

n is 0 or 1;

Y is O or S;

$R^{47}$ is hydrogen, alkyl, substituted alkyl, arylalkyl or substituted arylalkyl;

$R^2$ is hydrogen, alkyl, substituted alkyl, alkoxy, substituted alkoxy, acyl, substituted acyl, acylamino, acyloxy, alkylamino, substituted alkylamino, alklysulfinyl, substituted alkylsulfinyl, alkylsulfonyl, substituted alkylsulfonyl, alkylthio, substituted alkylthio, alkoxycarbonyl, substituted alkylthio, aryl, substituted aryl, arylalkyl, substituted arylalkyl, aryloxy, substituted aryloxy, carbamoyl, substituted carbamoyl, cycloalkyl, substituted cycloalkyl, cycloheteroalkyl, substituted cycloheteroalkyl, dialkylamino, substituted dialkylamino, halo, heteroalkyl, substituted heteroalkyl, heteroaryl, substituted heteroaryl, heteroarylalkyl, substituted heteroarylalkyl, heteroalkyloxy, substituted heteroalkyloxy, heteroaryloxy, substituted heteroaryloxy, or optionally, $R^{47}$ and $R^2$ taken together are alkyldiyl or substituted alkyldiyl;

$R^3$ and $R^6$ are independently selected from the group consisting of hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroaryl, substituted heteroaryl, heteroarylalkyl and substituted heteroarylalkyl;

$R^4$ and $R^5$ are independently hydrogen, alkyl, substituted alkyl, acyl, substituted acyl, aryl, substituted aryl, arylalkyl, substituted arylalkyl, cycloalkyl, substituted cycloalkyl, cycloheteroalkyl, substituted cycloheteroalkyl, heteroaryl, substituted heteroaryl, heteroarylalkyl, substituted heteroarylalkyl or optionally, $R^4$ and $R^5$ taken together are alkyldiyl, substituted alkyldiyl, heteroalkyldiyl, substituted heteroalkyldiyl, or together with the carbon atom to which they are attached form a bridged cycloalkyl ring;

$R^7$ is hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl or substituted heteroarylalkyl;

$R^{48}$ is selected from the group consisting of hydrogen, alkyl, substituted alkyl, alkoxycarbonyl, substituted alkoxycarbonyl, aryl, substituted aryl, arylalkyl, substituted arylalkyl, carbamoyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl and substituted heteroarylalkyl;

$R^{49}$ and $R^{50}$ are independently selected from the group consisting of hydrogen, alkyl, substituted alkyl, alkoxy, substituted alkoxy, acyl, substituted acyl, acylamino, substituted acylamino, acyloxy, substituted acyloxy, amino, alkylamino, substituted alkylamino, alklysulfinyl, substituted alkylsulfinyl, alkylsulfonyl, substituted alkylsulfonyl, alkylthio, substituted alkylthio, alkoxycarbonyl, substituted alkoxycarbonyl, aryl, substituted aryl, arylalkyl, substituted arylalkyl, aryloxy, substituted aryloxy, carbamoyl, cyano, cycloalkyl, substituted cycloalkyl, cycloheteroalkyl, substituted cycloheteroalkyl, dialkylamino, substituted dialkylamino, halo, heteroalkyl, substituted heteroalkyl, heteroaryl, substituted heteroaryl, heteroarylalkyl, substituted heteroarylalkyl, heteroalkyloxy, substituted heteroalkyloxy, heteroaryloxy, substituted heteroaryloxy and hydroxy, or optionally, $R^{49}$ and $R^{50}$ together with the carbon atom(s) to which they are attached form a cycloalkyl, substituted cycloalkyl, cycloheteroalkyl or substituted cycloheteroalkyl ring; and $R^{57}$ and $R^{58}$ are independently selected from the group consisting of hydrogen, alkyl, substituted alkyl, acylamino, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl and substituted heteroarylalkyl, or optionally R⁵⁷ and R⁵⁸ together with the carbon atoms to which they are attached form an aryl, substituted aryl, heteroaryl, substituted heteroaryl, cycloalkyl, substituted cycloalkyl, cycloheteroalkyl or substituted cycloheteroalkyl ring.

7. The compound of claim 1 having the formula:

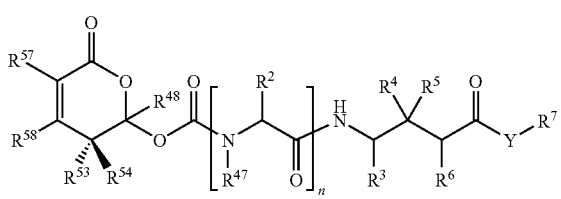

(VII)

or a pharmaceutically acceptable salt, hydrate or solvate thereof, wherein:

n is 0 or 1;

Y is O or S;

R⁴⁷ is hydrogen, alkyl, substituted alkyl, arylalkyl or substituted arylalkyl;

R² is hydrogen, alkyl, substituted alkyl, alkoxy, substituted alkoxy, acyl, substituted acyl, acylamino, substituted acylamino, alkylamino, substituted alkylamino, alklysulfinyl, substituted alkylsulfinyl, alkylsulfonyl, substituted alkylsulfonyl, alkylthio, substituted alkylthio, alkoxycarbonyl, substituted alkylthio, aryl, substituted aryl, arylalkyl, substituted arylalkyl, aryloxy, substituted aryloxy, carbamoyl, substituted carbamoyl, cycloalkyl, substituted cycloalkyl, cycloheteroalkyl, substituted cycloheteroalkyl, dialkylamino, substituted dialkylamino, halo, heteroalkyl, substituted heteroalkyl, heteroaryl, substituted heteroaryl, heteroarylalkyl, substituted heteroarylalkyl, heteroalkyloxy, substituted heteroalkyloxy, heteroaryloxy, substituted heteroaryloxy, or optionally, R⁴⁷ and R² taken together are alkyldiyl or substituted alkyldiyl;

R³ and R⁶ are independently selected from the group consisting of hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroaryl, substituted heteroaryl, heteroarylalkyl and substituted heteroarylalkyl;

R⁴ and R⁵ are independently hydrogen, alkyl, substituted alkyl, acyl, substituted acyl, aryl, substituted aryl, arylalkyl, substituted arylalkyl, cycloalkyl, substituted cycloalkyl, cycloheteroalkyl, substituted cycloheteroalkyl, heteroaryl, substituted heteroaryl, heteroarylalkyl, substituted heteroarylalkyl or optionally, R⁴ and R⁵ taken together are alkyldiyl, substituted alkyldiyl, heteroalkyldiyl, substituted heteroalkyldiyl, or together with the carbon atom to which they are attached form a bridged cycloalkyl ring;

R⁷ is hydrogen, alkyl, substituted alkyl, aryl, substituted aryl, arylalkyl, substituted arylalkyl, cycloalkyl. substituted cycloalkyl, cycloheteroalkyl, substituted cycloheteroalkyl, heteroalkyl, substituted heteroalkyl, heteroaryl, substituted heteroaryl, heteroarylalkyl or substituted heteroarylalkyl;

R⁴⁸ is selected from the group consisting of hydrogen, alkyl, substituted alkyl, alkoxycarbonyl, substituted alkoxycarbonyl, aryl, substituted aryl, arylalkyl, substituted arylalkyl, carbamoyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl and substituted heteroarylalkyl;

R⁵³ and R⁵⁴ are independently selected from the group consisting of hydrogen, alkyl, substituted alkyl, alkoxy, substituted alkoxy, acyl, substituted acyl, acylamino, substituted acylamino, acyloxy, substituted acyloxy, amino, alkylamino, substituted alkylamino, alklysulfinyl, substituted alkylsulfinyl, alkylsulfonyl, substituted alkylsulfonyl, alkylthio, substituted alkylthio, alkoxycarbonyl, substituted alkoxycarbonyl, aryl, substituted aryl, arylalkyl, substituted arylalkyl, aryloxy, substituted aryloxy, carbamoyl, cyano, cycloalkyl, substituted cycloalkyl, cycloheteroalkyl, substituted cycloheteroalkyl, dialkylamino, substituted dialkylamino, halo, heteroalkyl, substituted heteroalkyl, heteroaryl, substituted heteroaryl, heteroarylalkyl, substituted heteroarylalkyl, heteroalkyloxy, substituted heteroalkyloxy, heteroaryloxy, substituted heteroaryloxy and hydroxy, or optionally, R⁵³ and R⁵⁴ together with the carbon atom(s) to which they are attached form a cycloalkyl, substituted cycloalkyl, cycloheteroalkyl or substituted cycloheteroalkyl ring; and R⁵⁷ and R⁵⁸ are independently selected from the group consisting of hydrogen, alkyl, substituted alkyl, acylamino, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl and substituted heteroarylalkyl, or optionally R⁵⁷ and R⁵⁸ together with the carbon atoms to which they are attached form an aryl, substituted aryl, heteroaryl, substituted heteroaryl, cycloalkyl, substituted cycloalkyl, cycloheteroalkyl or substituted cycloheteroalkyl ring.

8. The compound of claim 1 having the formula:

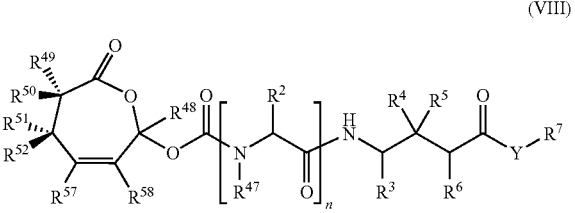

(VIII)

or a pharmaceutically acceptable salt, hydrate or solvate thereof, wherein:

n is 0 or 1;

Y is O or S;

R⁴⁷ is hydrogen, alkyl, substituted alkyl, arylalkyl or substituted arylalkyl;

R² is hydrogen, alkyl, substituted alkyl, alkoxy, substituted alkoxy, acyl, substituted acyl, acylamino, substituted acylamino, alkylamino, substituted alkylamino, alklysulfinyl, substituted alkylsulfinyl, alkylsulfonyl, substituted alkylsulfonyl, alkylthio, substituted alkylthio, alkoxycarbonyl, substituted alkylthio, aryl, substituted aryl, arylalkyl, substituted arylalkyl, aryloxy, substituted aryloxy, carbamoyl, substituted carbamoyl, cycloalkyl, substituted cycloalkyl, cycloheteroalkyl, substituted cycloheteroalkyl, dialkylamino, halo, heteroalkyl, substituted heteroalkyl, heteroaryl, substituted heteroaryl, heteroarylalkyl, substituted heteroarylalkyl, heteroalkyloxy, substituted heteroalkyloxy, heteroaryloxy, substituted heteroaryloxy, or optionally, $R^{47}$ and $R^2$ taken together are alkyldiyl or substituted alkyldiyl;

$R^3$ and $R^6$ are independently selected from the group consisting of hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroaryl, substituted heteroaryl, heteroarylalkyl and substituted heteroarylalkyl;

$R^4$ and $R^5$ are independently hydrogen, alkyl, substituted alkyl, acyl, substituted acyl, aryl, substituted aryl, arylalkyl, substituted arylalkyl, cycloalkyl, substituted cycloalkyl, cycloheteroalkyl, substituted cycloheteroalkyl, heteroaryl, substituted heteroaryl, heteroarylalkyl, substituted heteroarylalkyl or optionally, $R^4$ and $R^5$ taken together are alkyldiyl, substituted alkyldiyl, heteroalkyldiyl, substituted heteroalkyldiyl, or together with the carbon atom to which they are attached form a bridged cycloalkyl ring;

$R^7$ is hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl or substituted heteroarylalkyl;

$R^{48}$ is selected from the group consisting of hydrogen, alkyl, substituted alkyl, alkoxycarbonyl, substituted alkoxycarbonyl, aryl, substituted aryl, arylalkyl, substituted arylalkyl, carbamoyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl and substituted heteroarylalkyl;

$R^{49}$, $R^{50}$, $R^{51}$ and $R^{52}$ are independently selected from the group consisting of hydrogen, alkyl, substituted alkyl, alkoxy, substituted alkoxy, acyl, substituted acyl, acylamino, substituted acylamino, acyloxy, substituted acyloxy, amino, alkylamino, substituted alkylamino, alklysulfinyl, substituted alkylsulfinyl, alkylsulfonyl, substituted alkylsulfonyl, alkylthio, substituted alkylthio, alkoxycarbonyl, substituted alkoxycarbonyl, aryl, substituted aryl, arylalkyl, substituted arylalkyl, aryloxy, substituted aryloxy, carbamoyl, cyano, cycloalkyl, substituted cycloalkyl, cycloheteroalkyl, substituted cycloheteroalkyl, dialkylamino, substituted dialkylamino, halo, heteroalkyl, substituted heteroalkyl, heteroaryl, substituted heteroaryl, heteroarylalkyl, substituted heteroarylalkyl, heteroalkyloxy, substituted heteroalkyloxy, heteroaryloxy, substituted heteroaryloxy and hydroxy, or optionally, $R^{49}$ and $R^{50}$, or $R^{51}$ and $R^{52}$ independently, together with the carbon atom(s) to which they are attached form a cycloalkyl, substituted cycloalkyl, cycloheteroalkyl or substituted cycloheteroalkyl ring, or optionally, $R^{49}$ and $R^{51}$, $R^{50}$ and $R^{52}$, or $R^{49}$ and $R^{52}$, independently, together with the carbon atom(s) to which they are attached form a cycloalkyl, substituted cycloalkyl, cycloheteroalkyl or substituted cycloheteroalkyl ring; and $R^{57}$ and $R^{58}$ are independently selected from the group consisting of hydrogen, alkyl, substituted alkyl, acylamino, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl and substituted heteroarylalkyl, or optionally $R^{57}$ and $R^{58}$ together with the carbon atoms to which they are attached form an aryl, substituted aryl, heteroaryl, substituted heteroaryl, cycloalkyl, substituted cycloalkyl, cycloheteroalkyl or substituted cycloheteroalkyl ring.

9. The compound of claim 1 having the formula:

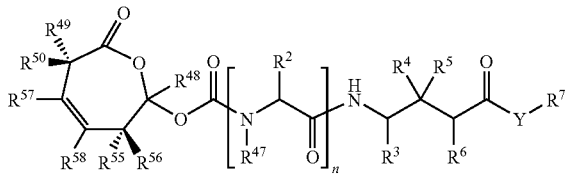

(IX)

or a pharmaceutically acceptable salt, hydrate or solvate thereof, wherein:

n is 0 or 1;

Y is O or S;

$R^{47}$ is hydrogen, alkyl, substituted alkyl, arylalkyl or substituted arylalkyl;

$R^2$ is hydrogen, alkyl, substituted alkyl, alkoxy, substituted alkoxy, acyl, substituted acyl, acylamino, substituted acylamino, alkylamino, substituted alkylamino, alklysulfinyl, substituted alkylsulfinyl, alkylsulfonyl, substituted alkylsulfonyl, alkylthio, substituted alkylthio, alkoxycarbonyl, substituted alkylthio, aryl, substituted aryl, arylalkyl, substituted arylalkyl, aryloxy, substituted aryloxy, carbamoyl, substituted carbamoyl, cycloalkyl, substituted cycloalkyl, cycloheteroalkyl, substituted cycloheteroalkyl, dialkylamino, substituted dialkylamino, halo, heteroalkyl, substituted heteroalkyl, heteroaryl, substituted heteroaryl, heteroarylalkyl, substituted heteroarylalkyl, heteroalkyloxy, substituted heteroalkyloxy, heteroaryloxy, substituted heteroaryloxy, or optionally, $R^{47}$ and $R^2$ taken together are alkyldiyl or substituted alkyldiyl;

$R^3$ and $R^6$ are independently selected from the group consisting of hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroaryl, substituted heteroaryl, heteroarylalkyl and substituted heteroarylalkyl;

$R^4$ and $R^5$ are independently hydrogen, alkyl, substituted alkyl, acyl, substituted acyl, aryl, substituted aryl, arylalkyl, substituted arylalkyl, cycloalkyl, substituted cycloalkyl, cycloheteroalkyl, substituted cycloheteroalkyl, heteroaryl, substituted heteroaryl, heteroarylalkyl, substituted heteroarylalkyl or optionally, $R^4$ and $R^5$ taken together are alkyldiyl, substituted alkyldiyl, heteroalkyldiyl, substituted heteroalkyldiyl, or together with the carbon atom to which they are attached form a bridged cycloalkyl ring;

$R^7$ is hydrogen, alkyl. substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl or substituted heteroarylalkyl;

$R^{48}$ is selected from the group consisting of hydrogen, alkyl, substituted alkyl, alkoxycarbonyl, substituted alkoxycarbonyl, aryl, substituted aryl, arylalkyl, substituted arylalkyl, carbamoyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl and substituted heteroarylalkyl;

$R^{49}$, $R^{50}$, $R^{55}$ and $R^{56}$ are independently selected from the group consisting of hydrogen, alkyl, substituted alkyl, alkoxy, substituted alkoxy, acyl, substituted acyl, acylamino, substituted acylamino, acyloxy, substituted acyloxy, amino, alkylamino, substituted alkylamino, alklysulfinyl, substituted alkylsulfinyl, alkylsulfonyl, substituted alkylsulfonyl, alkylthio, substituted alkylthio, alkoxycarbonyl, substituted alkoxycarbonyl, aryl, substituted aryl, arylalkyl, substituted arylalkyl, aryloxy, substituted aryloxy, carbamoyl, cyano, cycloalkyl, substituted cycloalkyl, cycloheteroalkyl, substituted cycloheteroalkyl, dialkylamino, substituted dialkylamino, halo, heteroalkyl, substituted heteroalkyl, heteroaryl, substituted heteroaryl, heteroarylalkyl, substituted heteroarylalkyl, heteroalkyloxy, substituted heteroalkyloxy, heteroaryloxy, substituted heteroaryloxy and hydroxy, or optionally, $R^{49}$ and $R^{50}$, or $R^{55}$ and $R^{56}$, independently, together with the carbon atom(s) to which they are attached form a cycloalkyl, substituted cycloalkyl, cycloheteroalkyl or substituted cycloheteroalkyl ring; and $R^{57}$ and $R^{58}$ are independently selected from the group consisting of hydrogen, alkyl, substituted alkyl, acylamino, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl and substituted heteroarylalkyl, or optionally $R^{57}$ and $R^{58}$ together with the carbon atoms to which they are attached form an aryl, substituted aryl, heteroaryl, substituted heteroaryl, cycloalkyl, substituted cycloalkyl, cycloheteroalkyl or substituted cycloheteroalkyl ring.

10. The compound of claim 1 having the formula:

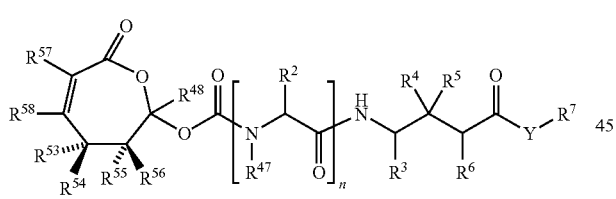

(X)

or a pharmaceutically acceptable salt, hydrate or solvate thereof, wherein:

n is 0 or 1;

Y is O or S;

$R^{47}$ is hydrogen, alkyl, substituted alkyl, arylalkyl or substituted arylalkyl;

$R^2$ is hydrogen, alkyl, substituted alkyl, alkoxy, substituted alkoxy, acyl, substituted acyl, acylamino, substituted acylamino, alkylamino, substituted alkylamino, alklysulfinyl, substituted alkylsulfinyl, alkylsulfonyl, substituted alkylsulfonyl, alkylthio, substituted alkylthio, alkoxycarbonyl, substituted alkylthio, aryl, substituted aryl, arylalkyl, substituted arylalkyl, aryloxy, substituted aryloxy, carbamoyl, substituted carbamoyl, cycloalkyl, substituted cycloalkyl, cycloheteroalkyl, substituted cycloheteroalkyl, dialkylamino, substituted dialkylamino, halo, heteroalkyl, substituted heteroalkyl, heteroaryl, substituted heteroaryl, heteroarylalkyl, substituted heteroarylalkyl, heteroalkyloxy, substituted heteroalkyloxy, heteroaryloxy, substituted heteroaryloxy, or optionally, $R^{47}$ and $R^2$ taken together are alkyldiyl or substituted alkyldiyl;

$R^3$ and $R^6$ are independently selected from the group consisting of hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroaryl, substituted heteroaryl, heteroarylalkyl and substituted heteroarylalkyl;

$R^4$ and $R^5$ are independently hydrogen, alkyl, substituted alkyl, acyl, substituted acyl, aryl, substituted aryl, arylalkyl, substituted arylalkyl, cycloalkyl, substituted cycloalkyl, cycloheteroalkyl, substituted cycloheteroalkyl, heteroaryl, substituted heteroaryl, heteroarylalkyl, substituted heteroarylalkyl or optionally, $R^4$ and $R^5$ taken together are alkyldiyl, substituted alkyldiyl, heteroalkyldiyl, substituted heteroalkyldiyl, or together with the carbon atom to which they are attached form a bridged cycloalkyl ring;

$R^7$ is hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl or substituted heteroarylalkyl;

$R^{48}$ is selected from the group consisting of hydrogen, alkyl, substituted alkyl, alkoxycarbonyl, substituted alkoxycarbonyl, aryl, substituted aryl, arylalkyl, substituted arylalkyl, carbamoyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl and substituted heteroarylalkyl;

$R^{53}$, $R^{54}$, $R^{55}$ and $R^{56}$ are independently selected from the group consisting of hydrogen, alkyl, substituted alkyl, alkoxy, substituted alkoxy, acyl, substituted acyl, acylamino, substituted acylamino, acyloxy, substituted acyloxy, amino, alkylamino, substituted alkylamino, alklysulfinyl, substituted alkylsulfinyl, alkylsulfonyl, substituted alkylsulfonyl, alkylthio, substituted alkylthio, alkoxycarbonyl, substituted alkoxycarbonyl, aryl, substituted aryl, arylalkyl, substituted arylalkyl, aryloxy, substituted aryloxy, carbamoyl, cyano, cycloalkyl, substituted cycloalkyl, cycloheteroalkyl, substituted cycloheteroalkyl, dialkylamino, substituted dialkylamino, halo, heteroalkyl, substituted heteroalkyl, heteroaryl, substituted heteroaryl, heteroarylalkyl, substituted heteroarylalkyl, heteroalkyloxy, substituted heteroalkyloxy, heteroaryloxy, substituted heteroaryloxy and hydroxy, or optionally, $R^{53}$ and $R^{54}$, or $R^{55}$ and $R^{56}$, independently, together with the carbon atom(s) to which they are attached form a cycloalkyl, substituted cycloalkyl, cycloheteroalkyl or substituted cycloheteroalkyl ring, or optionally, $R^{53}$ and $R^{55}$, $R^{54}$ and $R^{56}$, $R^{53}$ and $R^{56}$ and $R^{54}$ and $R^{55}$ independently, together with the carbon atom(s) to which they are attached form a cycloalkyl, substituted cycloalkyl, cycloheteroalkyl or substituted cycloheteroalkyl ring; and $R^{57}$ and $R^{58}$ are independently selected from the group consisting of hydrogen, alkyl, substituted alkyl, acylamino, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl and substituted heteroarylalkyl, or optionally $R^{57}$ and $R^{58}$ together with the carbon atoms to which they are attached form an aryl, substituted aryl, heteroaryl, substituted heteroaryl, cycloalkyl, substituted cycloalkyl, cycloheteroalkyl or substituted cycloheteroalkyl ring.

11. The compound of claim 1 wherein n is 0.

12. The compound of claim 1 wherein Y is O and $R^7$ is hydrogen, alkanyl, substituted alkanyl, alkenyl, substituted alkenyl, aryl or substituted aryl.

13. The compound of claim 12 wherein $R^7$ is —C(CH$_3$)=CH$_2$, —CH$_2$C(O)N(CH$_3$)$_2$, —CH$_2$C(O)N(CH$_2$CH$_3$)$_2$,

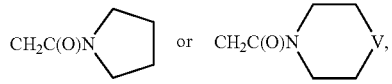

wherein V is O or CH$_2$.

14. The compound of claim 1 wherein $R^{47}$ is H and $R^2$ is hydrogen, alkanyl, substituted alkanyl, aryl, substituted aryl, arylalkanyl, substituted arylalkanyl, cycloalkanyl, heteroarylalkyl and substituted heteroarylalkanyl.

15. The compound of claim 14 wherein $R^2$ is hydrogen, methyl, 2-propyl, 2-butyl, isobutyl, t-butyl, cyclopentyl, cyclohexyl, —CH$_2$OH, —CH(OH)CH$_3$, —CH$_2$CO$_2$H, —CH$_2$CH$_2$CO$_2$H, —CH$_2$CONH$_2$, —CH$_2$CH$_2$CONH$_2$, —CH$_2$CH$_2$SCH$_3$, —CH$_2$SH, —CH$_2$(CH$_2$)$_3$NH$_2$, —CH$_2$CH$_2$CH$_2$NHC(NH)NH$_2$, phenyl, benzyl, 4-hydroxybenzyl, 2-imidazolyl or 2-indolyl.

16. The compound of claim 1 wherein $R^{47}$ and $R^2$ together with the atoms to which they are attached form an azetidine, pyrrolidine or piperidine ring.

17. The compound of claim 1 wherein $R^3$ and $R^6$ are independently selected from hydrogen and alkanyl.

18. The compound of claim 1 wherein $R^4$ and $R^5$ are independently selected from hydrogen, alkanyl and substituted alkanyl.

19. The compound of claim 1 wherein $R^4$ and $R^5$ together with the carbon atom to which they are attached are cycloalkanyl, substituted cycloalkanyl, cycloheteroalkyl, substituted cycloheteroalkyl or bridged cycloalkyl.

20. The compound of claim 19 wherein $R^4$ and $R^5$ together with the carbon atom to which they are attached are cyclobutyl, substituted cyclobutyl, cyclopentyl, substituted cyclopentyl, cyclohexyl or substituted cyclohexyl.

21. The compound of claim 1 wherein X is —(CH$_2$)$_z$— and z is an integer ranging from 2 to 5.

22. The compound of claim 21 wherein X is —(CH$_2$)$_5$—.

23. The compound of claim 21 wherein $R^{48}$ is hydrogen.

24. The compound of claim 1, wherein $R^{48}$ is hydrogen, methyl, ethyl, isopropyl, methoxycarbonyl, ethoxycarbonyl, isopropoxycarbonyl or phenyl.

25. The compound of claim 24, wherein $R^{48}$ is hydrogen.

26. The compound of claim 1, wherein n is 1.

27. The compound of claim 26, wherein $R^{47}$ is hydrogen, and $R^2$ is hydrogen, methyl, 2-propyl, 2-butyl, isobutyl, t-butyl, cyclopentyl or cyclohexyl.

28. The compound of claim 26, wherein $R^{47}$ is hydrogen, and $R^2$ is —CH$_2$OH, —CH(OH)CH$_3$, —CH$_2$CO$_2$H, —CH$_2$CH$_2$CO$_2$H, —CH$_2$CONH$_2$, —CH$_2$CH$_2$CONH$_2$, —CH$_2$CH$_2$SCH$_3$, —CH$_2$SH, —CH$_2$(CH$_2$)$_3$NH$_2$ or —CH$_2$CH$_2$CH$_2$NHC(NH)NH$_2$.

29. The compound of claim 26, wherein $R^{47}$ is hydrogen, and $R^2$ is phenyl, benzyl, 4-hydroxybenzyl, 2-imidazolyl or 2-indolyl.

30. The compound of claim 26, wherein the α-amino acid within the square brackets of Formula (I) is of the L-stereochemical configuration or is glycine.

* * * * *